US010537529B2

(12) United States Patent
Mrazek

(10) Patent No.: US 10,537,529 B2
(45) Date of Patent: Jan. 21, 2020

(54) CELL-FREE METHODS OF PRODUCING VAULT PARTICLES AND VAULT PARTICLES RESULTING THEREFROM

(71) Applicant: The Regents of the University of California, Oakland, CA (US)

(72) Inventor: Jan Mrazek, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 251 days.

(21) Appl. No.: 15/509,723

(22) PCT Filed: Sep. 23, 2015

(86) PCT No.: PCT/US2015/051618
§ 371 (c)(1),
(2) Date: Mar. 8, 2017

(87) PCT Pub. No.: WO2016/049122
PCT Pub. Date: Mar. 31, 2016

(65) Prior Publication Data
US 2017/0246119 A1 Aug. 31, 2017

Related U.S. Application Data

(60) Provisional application No. 62/054,778, filed on Sep. 24, 2014.

(51) Int. Cl.
*A61K 9/50* (2006.01)
*C07K 14/47* (2006.01)
*A61K 31/713* (2006.01)
*A61K 38/38* (2006.01)

(52) U.S. Cl.
CPC .......... *A61K 9/5052* (2013.01); *A61K 31/713* (2013.01); *A61K 38/38* (2013.01); *C07K 14/47* (2013.01)

(58) Field of Classification Search
CPC .................................................. A61K 9/5052
See application file for complete search history.

(56) References Cited

U.S. PATENT DOCUMENTS

| 2009/0317861 A1 | 12/2009 | Bundy et al. |
| 2010/0086610 A1 | 4/2010 | Rome et al. |
| 2013/0224828 A1 | 8/2013 | Finn et al. |
| 2013/0344564 A1 | 12/2013 | Rome et al. |

FOREIGN PATENT DOCUMENTS

WO   WO2012/061445   *   5/2012

OTHER PUBLICATIONS

Casañas et al. (Current Opinion in Biotechnology 2012, 23:972-977). (Year: 2012).*
Shimizu et al. (Methods Jul. 2005; 36(3):299-304). (Year: 2005).*
Kickhoefer, et al., "Vaults are the answer, what is the question?", May 1, 1996, pp. 174-178, vol. 6, No. 5, Publisher: Trends in Cell Biology.
Kong, et al., "Structure of the vault, a ubiquitous celular component", Apr. 15, 1999, pp. 371-379, vol. 7, No. 4, Publisher: Structure.
Mrazek, et al., "Polyribosomes Are Molecular 3D Nanoprinters That Orchestrate the Assembly of Vault Particles", Nov. 25, 2014, pp. 11552-11559, vol. 8, No. 11, Publisher: ACS Nano.
Supplementary Partial European Search Report received in EP 15845254, dated Apr. 5, 2018.
Suprenant, et al., "Vault Ribonucleoprotein Particles: Sarcophagi, Gondolas, or Safety Deposit Boxes?", Oct. 23, 2002, pp. 14447-14454, vol. 41, No. 49, Publisher: biochemistry.
Van Zon, et al., "Structural Domains of Vault Proteins: A Role for the Coiled Coil Domain in Vault Assembly", Mar. 1, 2002, pp. 535-541, vol. 291, No. 3, Publisher: Biochemical and Biophysical Research Communications.
Buehler, et al., "Bioengineered Vaults: Self-Assembling Protein Shell Lipophilic Core Nanoparticles for Drug Delivery", Jul. 25, 2014, pp. 7723-7732, vol. 8, No. 8, Publisher: ACS Nano.
Chugani, et al., "Evidence that vault ribonucleoprotein particles localize to the nuclear pore complex", May 20, 1993, pp. 23-29, vol. 106, Publisher: Journal of Cell Science.
Dickenson, et al., "Vault Ribonucleoprotein Particles and the Central Mass of the Nuclear Pore Complex", Jan. 8, 2007, pp. 686691, vol. 83, Publisher: Photochemistry and Photobiology.
Endo, et al., "Cell-free expression systems for eukaryotic protein production", Jul. 7, 2006, pp. 373380, vol. 17, Publisher: Current Opinion in Biotechnology.
Habers, et al., "Wheat germ systems for cell-free protein expression", Jun. 12, 2014, pp. 2762-2773, vol. 588, Publisher: FEBS Letters.
International Search Report received in PCT/US2015/051618 dated Dec. 28, 2015.
Park, et al., "High-yield cell-free protein production from P-gel", Nov. 12, 2009, pp. 1757-1770, vol. 4, No. 12, Publisher: Nature Protocols.
Rome, et al., Dec. 26, 2012, pp. 889-902, vol. 7, No. 2, Publisher: ACS Nano.
Shirokov, et al., "Continuous-exchange protein-synthesizing systems.", Jan. 1, 2007, pp. 19-55, vol. 375, Publisher: Methods Mol. Biol.
Stephen, et al., "Assembly of Vault-like Particles in Insect Cells Expressing Only the Major Vault Protein", May 10, 2001, pp. 23217-23220, vol. 276, No. 26, Publisher: J. Biological Chemistry.
Takai, et al., "Practical cell-free protein synthesis system using purified wheat embryos", Jan. 21, 2010, pp. 227-238, vol. 5, No. 2, Publisher: Nature Protocols.
Tanaka, et al., "The Structure of Rat Liver Vault at 3.5 Angstrom Resolution", Jan. 16, 2009, pp. 384-388, vol. 323, Publisher: Science.

(Continued)

*Primary Examiner* — Scott Long
(74) *Attorney, Agent, or Firm* — Suzannah K. Sundby, Esq.; Canady + Lortz LLP

(57) ABSTRACT

Disclosed herein are methods of making vaults and packaging one or more passenger molecules in the internal cavities of the vault particles using cell-free techniques. Vaults according to the present invention and compositions comprising the vaults are free of cellular debris.

16 Claims, 18 Drawing Sheets

Specification includes a Sequence Listing.

(56) References Cited

OTHER PUBLICATIONS

Tsuboi, et al., "The wheat germ cell-free protein synthesis system: A key tool for novel malaria vaccine candidate discovery", Nov. 11, 2009, pp. 171-176, vol. 114, Publisher: Acta Tropica.
Written Opinion received in PCT/US2015/051618 dated Dec. 28, 2015.
Yang, et al., "Vaults Are Dynamically Unconstrained Cytoplasmic Nanoparticles Capable of Half Vault Exchange", Dec. 1, 2010, pp. 7229-7240, vol. 4, No. 12, Publisher: ACS Nano.
Carlson, et al., "Cell-Free Protein Synthesis: Applications Come of Age", May 29, 2014, pp. 1185-1194, vol. 30, No. 5, Publisher: Biotechnol Adv.
Stephen, et al., "Assembly of Vault-like Particles in Insect Cells Expressing Only the Major Vault Protein", May 10, 2001, pp. 23217-23220, vol. 276, No. 26, Publisher: Journal of Biological Chemistry.
Yang, et al., "Vault Nanoparticles Engineered with the Protein Transduction Domain, TAT48, Enhances Cellular Uptake", Jan. 1, 2014, pp. 151-158, vol. 5, No. 1, Publisher: IntegrBiol (Camb).

\* cited by examiner

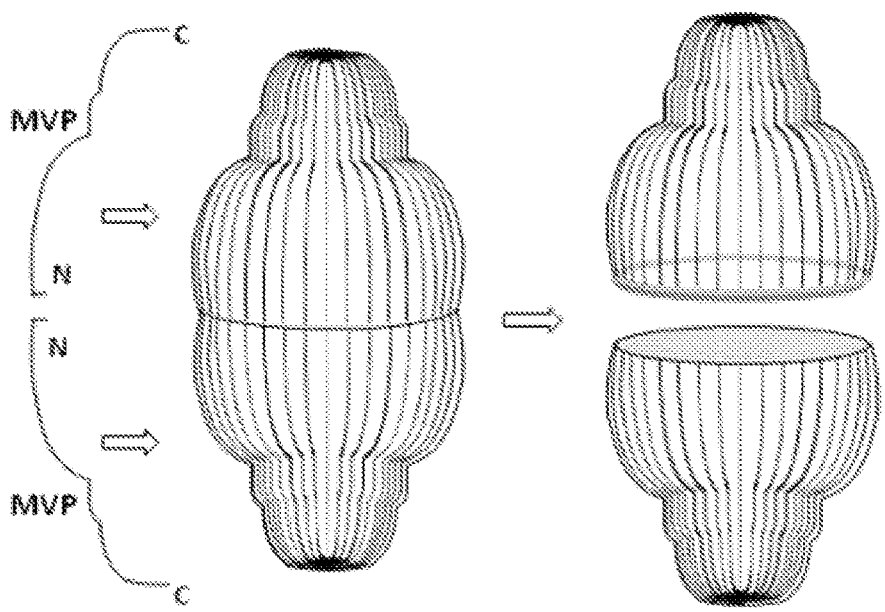

Figure 1A

| MVP modification | N-terminus |
|---|---|
| wt | MATEEAIIRIPPYHYIHVLD..... |
| 1His | MAHEEAIIRIPPYHYIHVLD..... |
| 2His | MAHHEAIIRIPPYHYIHVLD..... |
| 3His | MAHHHAIIRIPPYHYIHVLD..... |
| 4His | MAHHHHIIRIPPYHYIHVLD..... |
| 5His | MAHHHHHIRIPPYHYIHVLD..... |
| 6His | MAHHHHHHRIPPYHYIHVLD..... |

Figure 1B

| MVP | wild type | 1His | 2His | 3His | 4His | 5His | 6His |
|---|---|---|---|---|---|---|---|
| MVP Expression in Sf9 cells | ✓ | ✓ | ✓ | ✓ | ✓ | ✓ | ✓ |
| Stable vaults (UA staining) | ✓ | ✓ | ✓ | ✓ | ✓ | ✗ | ✗ |
| Unstable vaults (half vaults after UA staining) | ✗ | ✗ | ✗ | ✗ | ✓ | ✓ | ✗ |
| Unusual structural phenotype | ✗ | ✗ | ✗ | ✗ | ✗ | ✗ | ✓ |

Figure 1C pIVEX 1.3 Wheat Germ Expression Vector sequence

```
ATAAGGCGCAGCGGTCGGGCTGAACGGGGGGTTCGTGCACACAGCCCAGCTTGGAGCGAACGACCTACACCGAAC
TGAGATACCTACAGCGTGAGCTATGAGAAAGCGCCACGCTTCCCGAAGGGAGAAAGGCGGACAGGTATCCGGTAA
GCGGCAGGGTCGGAACAGGAGAGCGCACGAGGGAGCTTCCAGGGGAAACGCCTGGTATCTTTATAGTCCTGTCG
GGTTTCGCCACCTCTGACTTGAGCGTCGATTTTTGTGATGCTCGTCAGGGGGGCGGAGCCTATGGAAAAACGCCA
GCAACGCGGCCTTTTTACGGTTCCTGGCCTTTTGCTGGCCTTTTGCTCACATGTTCTTTCCTGCGTTATCCCCTG
ATTCTGTGGATAACCGTATTACCGCCTTTGAGTGAGCTGATACCGCTCGCCGCAGCCGAACGACCGAGCGCAGCG
AGTCAGTGAGCGAGGAAGCGGAAGAGCGCCCAATACGCAAACCGCCTCTCCCCGCGCGTTGGCCGATTCATTAAT
GCAGCTGGCACGACAGGTTTCCCGACTGGAAAGCGGGCAGTGAGCGCAACGCAATTAATGTGAGTTAGCTCACTC
ATTAGGCACCCCAGGCTTTACACTTTATGCTTCCGGCTCGTATGTTGTGTGGAATTGTGAGCGGATAACAATTTC
ACACAGGAAACAGCTATGACCATGATTACGCCAAGCTCATTAATACGACTCACTATAGGCCTAAGCTTACAAATA
CTCCCCCACAACAGCTTACAATACTCCCCCACACAGCTTACAAATACTCCCCCACAACAGCTTGTCGAACCATGG
CACATATGAGCGGCCGCGTCGACTCGAGCGAGCTCCCGGGGGGGTTCTCATCATCATCATCATCATTAATAAGG
TACCCAGCTCTTCTGGTTTGGTTTGGACCTCTGGTCCTGCAACTTGAGGTAGTCAAGATGCATAATAAATAACGG
ATTGTGTCCGTAATCACACGTGGTGCGTACGATAACGCATAGTGTTTTTCCCTCCACTTAAATCGAAGGGTTGTG
TCTTGGATCGCGCGGGTCAAATGTATATGGTTCATATACATCCGCAGGCACGTAATAAAGCGAGGGGTTCGAATC
CCCCCGTTACCCCCGGTAGGGGCCCATATATGCGGAATTCACTGGCCGTCGTTTTACAACGTCGTGACTGGGAAA
ACCCTGGCGTTACCCAACTTAATCGCCTTGCAGCACATCCCCTTTCGCCAGCTGGCGTAATAGCGAAGAGGCCC
GCACCGATCGCCCTTCCCAACAGTTGCGCAGCCTGAATGGCGAATGGAAATTGTAAGCGTTAATATTTTGTTAAA
ATTCGCGTTAAATTTTTGTTAAATCAGCTCATTTTTTAACCAATAGGCCGAAATCGGCAAAATCCCTTATAAATC
AAAAGAATAGACCGAGATAGGGTTGAGTGTTGTTCCAGTTTGGAACAAGAGTCCACTATTAAAGAACGTGGACTC
CAACGTCAAAGGGCGAAAAACCGTCTATCAGGGCGATGGCCCACTACGTGAACCATCACCCTAATCAAGTTTTTT
GGGGTCGAGGTGCCGTAAAGCACTAAATCGGAACCCTAAAGGGAGCCCCCGATTTAGAGCTTGACGGGGAAAGCC
GGCGAACGTGGCGAGAAAGGAAGGGAAGAAAGCGAAAGGAGCGGGCGCTAGGGCGCTGGCAAGTGTAGCGGTCAC
GCTGCGCGTAACCACCACACCCGCCGCGCTTAATGCGCCGCTACAGGGCGCGTCAGGTGGCACTTTTCGGGGAAA
TGTGCGCGGAACCCCTATTTGTTTATTTTTCTAAATACATTCAAATATGTATCCGCTCATGAGACAATAACCCTG
ATAAATGCTTCAATAATATTGAAAAAGGAAGAGTATGAGTATTCAACATTTCCGTGTCGCCCTTATTCCCTTTTT
TGCGGCATTTTGCCTTCCTGTTTTTGCTCACCCAGAAACGCTGGTGAAAGTAAAAGATGCTGAAGATCAGTTGGG
TGCACGAGTGGGTTACATCGAACTGGATCTCAACAGCGGTAAGATCCTTGAGAGTTTTCGCCCCGAAGAACGTTT
TCCAATGATGAGCACTTTTAAAGTTCTGCTATGTGGCGCGGTATTATCCCGTATTGACGCCGGGCAAGAGCAACT
CGGTCGCCGCATACACTATTCTCAGAATGACTTGGTTGAGTACTCACCAGTCACAGAAAAGCATCTTACGGATGG
CATGACAGTAAGAGAATTATGCAGTGCTGCCATAACCATGAGTGATAACACTGCGGCCAACTTACTTCTGACAAC
GATCGGAGGACCGAAGGAGCTAACCGCTTTTTGCACAACATGGGGGATCATGTAACTCGCCTTGATCGTTGGGA
ACCGGAGCTGAATGAAGCCATACCAAACGACGAGCGTGACACCACGATGCCTGTAGCAATGGCAACAACGTTGCG
CAAACTATTAACTGGCGAACTACTTACTCTAGCTTCCCGGCAACAATTAATAGACTGGATGGAGGCGGATAAAGT
TGCAGGACCACTTCTGCGCTCGGCCCTTCCGGCTGGCTGGTTTATTGCTGATAAATCTGGAGCCGGTGAGCGTGG
GTCTCGCGGTATCATTGCAGCACTGGGGCCAGATGGTAAGCCCTCCCGTATCGTAGTTATCTACACGACGGGGAG
TCAGGCAACTATGGATGAACGAAATAGACAGATCGCTGAGATAGGTGCCTCACTGATTAAGCATTGGTAACTGTC
AGACCAAGTTTACTCATATATACTTTAGATTGATTTAAAACTTCATTTTTAATTTAAAAGGATCTAGGTGAAGAT
CCTTTTTGATAATCTCATGACCAAAATCCCTTAACGTGAGTTTTCGTTCCACTGAGCGTCAGACCCCGTAGAAAA
GATCAAAGGATCTTCTTGAGATCCTTTTTTTCTGCGCGTAATCTGCTGCTTGCAAACAAAAAAACCACCGCTACC
AGCGGTGGTTTGTTTGCCGGATCAAGAGCTACCAACTCTTTTTCCGAAGGTAACTGGCTTCAGCAGAGCGCAGAT
ACCAAATACTGTCCTTCTAGTGTAGCCGTAGTTAGGCCACCACTTCAAGAACTCTGTAGCACCGCCTACATACCT
CGCTCTGCTAATCCTGTTACCAGTGGCTGCTGCCAGTGGCGATAAGTCGTGTCTTACCGGGTTGGACTCAAGACG
ATAGTTACCGG (SEQ ID NO: 8)
```

Figure 8A rMVP-pIVEX 1.3 sequence

```
ATAAGGCGCAGCGGTCGGGCTGAACGGGGGGTTCGTGCACACAGCCCAGCTTGGAGCGAACGACCTACACCGAAC
TGAGATACCTACAGCGTGAGCTATGAGAAAGCGCCACGCTTCCCGAAGGGAGAAAGGCGGACAGGTATCCGGTAA
GCGGCAGGGTCGGAACAGGAGAGCGCACGAGGGAGCTTCCAGGGGGAAACGCCTGGTATCTTTATAGTCCTGTCG
GGTTTCGCCACCTCTGACTTGAGCGTCGATTTTTGTGATGCTCGTCAGGGGGGCGGAGCCTATGGAAAAACGCCA
GCAACGCGGCCTTTTTACGGTTCCTGGCCTTTTGCTGGCCTTTTGCTCACATGTTCTTTCCTGCGTTATCCCCTG
ATTCTGTGGATAACCGTATTACCGCCTTTGAGTGAGCTGATACCGCTCGCCGCAGCCGAACGACCGAGCGCAGCG
AGTCAGTGAGCGAGGAAGCGGAAGAGCGCCCAATACGCAAACCGCCTCTCCCCGCGCGTTGGCCGATTCATTAAT
GCAGCTGGCACGACAGGTTTCCCGACTGGAAAGCGGGCAGTGAGCGCAACGCAATTAATGTGAGTTAGCTCACTC
ATTAGGCACCCCAGGCTTTACACTTTATGCTTCCGGCTCGTATGTTGTGTGGAATTGTGAGCGGATAACAATTTC
ACACAGGAAACAGCTATGACCATGATTACGCCAAGCTCATTAATACGACTCACTATAGGCCTAAGCTTACAAATA
CTCCCCCACAACAGCTTACAATACTCCCCACACAGCTTACAAATACTCCCCCACAACAGCTTGTCGAACCATGG
CAACTGAAGAGGCCATCATCCGCATCCCCCCATACCACTACATCCATGTGCTGGACCAGAACAGTAATGTGTCCC
GTGTGGAGGTTGGACCAAAGACCTACATCCGGCAGGACAATGAGAGGGTACTGTTTGCCCCAGTTCGCATGGTGA
CCGTCCCCCCACGCCACTACTGCATAGTGGCCAACCCTGTGTCCCGGGACACCCAGAGTTCTGTGTTATTTGACA
TCACAGGACAAGTCCGACTCCGGCACGCTGACCAGGAGATCCGACTAGCCCAGGACCCCTTCCCCCTGTATCCAG
GGGAGGTGCTGGAAAAGGACATCACCCCACTGCAGGTGGTTCTGCCCAACACAGCACTGCATCTTAAGGCGTTGC
TGGACTTTGAGGATAAGAATGGAGACAAGGTCATGGCAGGAGACGAGTGGCTATTTGAGGGACCTGGCACCTACA
TCCCACAGAAGGAAGTGGAAGTCGTGGAGATCATTCAGGCCACAGTCATCAAACAGAACCAAGCACTGCGGCTAA
GGGCCCGAAAGGAGTGCTTTGACCGGGAGGGCAAGGGGCGCGTGACAGGTGAGGAGTGGCTGGTCCGATCCGTGG
GGGCTTACCTCCCAGCTGTCTTTGAAGAGGTGCTGGATCTGGTGGATGCTGTGATCCTTACAGAAAAGACTGCCC
TGCACCTCCGGGCTCTGCAGAACTTCAGGGACCTTCGGGGAGTGCTCCACCGCACCGGGGAGGAATGGTTAGTGA
CAGTGCAGGACACAGAAGCCCATGTTCCAGATGTCTATGAGGAGGTGCTTGGGGTAGTACCCATCACCACCCTGG
GACCTCGACACTACTGTGTCATTCTTGACCCAATGGGACCAGACGGCAAGAACCAGCTGGGACAAAAGCGTGTTG
TCAAGGGAGAGAAGTCCTTTTTCCTCCAGCCAGGAGAGAGGCTGGAGCGAGGCATCCAGGATGTGTATGTGCTGT
CAGAGCAGCAGGGGCTGCTACTGAAGGCACTGCAGCCCCTGGAGGAGGGAGAGAGCGAGGAGAAGGTCTCCCATC
AGGCCGGAGACTGCTGGCTCATCCGTGGGCCCCTGGAGTATGTGCCATCTGCAAAAGTGGAGGTGGTGGAGGAGC
GTCAGGCTATCCCTCTGGACCAAAATGAGGGCATCTATGTGCAGGATGTCAAGACGGGGAAGGTGCGGGCTGTGA
TTGGAAGCACCTACATGCTGACTCAGGATGAAGTCCTGTGGGAAAAGGAGCTGCCTTCTGGGGTGGAGGAGCTGC
TGAACTTGGGGCATGACCCTCTGGCAGACAGGGGTCAGAAGGGCACAGCCAAGCCCCTTCAGCCCTCAGCTCCAA
GGAACAAGACCCGAGTGGTCAGCTACCGTGTCCCGCACAATGCAGCGGTGCAGGTCTATGACTACAGAGCCAAGA
GAGCCCGTGTGGTCTTTGGGCCCGAGCTAGTGACACTGGATCCTGAGGAGCAGTTCACAGTATTGTCCCTTTCTG
CCGGGCGACCCAAGCGTCCTCATGCCCGCCGTGCACTCTGCCTACTGCTGGGACCTGATTTCTTTACTGATGTCA
TCACCATCGAAACTGCAGATCATGCCAGGTTGCAGCTGCAGCTTGCCTACAACTGGCACTTTGAACTGAAGAACC
GGAATGACCCTGCAGAGGCAGCCAAGCTTTTCTCCGTGCCTGACTTCGTGGGTGACGCCTGCAAGGCCATTGCAT
CCCGAGTCCGGGGGGCTGTAGCCTCTGTCACCTTTGATGACTTCCATAAAAACTCAGCCCGGATCATTCGAATGG
CTGTTTTTGGCTTTGAGATGTCTGAAGACACAGGTCCTGATGGCACACTCCTGCCCAAGGCTCGAGACCAGGCAG
TCTTTCCCCAAAACGGGCTGGTAGTCAGCAGTGTGGATGTGCAGTCAGTGGAGCCCGTGGACCAGAGGACCCGGG
ATGCCCTTCAGCGCAGCGTTCAGCTGGCCATCGAAATTACCACCAACTCCCAGGAGGCAGCAGCCAAGCACGAGG
CTCAGAGACTGGAACAGGAAGCCCGTGGTCGGCTTGAGAGGCAGAAGATCTTGGACCAGTCAGAAGCTGAAAAAG
CCCGCAAGGAACTCTTGGAGCTTGAGGCTATGAGCATGGCTGTGGAGAGCACGGGTAATGCCAAAGCAGAGGCTG
AGTCCCGTGCAGAGGCAGCGAGGATCGAAGGAGAAGGCTCTGTGCTGCAGGCCAAGCTCAAGGCACAGGCGCTAG
CCATTGAGACGGAGGCTGAGTTGGAGCGAGTAAAGAAAGTACGAGAGATGGAACTGATCTATGCCCGGGCCCAGT
TGGAGCTGGAGGTGAGCAAGGCGCAGCAGCTTGCCAATGTGGAGGCAAAGAAGTTCAAGGAGATGACAGAGGCAC
TGGGCCCCGGCACCATCAGGGACCTGGCTGTGGCCGGGCCAGAGATGCAGGTGAAACTTCTCCAGTCCCTGGGCC
TGAAATCCACTCTCATCACCGATGGCTCGTCTCCCATCAACCTCTTCAGCACAGCCTTCGGGTTGCTGGGGCTGG
GGTCTGATGGTCAGCCGCCAGCACAGAAGTAATAAGGTACCCAGCTCTTCTGGTTTGGTTTGGACCTCTGGTCCT
GCAACTTGAGGTAGTCAAGATGCATAATAAATAACGGATTGTGTCCGTAATCACACGTGGTGCGTACGATAACGC
ATAGTGTTTTCCCTCCACTTAAATCGAAGGGTTGTGTCTTGGATCGCGCGGGTCAAATGTATATGGTTCATATA
CATCCGCAGGCACGTAATAAAGCGAGGGGTTCGAATCCCCCGTTACCCCCGGTAGGGCCCATATATGCGGAAT
TCACTGGCCGTCGTTTTACAACGTCGTGACTGGGAAAACCCTGGCGTTACCCAACTTAATCGCCTTGCAGCACAT
CCCCCTTTCGCCAGCTGGCGTAATAGCGAAGAGGCCCGCACCGATCGCCCTTCCCAACAGTTGCGCAGCCTGAAT
GGCGAATGGAAATTGTAAGCGTTAATATTTTGTTAAAATTCGCGTTAAATTTTTGTTAAATCAGCTCATTTTTA
ACCAATAGGCCGAAATCGGCAAAATCCCTTATAAATCAAAAGAATAGACCGAGATAGGGTTGAGTGTTGTTCCAG
TTTGGAACAAGAGTCCACTATTAAAGAACGTGGACTCCAACGTCAAAGGGCGAAAAACCGTCTATCAGGGCGATG
GCCCACTACGTGAACCATCACCCTAATCAAGTTTTTTGGGGTCGAGGTGCCGTAAAGCACTAAATCGGAACCCTA
AAGGGAGCCCCCGATTTAGAGCTTGACGGGGAAAGCCGGCGAACGTGGCGAGAAAGGAAGGGAAGAAAGCGAAAG
```

```
GAGCGGGCGCTAGGGCGCTGGCAAGTGTAGCGGTCACGCTGCGCGTAACCACCACACCCGCCGCGCTTAATGCGC
CGCTACAGGGCGCGTCAGGTGGCACTTTTCGGGGAAATGTGCGCGGAACCCCTATTTGTTTATTTTTCTAAATAC
ATTCAAATATGTATCCGCTCATGAGACAATAACCCTGATAAATGCTTCAATAATATTGAAAAAGGAAGAGTATGA
GTATTCAACATTTCCGTGTCGCCCTTATTCCCTTTTTTGCGGCATTTTGCCTTCCTGTTTTTGCTCACCCAGAAA
CGCTGGTGAAAGTAAAAGATGCTGAAGATCAGTTGGGTGCACGAGTGGGTTACATCGAACTGGATCTCAACAGCG
GTAAGATCCTTGAGAGTTTTCGCCCCGAAGAACGTTTTCCAATGATGAGCACTTTTAAAGTTCTGCTATGTGGCG
CGGTATTATCCCGTATTGACGCCGGGCAAGAGCAACTCGGTCGCCGCATACACTATTCTCAGAATGACTTGGTTG
AGTACTCACCAGTCACAGAAAAGCATCTTACGGATGGCATGACAGTAAGAGAATTATGCAGTGCTGCCATAACCA
TGAGTGATAACACTGCGGCCAACTTACTTCTGACAACGATCGGAGGACCGAAGGAGCTAACCGCTTTTTTGCACA
ACATGGGGGATCATGTAACTCGCCTTGATCGTTGGGAACCGGAGCTGAATGAAGCCATACCAAACGACGAGCGTG
ACACCACGATGCCTGTAGCAATGGCAACAACGTTGCGCAAACTATTAACTGGCGAACTACTTACTCTAGCTTCCC
GGCAACAATTAATAGACTGGATGGAGGCGGATAAAGTTGCAGGACCACTTCTGCGCTCGGCCCTTCCGGCTGGCT
GGTTTATTGCTGATAAATCTGGAGCCGGTGAGCGTGGGTCTCGCGGTATCATTGCAGCACTGGGGCCAGATGGTA
AGCCCTCCCGTATCGTAGTTATCTACACGACGGGGAGTCAGGCAACTATGGATGAACGAAATAGACAGATCGCTG
AGATAGGTGCCTCACTGATTAAGCATTGGTAACTGTCAGACCAAGTTTACTCATATATACTTTAGATTGATTTAA
AACTTCATTTTTAATTTAAAAGGATCTAGGTGAAGATCCTTTTTGATAATCTCATGACCAAAATCCCTTAACGTG
AGTTTTCGTTCCACTGAGCGTCAGACCCCGTAGAAAAGATCAAAGGATCTTCTTGAGATCCTTTTTTTCTGCGCG
TAATCTGCTGCTTGCAAACAAAAAAACCACCGCTACCAGCGGTGGTTTGTTTGCCGGATCAAGAGCTACCAACTC
TTTTTCCGAAGGTAACTGGCTTCAGCAGAGCGCAGATACCAAATACTGTCCTTCTAGTGTAGCCGTAGTTAGGCC
ACCACTTCAAGAACTCTGTAGCACCGCCTACATACCTCGCTCTGCTAATCCTGTTACCAGTGGCTGCTGCCAGTG
GCGATAAGTCGTGTCTTACCGGGTTGGACTCAAGACGATAGTTACCGG (SEQ ID NO: 9)
```

Figure 8B cont.

Linear Template for rMVP expression in wheat germ expression system

GGATAACAATTTCACACAGGAAACAGCTATGACCATGATTACGCCAAGCTCATTAATACGACTCACTATAGGCCT
AAGCTTACAAATACTCCCCCACAACAGCTTACAATACTCCCCCACACAGCTTACAAATACTCCCCCACAACAGCT
TGTCGAACCATGGCAACTGAAGAGGCCATCATCCGCATCCCCCCATACCACTACATCCATGTGCTGGACCAGAAC
AGTAATGTGTCCCGTGTGGAGGTTGGACCAAAGACCTACATCCGGCAGGACAATGAGAGGGTACTGTTTGCCCCA
GTTCGCATGGTGACCGTCCCCCCACGCCACTACTGCATAGTGGCCAACCCTGTGTCCCGGGACACCCAGAGTTCT
GTGTTATTTGACATCACAGGACAAGTCCGACTCCGGCACGCTGACCAGGAGATCCGACTAGCCCAGGACCCCTTC
CCCCTGTATCCAGGGGAGGTGCTGGAAAAGGACATCACCCCACTGCAGGTGGTTCTGCCCAACACAGCACTGCAT
CTTAAGGCGTTGCTGGACTTTGAGGATAAGAATGGAGACAAGGTCATGGCAGGAGACGAGTGGCTATTTGAGGGA
CCTGGCACCTACATCCCACAGAAGGAAGTGGAAGTCGTGGAGATCATTCAGGCCACAGTCATCAAACAGAACCAA
GCACTGCGGCTAAGGGCCCGAAAGGAGTGCTTTGACCGGGAGGGCAAGGGGCGCGTGACAGGTGAGGAGTGGCTG
GTCCGATCCGTGGGGGCTTACCTCCCAGCTGTCTTTGAAGAGGTGCTGGATCTGGTGGATGCTGTGATCCTTACA
GAAAAGACTGCCCTGCACCTCCGGGCTCTGCAGAACTTCAGGGACCTTCGGGGAGTGCTCCACCGCACCGGGGAG
GAATGGTTAGTGACAGTGCAGGACACAGAAGCCCATGTTCCAGATGTCTATGAGGAGGTGCTTGGGGTAGTACCC
ATCACCACCCTGGGACCTCGACACTACTGTGTCATTCTTGACCCAATGGGACCAGACGGCAAGAACCAGCTGGGA
CAAAAGCGTGTTGTCAAGGGAGAGAAGTCCTTTTTCCTCCAGCCAGGAGAGAGGCTGGAGCGAGGCATCCAGGAT
GTGTATGTGCTGTCAGAGCAGCAGGGGCTGCTACTGAAGGCACTGCAGCCCCTGGAGGAGGGAGAGAGCGAGGAG
AAGGTCTCCCATCAGGCCGGAGACTGCTGGCTCATCCGTGGGCCCCTGGAGTATGTGCCATCTGCAAAAGTGGAG
GTGGTGGAGGAGCGTCAGGCTATCCCTCTGGACCAAAATGAGGGCATCTATGTGCAGGATGTCAAGACGGGGAAG
GTGCGGGCTGTGATTGGAAGCACCTACATGCTGACTCAGGATGAAGTCCTGTGGGAAAAGGAGCTGCCTTCTGGG
GTGGAGGAGCTGCTGAACTTGGGGCATGACCCTCTGGCAGACAGGGGTCAGAAGGGCACAGCCAAGCCCCTTCAG
CCCTCAGCTCCAAGGAACAAGACCCGAGTGGTCAGCTACCGTGTCCCGCACAATGCAGCGGTGCAGGTCTATGAC
TACAGAGCCAAGAGAGCCCGTGTGGTCTTTGGGCCCGAGCTAGTGACACTGGATCCTGAGGAGCAGTTCACAGTA
TTGTCCCTTTCTGCCGGGCGACCCAAGCGTCCTCATGCCCGCCGTGCACTCTGCCTACTGCTGGGACCTGATTTC
TTTACTGATGTCATCACCATCGAAACTGCAGATCATGCCAGGTTGCAGCTGCAGCTTGCCTACAACTGGCACTTT
GAACTGAAGAACCGGAATGACCCTGCAGAGGCAGCCAAGCTTTTCTCCGTGCCTGACTTCGTGGGTGACGCCTGC
AAGGCCATTGCATCCCGAGTCCGGGGGGCTGTAGCCTCTGTCACCTTTGATGACTTCCATAAAAACTCAGCCCGG
ATCATTCGAATGGCTGTTTTTGGCTTTGAGATGTCTGAAGACACAGGTCCTGATGGCACACTCCTGCCCAAGGCT
CGAGACCAGGCAGTCTTTCCCCAAAACGGGCTGGTAGTCAGCAGTGTGGATGTGCAGTCAGTGGAGCCCGTGGAC
CAGAGGACCCGGGATGCCCTTCAGCGCAGCGTTCAGCTGGCCATCGAAATTACCACCAACTCCCAGGAGGCAGCA
GCCAAGCACGAGGCTCAGAGACTGGAACAGGAAGCCCGTGGTCGGCTTGAGAGGCAGAAGATCTTGGACCAGTCA
GAAGCTGAAAAAGCCCGCAAGGAACTCTTGGAGCTTGAGGCTATGAGCATGGCTGTGGAGAGCACGGGTAATGCC
AAAGCAGAGGCTGAGTCCCGTGCAGAGGCAGCGAGGATCGAAGGAGAAGGCTCTGTGCTGCAGGCCAAGCTCAAG
GCACAGGCGCTAGCCATTGAGACGGAGGCTGAGTTGGAGCGAGTAAAGAAAGTACGAGAGATGGAACTGATCTAT
GCCCGGGCCCAGTTGGAGCTGGAGGTGAGCAAGGCGCAGCAGCTTGCCAATGTGGAGGCAAAGAAGTTCAAGGAG
ATGACAGAGGCACTGGGCCCCGGCACCATCAGGGACCTGGCTGTGGCCGGGCCAGAGATGCAGGTGAAACTTCTC
CAGTCCCTGGGCCTGAAATCCACTCTCATCACCGATGGCTCGTCTCCCATCAACCTCTTCAGCACAGCCTTCGGG
TTGCTGGGGCTGGGGTCTGATGGTCAGCCGCCAGCACAGAAGTAATAAGGTACCCAGCTCTTCTGGTTTGGTTTG
GACCTCTGGTCCTGCAACTTGAGGTAGTCAAGATGCATAATAAATAACGGATTGTGTCCGTAATCACACGTGGTG
CGTACGATAACGCATAGTGTTTTTCCCTCCACTTAAATCGAAGGGTTGTGTCTTGGATCGCGCGGGTCAAATGTA
TATGGTTCATATACATCCGCAGGCACGTAATAAAGCGAGGGGTTCGAATCCCCCCGTTACCCCCGGTAGGGGCCC
ATATATGC (SEQ ID NO: 10)

Figure 8C

Linear Template (3021 bp) for rMVP mRNA transcription reaction

GGATAACAATTTCACACAGGAAACAGCTATGACCATGATTACGCCAAGCTCATTAATACGACTCACTATAGGCCT
AAGCTTACAAATACTCCCCCACAACAGCTTACAATACTCCCCCACACAGCTTACAAATACTCCCCCACAACAGCT
TGTCGAACCATGGCAACTGAAGAGGCCATCATCCGCATCCCCCCATACCACTACATCCATGTGCTGGACCAGAAC
AGTAATGTGTCCCGTGTGGAGGTTGGACCAAAGACCTACATCCGGCAGGACAATGAGAGGGTACTGTTTGCCCCA
GTTCGCATGGTGACCGTCCCCCCACGCCACTACTGCATAGTGGCCAACCCTGTGTCCCGGGACACCCAGAGTTCT
GTGTTATTTGACATCACAGGACAAGTCCGACTCCGGCACGCTGACCAGGAGATCCGACTAGCCCAGGACCCCTTC
CCCCTGTATCCAGGGGAGGTGCTGGAAAAGGACATCACCCCACTGCAGGTGGTTCTGCCCAACACAGCACTGCAT
CTTAAGGCGTTGCTGGACTTTGAGGATAAGAATGGAGACAAGGTCATGGCAGGAGACGAGTGGCTATTTGAGGGA
CCTGGCACCTACATCCCACAGAAGGAAGTGGAAGTCGTGGAGATCATTCAGGCCACAGTCATCAAACAGAACCAA
GCACTGCGGCTAAGGGCCCGAAAGGAGTGCTTTGACCGGGAGGGCAAGGGGCGCGTGACAGGTGAGGAGTGGCTG
GTCCGATCCGTGGGGGCTTACCTCCCAGCTGTCTTTGAAGAGGTGCTGGATCTGGTGGATGCTGTGATCCTTACA
GAAAAGACTGCCCTGCACCTCCGGGCTCTGCAGAACTTCAGGGACCTTCGGGGAGTGCTCCACCGCACCGGGGAG
GAATGGTTAGTGACAGTGCAGGACACAGAAGCCCATGTTCCAGATGTCTATGAGGAGGTGCTTGGGGTAGTACCC
ATCACCACCCTGGGACCTCGACACTACTGTGTCATTCTTGACCCAATGGGACCAGACGGCAAGAACCAGCTGGGA
CAAAAGCGTGTTGTCAAGGGAGAGAAGTCCTTTTTCCTCCAGCCAGGAGAGAGGCTGGAGCGAGGCATCCAGGAT
GTGTATGTGCTGTCAGAGCAGCAGGGGCTGCTACTGAAGGCACTGCAGCCCCTGGAGGAGGGAGAGAGCGAGGAG
AAGGTCTCCCATCAGGCCGGAGACTGCTGGCTCATCCGTGGGCCCTGGAGTATGTGCCATCTGCAAAAGTGGAG
GTGGTGGAGGAGCGTCAGGCTATCCCTCTGGACCAAAATGAGGGCATCTATGTGCAGGATGTCAAGACGGGGAAG
GTGCGGGCTGTGATTGGAAGCACCTACATGCTGACTCAGGATGAAGTCCTGTGGGAAAAGGAGCTGCCTTCTGGG
GTGGAGGAGCTGCTGAACTTGGGGCATGACCCTCTGGCAGACAGGGGTCAGAAGGGCACAGCCAAGCCCCTTCAG
CCCTCAGCTCCAAGGAACAAGACCCGAGTGGTCAGCTACCGTGTCCCGCACAATGCAGCGGTGCAGGTCTATGAC
TACAGAGCCAAGAGAGCCCGTGTGGTCTTTGGGCCCGAGCTAGTGACACTGGATCCTGAGGAGCAGTTCACAGTA
TTGTCCCTTTCTGCCGGGCGACCCAAGCGTCCTCATGCCCGCCGTGCACTCTGCCTACTGCTGGGACCTGATTTC
TTTACTGATGTCATCACCATCGAAACTGCAGATCATGCCAGGTTGCAGCTGCAGCTTGCCTACAACTGGCACTTT
GAACTGAAGAACCGGAATGACCCTGCAGAGGCAGCCAAGCTTTTCTCCGTGCCTGACTTCGTGGGTGACGCCTGC
AAGGCCATTGCATCCCGAGTCCGGGGGGCTGTAGCCTCTGTCACCTTTGATGACTTCCATAAAAACTCAGCCCGG
ATCATTCGAATGGCTGTTTTTGGCTTTGAGATGTCTGAAGACACAGGTCCTGATGGCACACTCCTGCCCAAGGCT
CGAGACCAGGCAGTCTTTCCCCAAAACGGGCTGGTAGTCAGCAGTGTGGATGTGCAGTCAGTGGAGCCCGTGGAC
CAGAGGACCCGGGATGCCCTTCAGCGCAGCGTTCAGCTGGCCATCGAAATTACCACCAACTCCCAGGAGGCAGCA
GCCAAGCACGAGGCTCAGAGACTGGAACAGGAAGCCCGTGGTCGGCTTGAGAGGCAGAAGATCTTGGACCAGTCA
GAAGCTGAAAAAGCCCGCAAGGAACTCTTGGAGCTTGAGGCTATGAGCATGGCTGTGGAGAGCACGGGTAATGCC
AAAGCAGAGGCTGAGTCCCGTGCAGAGGCAGCGAGGATCGAAGGAGAAGGCTCTGTGCTGCAGGCCAAGCTCAAG
GCACAGGCGCTAGCCATTGAGACGGAGGCTGAGTTGGAGCGAGTAAAGAAAGTACGAGAGATGGAACTGATCTAT
GCCCGGGCCCAGTTGGAGCTGGAGGTGAGCAAGGCGCAGCAGCTTGCCAATGTGGAGGCAAAGAAGTTCAAGGAG
ATGACAGAGGCACTGGGCCCCGGCACCATCAGGGACCTGGCTGTGGCCGGGCCAGAGATGCAGGTGAAACTTCTC
CAGTCCCTGGGCCTGAAATCCACTCTCATCACCGATGGCTCGTCTCCCATCAACCTCTTCAGCACAGCCTTCGGG
TTGCTGGGGCTGGGGTCTGATGGTCAGCCGCCAGCACAGAAGTAATAAGGTACCCAGCTCTTCTGGTTTGGTTTG
GACCTCTGGTCCTGCAACTTGAGGTAGTCAAGATGCATAATAAATAACGGATTGTGTCCGTAATCACACGTGGTG
CGTACGATAACGCATAGTGTTTTCCCTCCACTTAAATCGAAGGGTTGTGTCTTGGATCGCGCGGGTCAAATGTA
TATGGTTCATATACATCCGCAGGCACGTAATAAAGCGAGGGGTTCGAATCCCCCGTTACCCCGGTAGGGGCC̲
ATATATGCGGAATTCACTGGC (SEQ ID NO: 11)

Figure 8D ents, the synthesis mixture is an in vitro translation mixture. In some embodiments, the nucleic acid molecule is a vector containing a nucleotide sequence that encodes the major vault protein or an mRNA that encodes the major vault protein. In some embodiments, a nucleic acid molecule encodes a protein that consists essentially of or consists of

CELL-FREE METHODS OF PRODUCING VAULT PARTICLES AND VAULT PARTICLES RESULTING THEREFROM

REFERENCE TO A SEQUENCE LISTING SUBMITTED VIA EFS-WEB

The content of the ASCII text file of the sequence listing named "20150922_034044_151WO1_seq_ST25" which is 40.7 kb in size was created on Sep. 22, 2015, and electronically submitted via EFS-Web herewith the application is incorporated herein by reference in its entirety.

BACKGROUND OF THE INVENTION

1. Field of the Invention

The present invention generally relates to engineered vaults that are free of cellular debris, methods of making the engineered vaults, and methods of packaging passenger molecules in the engineered vaults.

2. Description of the Related Art

Vaults are cytoplasmic ubiquitous ribonucleoprotein particles first described in 1986 that are found in most eukaryotic cells. See Kedersha & Rome (1986) J Cell Biol 103(3): 699-709. Native vaults are about 12.9±1 MDa ovoid spheres with overall dimensions of about 72 nm×42 nm×42 nm. Vaults have been recombinantly produced using a baculovirus expression system and heterologous proteins have been encapsulated therein as fusion proteins, i.e., heterologous proteins recombinantly fused to the major vault protein interaction domain (mINT) of vault polyADP-ribose polymerase (VPARP). See Stephen, et al. (2001) J Biol Chem 276(26):23217-23220, and Kickhoefer, et al. (2005) PNAS USA 102(12):4348-4352. Specifically, empty vaults are recombinantly produced using Sf9 insect cells and a baculovirus vector and then the empty vaults are mixed with passenger-mINT fusion proteins (passenger molecules recombinantly fused to mINT), whereby the passenger-mINT fusion proteins become localized inside the vaults.

Unfortunately, the prior art methods of making vaults and packaging passenger molecules inside of the vaults have several drawbacks. First, the use of Sf9 insect cells and viral vectors to make the empty vaults results in contaminating proteins, e.g., viral vector contaminants such as baculovirus proteins, which are difficult, if not impossible to separate from vaults. These contaminant proteins may result in adverse or undesired immunogenic reactions when administered to a subject and/or interfere with the activity or function of the passenger molecules. Second, not all molecules, e.g., nucleic acid molecules, small molecules, etc., can be recombinantly fused to mINT. Thus, not all molecules can be packaged inside of vaults using the INT-fusion method. In fact, some proteins, e.g., the small (67 amino acid) peptide HIV-1 Gag 148-214, do not package efficiently, if at all, using INT-fusion method.

Therefore, a need exists for methods of making empty vaults that are free of contaminant proteins and methods of packaging a variety of passenger molecules, including molecules that cannot be recombinantly fused to mINT inside the vaults.

SUMMARY OF THE INVENTION

In some embodiments, the present invention provides cell-free methods of making a vault structure which comprise adding a nucleic acid molecule that encodes a major vault protein to a synthesis mixture, and incubating the resulting mixture to form the vault structure. In some embodiments, the present invention provides cell-free methods of making a vault structure which comprise adding a nucleic acid molecule that encodes a major vault protein to a synthesis mixture, and performing in vitro translation by incubating the resulting mixture to form the vault structure. In some embodiments, the in vitro translation is performed in continuous mode. In some embodiments, the vault structure is an engineered vault, a vault roll, or a vault half. In some embodiments, the vault structure is an engineered vault. In some embodiments, the synthesis mixture is free of cells. In some embodiments, the synthesis mixture is an in vitro transcription-translation mixture. In some embodiments, the synthesis mixture is an in vitro translation mixture. In some embodiments, the nucleic acid molecule is a vector containing a nucleotide sequence that encodes the major vault protein or an mRNA that encodes the major vault protein. In some embodiments, a nucleic acid molecule encodes a protein that consists essentially of or consists of an MVP protein. In some embodiments, the major vault protein has 90-100% sequence identity to rat, mouse, or human major vault protein. In some embodiments, the major vault protein has 95-100% sequence identity to rat, mouse, or human major vault protein. In some embodiments, the major vault protein is rat, mouse, or human major vault protein. In some embodiments, the methods further comprise providing one or more passenger molecules in the synthesis mixture during the incubating step. In some embodiments, the methods further comprise adding one or more passenger molecules to the synthesis mixture before, during, and/or after the vault structure is formed. In some embodiments, the one or more passenger molecules are selected from the group consisting of nucleic acid molecules, proteins, amino acids, modified amino acids, lipids, glycolipids, polysaccharides, sterols, vitamins, hormones, small molecules, and combinations thereof. In some embodiments, at least one of the one or more passenger molecules cannot be packaged into vault particles using an INT-fusion method. In some embodiments, at least one of the one or more passenger molecules is not fused to a mINT sequence. In some embodiments, at least one of the one or more passenger molecules is recombinantly fused to a mINT sequence. In some embodiments, at least one of the one or more passenger molecules cannot be packaged into vault particles using an INT-fusion method, and at least one of the one or more passenger molecules is recombinantly fused to a mINT sequence.

In some embodiments, the present invention provides vault structures made by a method according to the present invention. In some embodiments, the vault structure is made by adding a nucleic acid molecule that encodes a major vault protein to a synthesis mixture, and incubating the resulting mixture to form the vault structure. In some embodiments, the vault structure is made by adding a nucleic acid molecule that encodes a major vault protein to a synthesis mixture, and performing in vitro translation by incubating the resulting mixture to form the vault structure. In some embodiments, the in vitro translation is performed in continuous mode. In some embodiments, the synthesis mixture is free of cells. In some embodiments, the synthesis mixture is an in vitro transcription-translation mixture. In some embodim an MVP protein. In some embodiments, the major vault protein has 90-100% sequence identity to rat, mouse, or human major vault protein. In some embodiments, the major vault protein has 95-100% sequence identity to rat, mouse, or human major vault protein. In some embodiments, the major vault protein is rat, mouse, or human major vault protein. In some embodiments, the methods further comprise providing one or more passenger molecules in the synthesis mixture during the incubating step. In some embodiments, the methods further comprise adding one or more passenger molecules to the synthesis mixture before, during, and/or after the vault structure is formed. In some embodiments, the one or more passenger molecules are selected from the group consisting of nucleic acid molecules, proteins, amino acids, modified amino acids, lipids, glycolipids, polysaccharides, sterols, vitamins, hormones, small molecules, and combinations thereof. In some embodiments, at least one of the one or more passenger molecules cannot be packaged into vault particles using an INT-fusion method. In some embodiments, at least one of the one or more passenger molecules is not fused to a mINT sequence. In some embodiments, at least one of the one or more passenger molecules is recombinantly fused to a mINT sequence. In some embodiments, at least one of the one or more passenger molecules cannot be packaged into vault particles using an INT-fusion method, and at least one of the one or more passenger molecules is recombinantly fused to a mINT sequence. In some embodiments, the vault structure is an engineered vault, a vault roll, or a vault half.

In some embodiments, the present invention provides an engineered vault made by a method according to the present invention. In some embodiments, the engineered vault is made by adding a nucleic acid sequence that encodes a major vault protein to a synthesis mixture, and incubating the resulting mixture to form the engineered vault. In some embodiments, the engineered vault is made by adding a nucleic acid molecule that encodes a major vault protein to a synthesis mixture, and performing in vitro translation by incubating the resulting mixture to form the vault structure. In some embodiments, the in vitro translation is performed in continuous mode. In some embodiments, the synthesis mixture is free of cells. In some embodiments, the synthesis mixture is an in vitro transcription-translation mixture. In some embodiments, the synthesis mixture is an in vitro translation mixture. In some embodiments, the nucleic acid molecule is a vector containing a nucleotide sequence that encodes the major vault protein or an mRNA that encodes the major vault protein. In some embodiments, a nucleic acid molecule encodes a protein that consists essentially of or consists of an MVP protein. In some embodiments, the major vault protein has 90-100% sequence identity to rat, mouse, or human major vault protein. In some embodiments, the major vault protein has 95-100% sequence identity to rat, mouse, or human major vault protein. In some embodiments, the major vault protein is rat, mouse, or human major vault protein. In some embodiments, the methods further comprise providing one or more passenger molecules in the synthesis mixture during the incubating step. In some embodiments, the methods further comprise adding one or more passenger molecules to the synthesis mixture before, during, and/or after the engineered vault is formed. In some embodiments, the engineered vault further comprises one or more passenger molecules packaged in its internal cavity. In some embodiments, at least two different types of passenger molecules are packaged into the internal cavity of the engineered vault. In some embodiments, the one or more passenger molecules are selected from the group consisting of nucleic acid molecules, proteins, amino acids, modified amino acids, lipids, glycolipids, polysaccharides, sterols, vitamins, hormones, small molecules, and combinations thereof. In some embodiments, at least one of the one or more passenger molecules cannot be packaged into vault particles using an INT-fusion method. In some embodiments, at least one of the one or more passenger molecules is not fused to a mINT sequence. In some embodiments, at least one of the one or more passenger molecules is recombinantly fused to a mINT sequence. In some embodiments, at least one of the one or more passenger molecules cannot be packaged into vault particles using an INT-fusion method, and at least one of the one or more passenger molecules is recombinantly fused to a mINT sequence. In some embodiments, the engineered vaults are free of cellular debris.

In some embodiments, the present invention is directed to a composition comprising one or more vault structures selected from those made by the methods according to the present invention and/or the engineered vaults according to the present invention. In some embodiments, the composition comprises a mixture of two or more different types of vault structures selected from those made by the methods according to the present invention and the engineered vaults according to the present invention. In some embodiments, the composition comprises at least one engineered vault having one or more passenger molecules packaged in its internal cavity. In some embodiments, at least two different types of passenger molecules are packaged into the internal cavity of the engineered vault. In some embodiments, the one or more passenger molecules are selected from the group consisting of nucleic acid molecules, proteins, amino acids, modified amino acids, lipids, glycolipids, polysaccharides, sterols, vitamins, hormones, small molecules, and combinations thereof. In some embodiments, at least one of the one or more passenger molecules cannot be packaged into vault particles using an INT-fusion method. In some embodiments, at least one of the one or more passenger molecules is not fused to a mINT sequence. In some embodiments, at least one of the one or more passenger molecules is recombinantly fused to a mINT sequence. In some embodiments, at least one of the one or more passenger molecules cannot be packaged into vault particles using an INT-fusion method, and at least one of the one or more passenger molecules is recombinantly fused to a mINT sequence. In some embodiments, the composition is free of cells, free of cellular debris, or both.

In some embodiments, the present invention provides a vault structure formed of a mutated major vault protein, wherein the vault structure is a vault roll or a vault half. In some embodiments, the present invention provides a composition comprising one or more vault structure formed of a mutated major vault protein, wherein the vault structure is a vault roll or a vault half.

Both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention, and together with the description serve to explain the principles of the invention.

DESCRIPTION OF THE DRAWINGS

This invention is further understood by reference to the drawings wherein:

FIGS. 1A-1C summarize the systematic mutagenesis of the vault structure. The rat MVP N-terminus was systematically modified by substitution with histidine residues at residues 3-8 by PCR. FIG. 1A schematically shows the MVP configuration within the vault structure. FIG. 1B shows the sequences of the MVP N-terminal modifications. The sequences from top to bottom are SEQ ID NOs: 1-7. FIG. 1C summarizes the outcome of the structure based mutagenesis. Check marks=positive, x's=negative.

FIG. 5A is an electron micrograph of in vitro synthesized vaults. Samples were negatively stained with uranyl acetate. FIG. 5B schematically shows the differential centrifugation experiment. FIG. 5C is the Western blot of S20, S100, and P100 fractions from the differential centrifugation.

FIG. 8A is the sequence of the pIVEX 1.3 Wheat Germ Expression Vector sequence (SEQ ID NO: 8).

FIG. 8B is the sequence of the rMVP-pIVEX vector sequence (SEQ ID NO: 9). The bold nucleotides are the rMVP sequence and the start (ATG) and stop (TAA) codons are underlined. The rMVP sequence was cloned within the NcoI and KpnI site of the pIVEX 1.3 wheat germ expression vector.

FIG. 8C is the sequence of the linear template for expression of rMVP in the wheat germ expression system (SEQ ID NO: 10). The bold nucleotides are the rMVP sequence, the start (ATG) and stop (TAA) codons are underlined, and the double underlined nucleotides are the forward and reverse PCR primers used to generate the linear template from the rMVP-pIVEX vector.

FIG. 8D is the sequence of the linear template for expression of rMVP mRNA transcription reaction. The bold nucleotides are the rMVP sequence, the start (ATG) and stop (TAA) codons are underlined, and the double underlined nucleotides are the forward and reverse PCR primers used to generate the linear template from the rMVP-pIVEX vector. SEQ ID NO: 11).

DETAILED DESCRIPTION OF THE INVENTION

Figure 2:
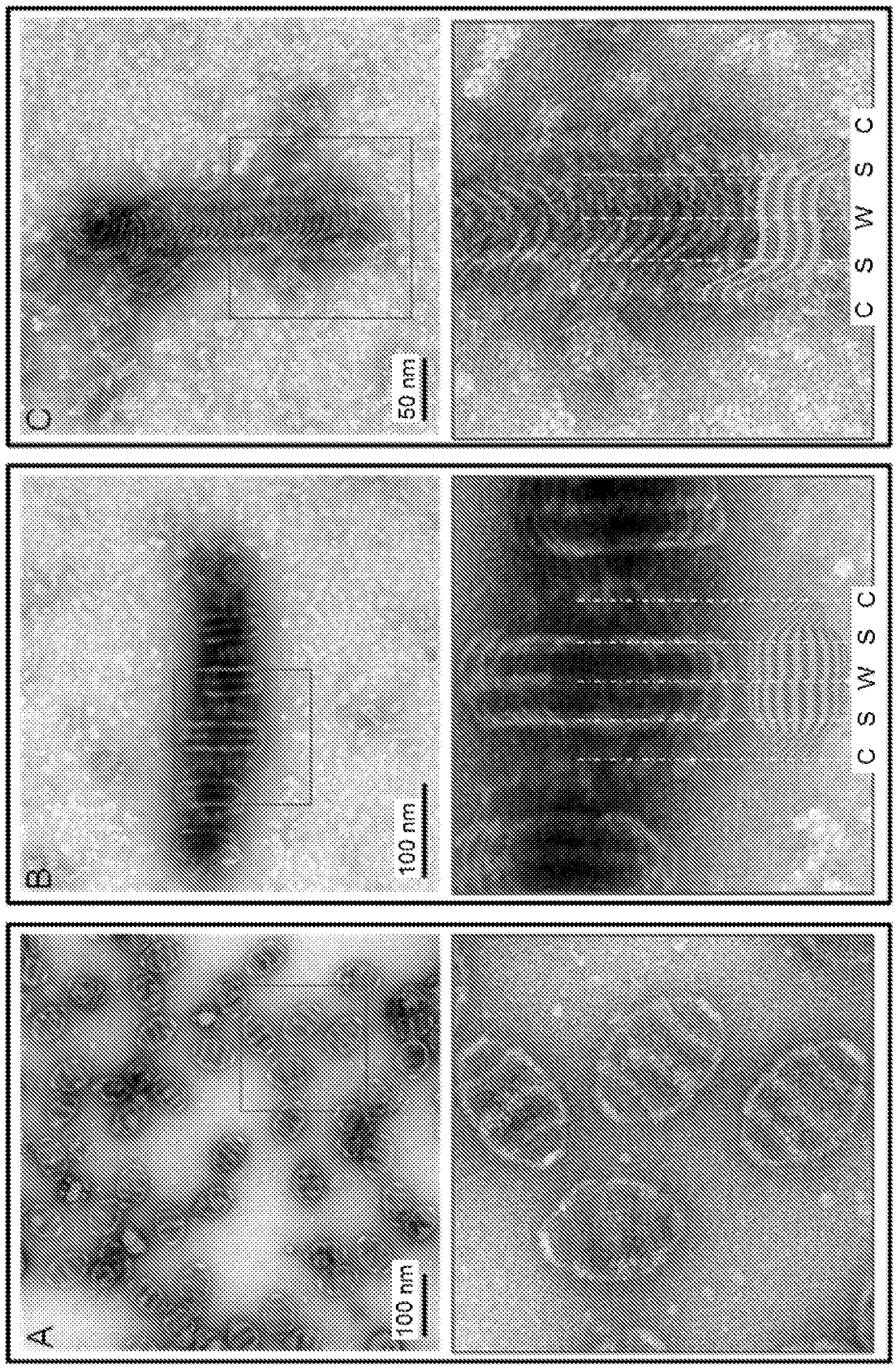
FIG. 2 provides representative structures of the 6-His-MVP mutant. Electron micrographs of uranyl acetate stained supernatants from infected Sf9 cells. Panel A is a micrograph of wild type MVP vaults with a close-up view from its insert (box) directly below. Panel B is a micrograph of staggered rolls of MVP chains and its insert (box), which is a close-up view of the rolls aligned with a representative crystal structure of the vault particle, directly below. The vault cap (C), shoulder (S), and waist (W) regions are indicated by white dashed lines. Panel C is a micrograph of a long sheet of an unraveled MVP roll and its insert (box), which is a close-up view of the sheet superimposed with several individual MVP chains from the crystal structure, directly below.

A vault comprises multiple copies of a major vault protein (MVP), tightly arranged to form the capsule-like shell of the particle. Each MVP chain is symmetrically arranged with the N-terminus at the waist of the particle and the C-terminus at the cap as shown in FIG. 1A. Inside the shell of naturally occurring vaults are multiple copies of VPARP proteins and TEP1 proteins and multiple copies of one or more small vault RNAs (vRNAs) may also be present in native vaults.

The present invention provides engineered vaults that are free of cells and cellular debris and methods of making thereof. The present invention also provides engineered vaults, which are free of cellular debris, having one or more passenger molecules packaged within the internal cavities of the engineered vaults and methods of making thereof.

As used herein, the terms "vault" and "vault particle" are used interchangeably to refer to a ribonucleoprotein (RNP) comprising complexes of MVP proteins, alone or in combination with VPARP proteins and/or TEP1 proteins, formed into a macromolecular structure having an ovoid shape with an internal cavity.

As used herein, "engineered vaults" and "engineered vault particles" are used interchangeably to refer to vaults that have been synthesized using laboratory techniques, e.g., recombinant methods, as opposed to naturally occurring vaults.

As used herein, an "MVP protein" refers to a protein that has 90-100%, preferably 95-100%, sequence identity to a major vault protein and is capable of forming a part of a vault. Examples of major vault proteins are provided in the NCBI protein database (available on the Internet, ncbi.nlm.nih.gov/protein) and include GI: 41055865 (rat), GI: 239052674 (mouse), and GI: 15990478 (human). MVP proteins can be synthetic, mutated, modified, human, animal (e.g., rat MVP), etc.

As used herein, a "VPARP protein" refers to a protein that has 90-100%, preferably 95-100%, sequence identity to a vault poly ADP-ribose polymerase and is capable of forming a part of a vault. Examples of VPARP proteins are provided in the NCBI protein database (available on the Internet, ncbi.nlm.nih.gov/protein) and include GI: 149064059 (rat), GI: 281485553 (mouse), and GI: 112789550 (human). VPARP proteins can be synthetic, mutated, modified, human, animal (e.g., rat VPARP), etc.

As used herein, an "mINT sequence" refers to the major vault protein interaction domain (mINT) of a VPARP protein.

As used herein, a "TEP1 protein" refers to a protein that has 90-100%, preferably 95-100%, sequence identity to a telomerase/vault associated protein 1 and is capable of forming a part of a vault. Examples of TEP1 proteins are provided in the NCBI protein database (available on the Internet, ncbi.nlm.nih.gov/protein) and include GI: 12018250 (rat), GI: 6678285 (mouse), and GI: 21536371 (human). TEP1 proteins can be synthetic, mutated, modified, human, animal (e.g., rat TEP1), etc.

As used herein, "cellular debris" refers to contaminants found on, in, and/or integrated within vaults that result from using cell-based expression systems. Such contaminants include proteins, nucleic acid molecules, lipids, carbohydrates, contaminants resulting from viral expression systems, and the like, and fragments thereof. As used herein, "cellular debris" excludes cellular-based molecules that result from using cell-free techniques.

As used herein, a "cell-based expression system" refers to the combination of an expression vector containing a nucleic acid molecule of interest to be expressed and a host cell, e.g., a bacterial, yeast, or insect cell, that enables the expression of the nucleic acid molecule when contained therein. An example of a cell-based expression system for producing vaults is provided in Stephen, et al. (2001) J Biol Chem 276: 23217-23220.

As used herein, "cell-free techniques" refers to methods for the cell-free expression of proteins that are performed in vitro using purified RNA polymerase, ribosomes, tRNA, and ribonucleotides, that are extracted from cells, recombinantly produced, or obtained from commercially available cell-free expression kits such as the IVT kits available from ThermoFisher Scientific (e.g., Catalog #'s AM1200, 88881, 88890, 88893) (Waltham, Mass.); PURExpress® In Vitro Protein Synthesis Kit (New England Biolabs, Inc., Ipswich, Mass.); TnT® SP6 High-Yield Wheat Germ Protein Expression System and TnT® T7 Insect Cell Extract Protein Expression System (Promega, Madison, Wis.); EasyXpress Insect Kit II (Qiagen, Valencia, Calif.); WEPRO®7240 Expression Kit (CellFree Sciences, Yokohama, Japan); RTS 100 Wheat Germ CECF Kit (Biotechrabbit, Hennigsdorf, Germany), and Human Cell-Free Protein Expression System (Cat. #3281) from Takara Bio Inc. (sold by Clontech Laboratories, Inc. Mountain View, Calif.). Cell-free techniques include in vitro transcription and in vitro translation. Methods for making reagents for use in cell-free expression systems and performing in vitro transcription and in vitro translation are known in the art. See, e.g., Zubay (1973) Ann. Rev. Gen. 7:267-287, Kigawa, et al. (1999) FEBS Letters 442:15-19, Kigawa, et al. (2004) J. of Struc. & Funct. Gen. 5:63-68, and Kim, et al. (2006) J. Biotechnol. 124(2):373-380. See also Endo & Sawasaki (2006) Curr Opin Biotechnol 17(4): 373-80; Harbers (2014) FEBS Letters 588(17): 2762-2773; Takai, et al. (2010) Nat Protoc 5(2): 227-238; Tsuboi, et al. (2010) Acta Trop 114(3): 171-176; Shirokov, et al. Methods Mol Biol 375: 19-55; and Park, et al. (2009) Nature Protocols 4: 1759-1770. In vitro transcription and in vitro translation can be performed in batch reactions or in a continuous mode such as dialysis and filter-feed methods known in the art.

As used herein, a "synthesis mixture" collectively refers to in vitro transcription-translation mixtures and in vitro translation mixtures. As used herein, an "in vitro transcription-translation mixture" refers to a mixture of reagents for in vitro transcription and translation, said reagents include an RNA polymerase (e.g., T7, SP6, etc.), nucleotide triphosphates (ATP, GTP, UTP, andCTP), one or more salts such as magnesium acetate, potassium acetate, and disodium creatine phosphate tetrahydrate, a polyamine such as spermidine, a buffer such as HEPES-KOH, a reducing agent such as dithiothreitol, an RNase inhibitor, amino acids, ribosomes, tRNAs, and creatine kinase. As used herein, an "in vitro translation mixture" refers to a mixture of reagents for in vitro translation, said reagents include the nucleotide triphosphates ATP and GTP, one or more salts such as magnesium acetate, potassium acetate, and disodium creatine phosphate tetrahydrate, a polyamine such as spermidine, a buffer such as HEPES-KOH, a reducing agent such as dithiothreitol, an RNase inhibitor, amino acids, ribosomes, tRNAs, and creatine kinase. In some embodiments of the present invention, the cell-free techniques employ an in vitro transcription-translation mixture when a DNA expression vector is used as the nucleic acid molecule that encodes an MVP protein. In some embodiments of the present invention, the cell-free techniques employ an in vitro translation mixture when an mRNA encoding the MVP protein is used as the nucleic acid molecule that encodes the MVP protein.

As used herein, "passenger molecules" refer to molecules of interest that are carried on the surface of vault particles, molecules enclosed in vault particles (e.g., when vault particles are fully closed), molecules contained within the cavities of vault particles (e.g., when vault particles have openings or are partially formed), and molecules incorporated in the structures of vaults (e.g., fused or linked to the major vault proteins of vaults).

As used herein, "mINT fusion packaging" refers to the packaging method where passenger molecules are recombinantly fused to mINT sequence and then the fusion molecules are mixed with formed vaults to thereby package the fusion molecules in the interior cavities of vaults as exemplified in US 20120213809.

As used herein, "percent sequence identity" refers to the percentage of nucleotides or amino acid residues that are the same between two sequences when aligned for maximum correspondence using methods known in the art.

As disclosed herein, after discovering polyribosome templating of vaults, cell-free techniques were used to produce engineered vaults that are free of cellular debris.

Polyribosome Templating and Cell-Free Production

Capturing Assembly Intermediates of Vault by Structure-Based Mutagenesis

An MVP protein (rat MVP) was recombinantly engineered to include peptide extensions in an attempt to determine how MVP proteins assemble into vaults. MVP proteins modified with N-terminal tags (ranging from 11 to 238 amino acids) assemble into vaults, but how the extra and potentially flexible N-terminal peptides all end up inside the particle at the waist was not fully understood.

Since analysis of crystal structures of vaults revealed that the two identical halves are connected with each other at the waist via antiparallel β sheet interactions that form between the first 4 N-terminal amino acids, constructs encoding a series of histidine substitutions for amino acids at positions three through eight of MVP were constructed (FIG. 1B) and their protein products were expressed using a cell-based expression system and conditions suitable for expression of vaults that have unmodified MVP. As summarized in FIG. 1C, substitution with one to three histidine residues (positions 3-5) did not alter the formation of vaults as the particles appeared similar to vaults having wild-type MVP (FIG. 2, Panel A), substitution with four and five histidine residues (positions 3-7) resulted in unstable vault particles that appeared to separate into halves after assembly, and substitution with six histidine residues (positions 3-8, "6-His MVP mutant") completely disrupted vault assembly. Interestingly, the 6-His MVP mutant resulted in unusually large structures that were predominantly staggered "rolls" (FIG. 2, Panel B) and some "sheets" (FIG. 2, Panel C) that appear to be rolls that became unraveled during the negative stain EM preparation. These large MVP rolls suggest that the 6-His MVP mutant generates a structure that represents a vault assembly intermediate, rather than just a chaotically misassembled swirl of protein.

Three prominent white bands are seen on each MVP roll (FIG. 2, Panel B). The distances between these bands are remarkably similar to the distance from the vault waist to the shoulder region, while the vault cap appears to be unstructured. This is shown in FIG. 2, Panel B, which aligns a portion of a "roll" with crystal structure of a vault. The structures shown in FIG. 2, Panel C, appear to be the inside of an unrolled sheet of MVP chains with their C-termini emanating from the sides of the sheet in a disordered manner as exemplified by the superimposed MVP chains.

Figure 3:
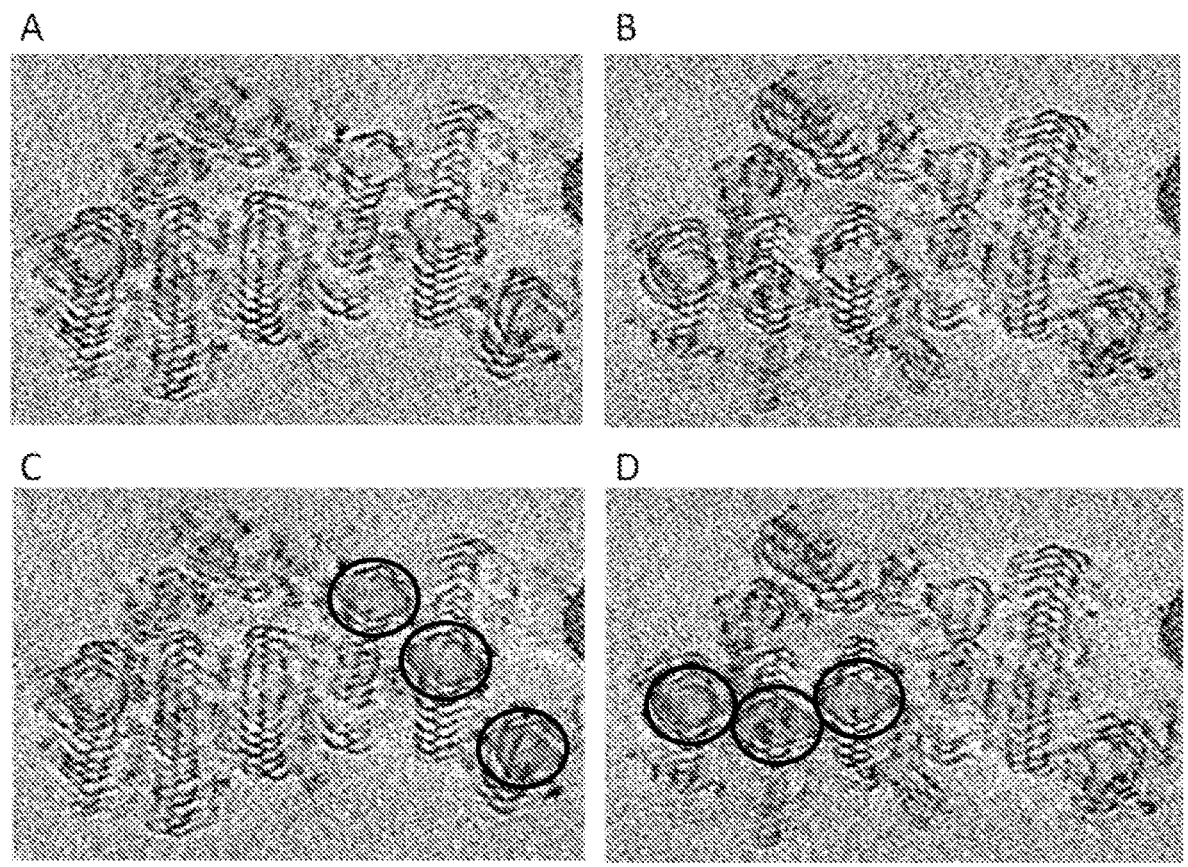
FIG. 3, Panels A-D, show cryo-electron tomography (cryo-ET) of 6-His MVP mutant rolled structures. Panels A and B show two frames from a cryo-ET cut series (Movie S1, see HyperTextTransferProtocol://vaults.arc2.ucla.edu/MovieS1DOThtm, wherein "HyperTextTransferProtocol" is "http" and "DOT" is ".") corresponding to different sample depths through a multiple 6-His-MVP roll. Panels C and D show vault particles (which are circled) superimposed over the center of rolls shown in Panels A and B, respectively.

To confirm this observation, cryo-electron tomography (cryo-ET) analysis of the vault assembly intermediate from the 6-His MVP mutant was performed. The 3D tomogram showed that each roll of the 6-His MVP was centered on a vault-like core structure (FIG. 3, Panels C and D). The sheets that form from the 6-His MVP mutant indicated that the sequence at the MVP N-terminus is important for the vault maturation since the 6-His MVP mutant results in a continuously formed sheet of MVP polypeptide chains giving rise to roll-like structures that do not mature into vault particles. As used herein, "vault structures" refers to engineered vaults, vault rolls, and vault halves.

Therefore, in some embodiments, the present invention provides vault rolls (i.e., rolled structures of MVP proteins), vault halves, and mixtures thereof. In some embodiments, the present invention provides methods of making vault rolls, vault halves, and mixtures thereof, which methods comprise disrupting the antiparallel β sheet interactions that normally form between the N-terminal amino acids of wild-type MVP proteins. In some embodiments, the disruption is by way of amino acid substitutions. In some embodiments, amino acid residues at positions 3-7 are substituted. In some embodiments, amino acid residues at positions 3-8 are substituted. In some embodiments, one or more of the amino acid residues that are substituted with histidine.

Polyribosome Templating for Vault Assembly

Figure 4:
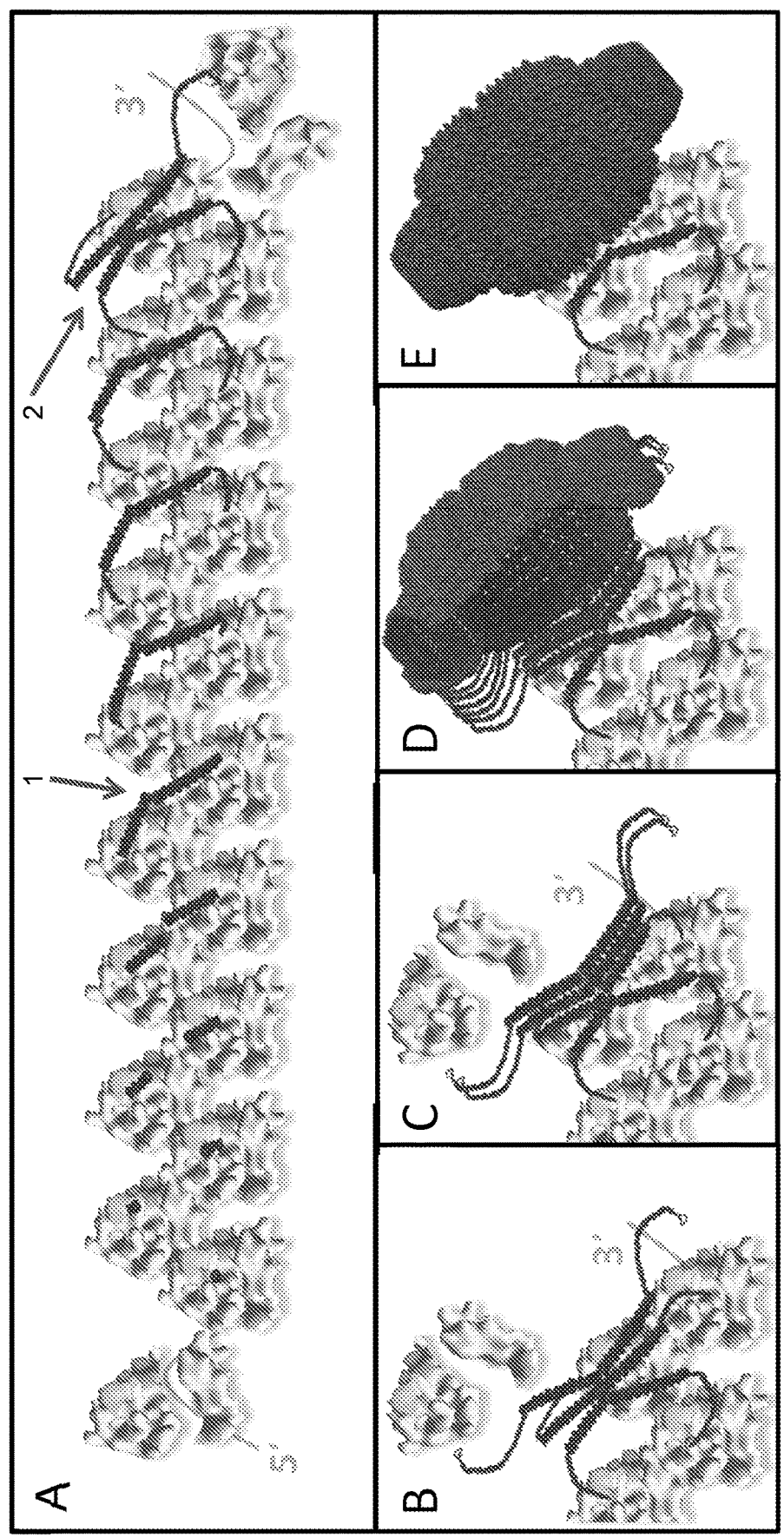
FIG. 4, Panels A-E schematically show vault assembly by polyribosome templating. Panel A is a schematic representation of a fully-assembled polyribosome; as translation continues MVP chains emerge, when two opposing MVP chains are long enough (arrow 1) the N-termini interact to form a dimer, as translation of the MVP dimers near completion, side-to-side interactions between neighboring MVP dimers begin to occur to give rise to MVP tetramer (arrow 2). These side-to-side interactions of sequentially incoming MVP dimers begin to form a sheet (Panels B-C), initiating the vault body to take its unique structure (Panel D). Once 39 MVP dimers emerge, a pinch-off event occurs, leading to formation of an intact vault particle (Panel E). All components of the model (MVP, vaults and the 80S ribosome were drawn to scale.

By combining the observed 6-His MVP structural phenotype with polyribosome geometry, a model of vault assembly was formulated as a co-translational process that is spatially constrained on a cytoplasmic polyribosome (FIG. 4).

In this model, referred to herein as "polyribosome templating", a single polyribosome acts like a cellular 3D nanoprinter. Progressively growing, neighboring MVP proteins interact with each other on a polyribosome with their N-termini to form a dimer. This MVP dimer then interacts with another adjacent MVP dimer via gradual side-to-side interactions to form an MVP tetramer. Successive addition of growing MVP dimers, layer by layer like in a 3D printing process, continues until the requisite number of MVP proteins required for a vault (e.g., 78-mer for rat vaults) is reached and a completed vault structure is provided at the 3' end of the polyribosome.

This polyribosome templating implies that: (i) the local MVP monomer concentration on a polyribosome is a reflection of the polyribosome topology and the generation of a mature vault particle does not depend on a particular cellular concentration of MVP monomers; (ii) free MVP monomers should not exist at any given time as the polyribosome templating is a co-translational event; (iii) each vault is translated from the same copy of mRNA; and (iv) the observed roll-like structures of the 6-His MVP mutant should be tethered to a polyribosome as they have lost their ability to pinch-off.

Figure 5A:
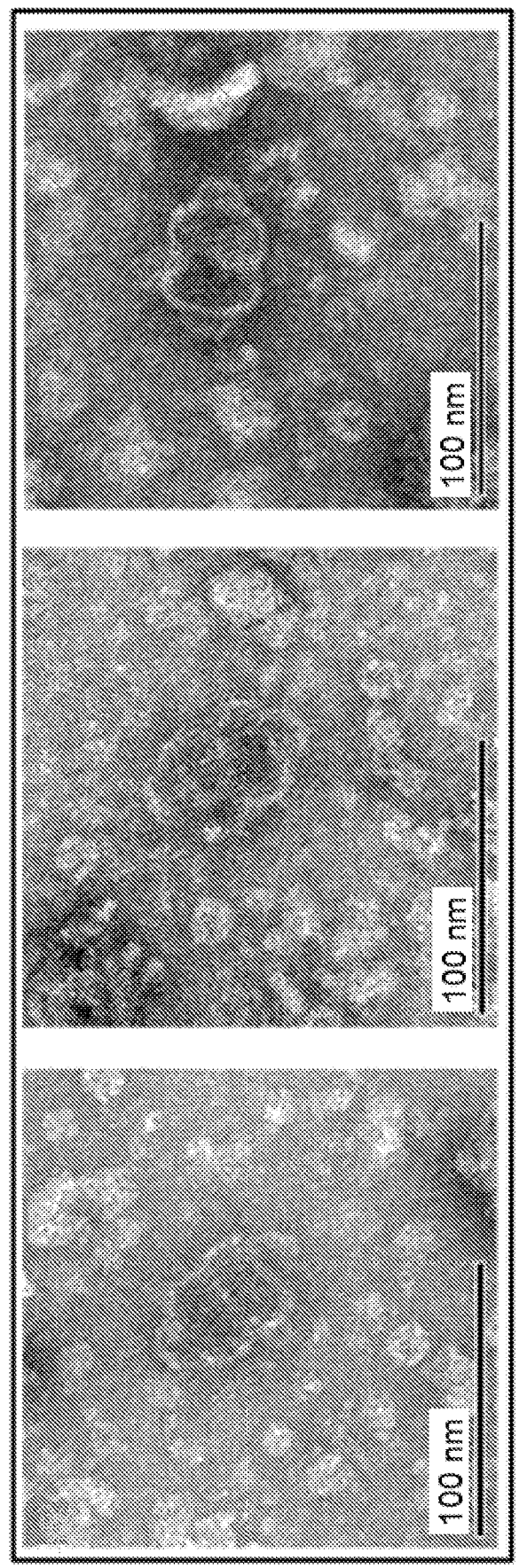
FIGS. 5A-5C provide experimental evidence for polyribosome templating.

The self-assembly model of vault generation would require a critical concentration of MVP monomers. However, vaults were detected by EM following in vitro translation of MVP mRNA under conditions where very low concentrations of MVP were synthesized (FIG. 5A). This result provides further evidence for the polyribosome templating model of vault assembly which predicts that a single MVP mRNA is sufficient to produce a vault given a sufficient amount of a synthesis mixture.

Figure 5B:
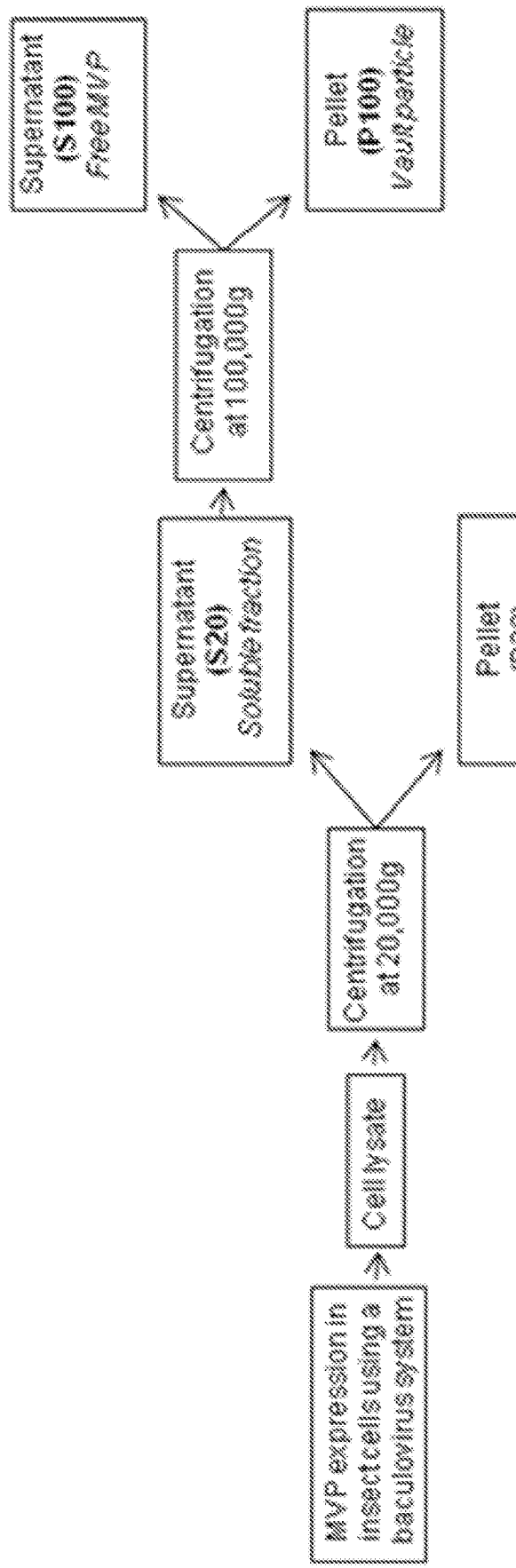
Figure 5C:
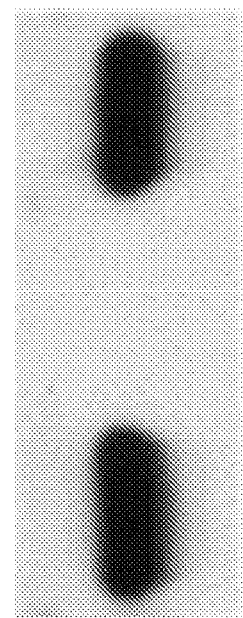

To demonstrate that all of the MVP monomers are incorporated into the vault particles, differential centrifugations (FIG. 5B) of insect cell lysate expressing MVP were performed and followed by Western blot analysis. As seen in FIG. 5C, free MVP monomers were not detected.

Figure 6:
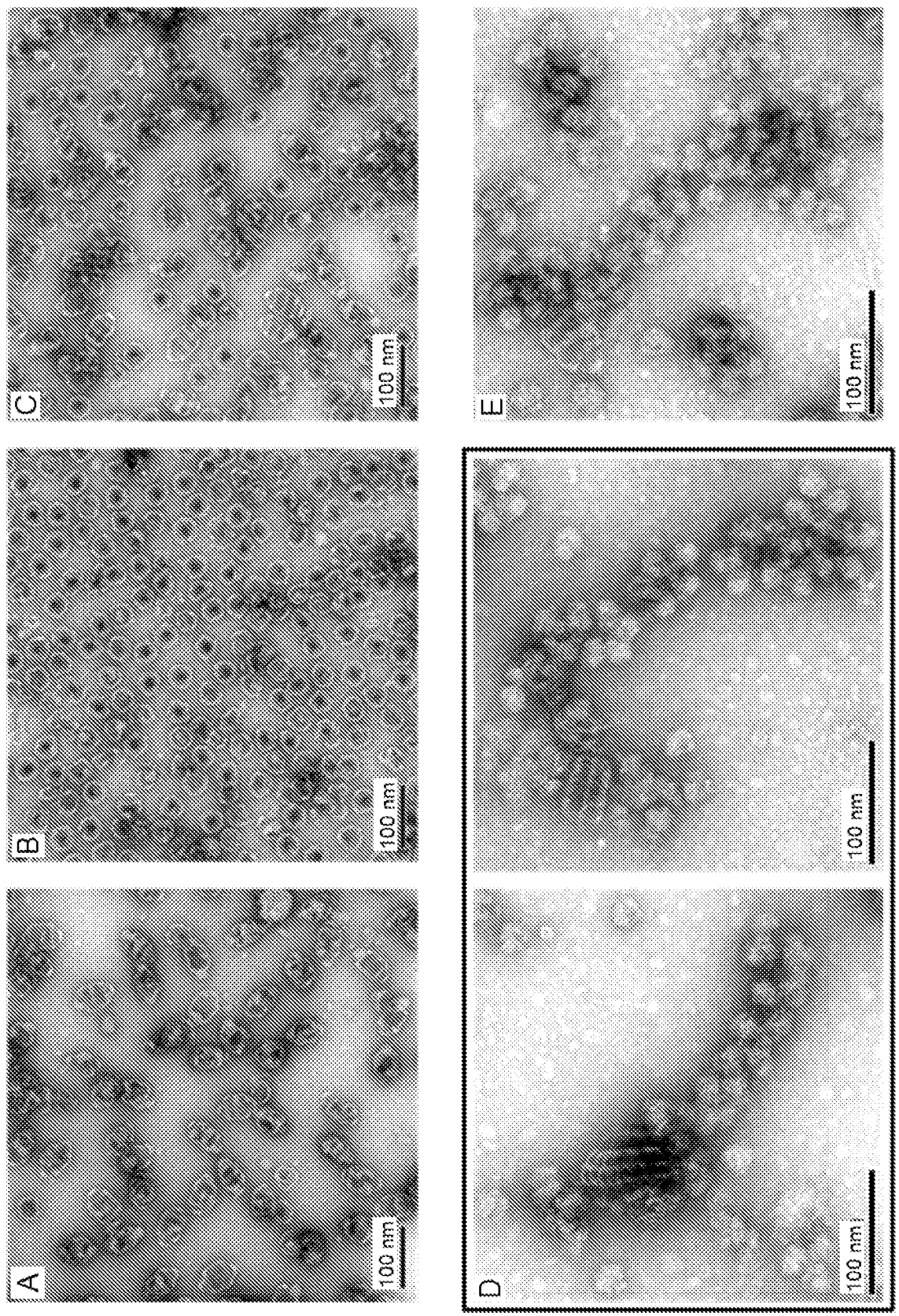
FIG. 6, Panels A-E, provide additional supportive evidence for polyribosome templating. Panels A-C are micrographs showing that co-expression of two different MVP mRNAs leads to two types of vaults. Electron micrograph of (Panel A) VSVG-MVP full vaults expressed from a single promoter plasmid, (Panel B) mCherry-MVP half vaults expressed from a single promoter plasmid, and (Panel C) co-expression of mCherry/VSVG-MVP half and full vaults using a dual promoter plasmid. Panels D-E are micrographs showing the visible association of 6-His MVP mutant structures with polyribosomes. Electron micrographs of purified polyribosomes from Sf9 cells expressing 6-His MVP for 48 hours (Panel D) or MVP for 24 hours (Panel E). Samples were negatively stained with uranyl acetate. Scale bars=100 nm.

To test whether each assembled vault would be translated from the same copy of mRNA, co-expression experiments using two different MVP mRNAs were performed. Thus, if two different MVP mRNAs are present in the same cell, two different vault particles would be formed. To test this theory, mRNA coding for an MVP containing an N-terminal fusion with mCherry fluorescence protein (mCherry-MVP) and mRNA coding for a VSVG tagged N-terminal MVP fusion (VSVG-MVP) were expressed in the same population of insect cells using a dual promoter expression system. When VSVG-MVP mRNA was expressed alone from a single promoter plasmid, stable vaults were formed (FIG. 6, Panel A). In contrast, expression of the mCherry-MVP mRNA alone resulted in unstable vaults that rapidly dissociated into halves under conditions used for uranyl acetate staining (FIG. 6, Panel B). Co-expression of the two different MVP mRNAs in the same cells using the dual promoter system, revealed that indeed two types of vaults were formed (FIG. 6, Panel C).

When polyribosomes were isolated from cells expressing the 6-His MVP mutant at 48 hours following infection, numerous bound MVP rolls were observed (FIG. 6, Panel D). At a later time period, the rolls were considerably larger in diameter to those seen at 24 hours, thereby indicating the inability of the proteins to pinch-off from the polyribosomes.

Individual assembled vaults were found associated with polyribosomes that were isolated from Sf9 cells expressing MVP proteins that were not 6-His MVP mutants (FIG. 6, Panel E). The observation of a vault associated with a polyribosome was a less frequent event, as these vaults possess the native ability to pinch-off from the polyribosome upon their completion.

Engineered Vaults Made by Cell-Free Techniques

As shown in FIG. 5A, vaults were detected after in vitro translation of MVP mRNA using cell-free system (EasyXpress Insect Kit II, Qiagen, Valencia, Calif.).

Therefore, in some embodiments, the present invention provides vaults made by cell-free techniques. In some embodiments, the present invention provides vault rolls (i.e., rolled structures of MVP proteins), vault halves, and mixtures thereof made by cell-free techniques, which comprise disrupting the antiparallel β sheet interactions that normally form between the N-terminal amino acids of wild-type MVP proteins. In some embodiments, the disruption is by way of amino acid substitutions. In some embodiments, amino acid residues at positions 3-7 are substituted. In some embodiments, amino acid residues at positions 3-8 are substituted. In some embodiments, one or more of the amino acid residues that are substituted with histidine. In some embodiments, the vaults, vault rolls, and/or vault halves are made using a commercially available cell-free expression kit.

Since Abnova Taiwan Corporation (Taipei, Taiwan) sells major vault protein monomer extracts that are made using cell-free techniques, unpurified human MVP crude extract (#H00009961-P01-w/o purify) was obtained and examined to determine whether any vault structures were present. Specifically, in order to determine whether any vault structures were present, 1 ml of crude extract was centrifuged at 20,000×g for 20 minutes at 4° C. The supernatant, labeled as "S20", was collected and treated with RNase A for 30 minutes at room temperature (RT), followed by centrifugation at 16,000×g for 10 minutes at RT. The supernatant was collected and analyzed by electron microscopy. After a thorough visualization, not a single vault was spotted. Since the MVP crude extract is not purified, the extract was not subject to conditions that could denature vault structures. Thus, the absence of any vault structures indicates that no vault structures are formed during the production, i.e., in vitro translation, of the MVP monomers by Abnova Taiwan Corporation.

The MVP monomers sold by Abnova Taiwan Corporation are fusion proteins that comprise a GST-tag fused to MVP, in this case, the N-terminus of MVP. Human MVP is about 98 kDa, while the GST-tag is about 26 kDa. Thus, it is believed that the GST-tag interferes with the assembly of MVP monomers into vault structures during in vitro translation. Therefore, in some embodiments, the methods of the present invention employ a nucleic acid molecule that encodes a protein that consists essentially of or consists of an MVP protein. As used herein, a "protein that consists essentially of an MVP protein" means that the protein has a sequence that has 90-100%, preferably 95-100%, sequence identity to a major vault protein, which said sequence is capable of forming a part of a vault, and the protein may contain an additional sequence at the N-terminus and/or the C-terminus of the sequence so long as the protein is capable of forming a part of a vault. In other words, a "protein that consists essentially of an MVP protein" is an MVP protein that may have an additional sequence fused thereto so long as the additional sequence does not interfere with the ability of the MVP protein to form vaults during in vitro translation. As used herein, a "protein that consists of an MVP protein" means that the protein has a sequence that has 90-100%, preferably 95-100%, sequence identity to a major vault protein, which said sequence is capable of forming a part of a vault, and the protein does not contain an additional sequence at either the N-terminus or the C-terminus.

Additionally, in vitro translation methods that do not provide sufficient amounts of starting reagents, e.g., amino acids, creatine kinase, ATP, etc., in the synthesis mixtures, do not result in the synthesis of sufficient quantities for a polyribosome to make enough copies of MVP monomers (e.g., about 78 copies) in order to form a vault. Therefore, in some embodiments, the methods of the present invention comprise employing a synthesis mixture that contains an amount of starting materials that is sufficient for at least one polyribosome to synthesize at least one vault particle. In some embodiments, the cell-free technique of the present invention is performed in a continuous mode whereby the starting materials are regularly added to the synthesis mixture in an amount sufficient for at least one polyribosome to synthesize at least one vault particle.

Packaging of Engineered Vaults

After Determining that Engineered Vaults could be Made Using Cell-Free Techniques instead of cell-based expression systems, the following experiments were conducted to determine whether passenger molecules could be packaged in the cavities of vaults during polyribosome templating.

Figure 7:
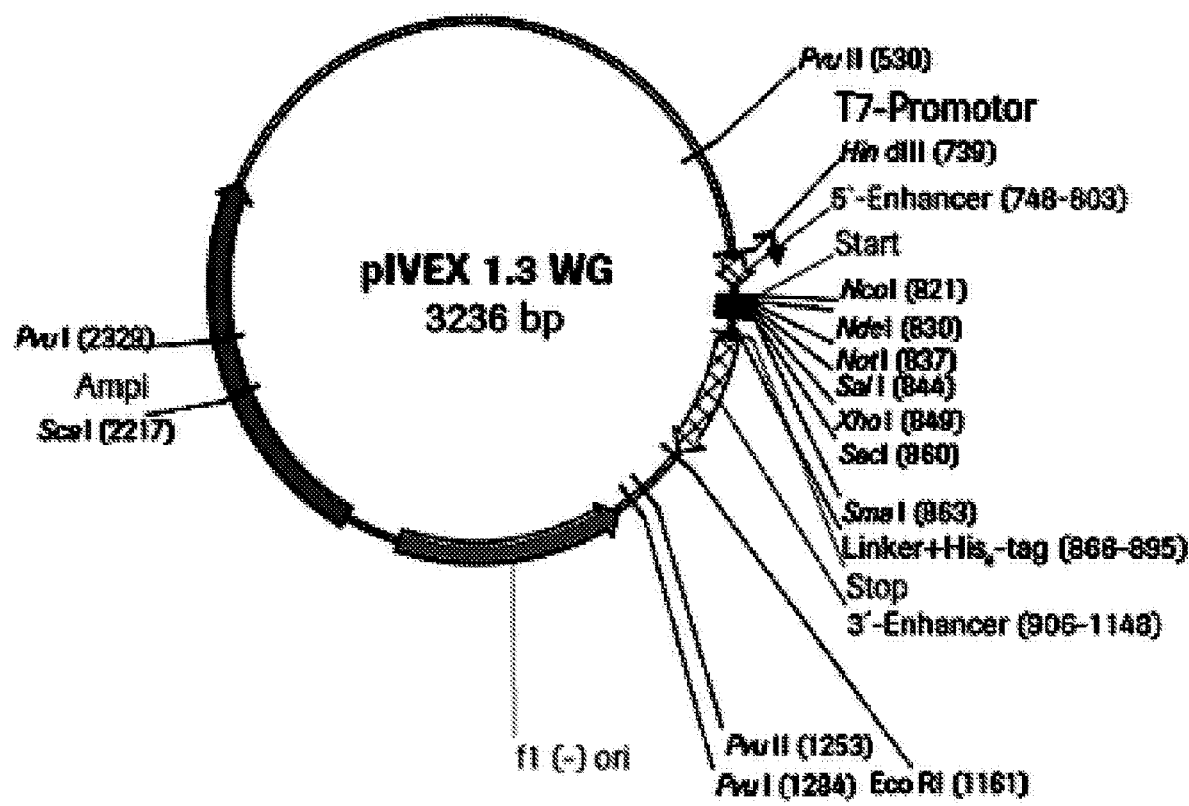
FIG. 7 schematically shows the pIVEX 1.3 Wheat Germ Expression Vector used in the packaging experiments.

Packaging of Labeled siRNA or Labeled Ovalbumin by Vaults Using Cell-Free Techniques For the packaging experiments, the WEPRO® 7240 wheat germ extract and the SUB-AMIX® SGC translation buffer (CellFree Sciences, Yokohama, Japan) or RTS 100 Wheat Germ CECF Kit (Biotechrabbit, Hennigsdorf, Germany) were used for protein expression. Major vault protein (rMVP) cloned into the pIVEX 1.3 wheat germ expression vector (FIG. 7) was used in a PCR reaction to produce a linear DNA template. The sequence of the pIVEX 1.3 wheat germ expression vector is set forth in FIG. 8A. The sequence of the rMVP-pIVEX vector sequence is set forth in FIG. 8B. The linear DNA template is set forth in FIG. 8C. The linear DNA template was analyzed and purified by agarose gel electrophoresis. Subsequently, an mRNA transcript was synthesized using 1 μg of the purified linear DNA template in a 20 μl AmpliScribe T7-Flash reaction (Epicentre, Madison, Wis.) at 37° C. for 30 minutes. Resulting mRNA was purified by ammonium acetate precipitation, resuspended in 20 μl of nuclease free $H_2O$ and quantified using a Nanodrop® spectrophotometer (ThermoScientific, Waltham, Mass.). For each 0.5 ml cell free protein synthesis reaction 150 μg of rMVP mRNA was added.

The in vitro translation reaction was assembled using the dialysis protocol from CellFree Sciences with slight modifications (Yokohama, Japan). For each reaction, 20 ml of 1× SUB-AMIX® SGC translation buffer was prepared in RNase free water from a 40× SUB-AMIX® SGC buffer. 250 μl was reserved for the translation reaction and the remaining was added to a small round plastic container. Two translation reactions were set up, each containing 20 µl RNA transcript (150 µg), 250 µl 1× SUB-AMIX® SGC, 83 µl WEPRO® 7240 wheat germ extract, and 2 µl creatine kinase (20 mg/ml). To one reaction, fluorescently labeled siRNA was added at a final concentration of 0.7 mg/ml. Finally, RNase free water was added to bring the final volume of the translation reaction to 0.5 ml. The 0.5 ml translation reaction was then loaded into a 0.5 ml Slide-A-Lyzer dialysis cassette (ThermoFisher, Waltham, Mass.), pre-wetted with translation buffer, using an 18 gauge 1½ inch needle connected to a 1 ml syringe. The loaded cassette was then submerged in the translation buffer contained in the plastic container and gently shaken for about 40 hours at room temperature (23-24° C.). At completion, the reaction mixture was retrieved from the dialysis cassette. 6 µl was reserved for protein gel analysis while the remaining was clarified by centrifugation at 20,000×g for 20 minutes and the supernatant, labeled as "S20", was collected. 6 µl of S20 was saved for protein gel analysis, and additional 170 µl of the S20 was treated with 1 M ammonium acetate for 15 minutes on ice, the resulting precipitate being collected by centrifugation and resuspended in a final volume of 30 µl. The remainder of the S20 was treated with RNase A for downstream studies (sucrose gradient analysis).

Figure 9:
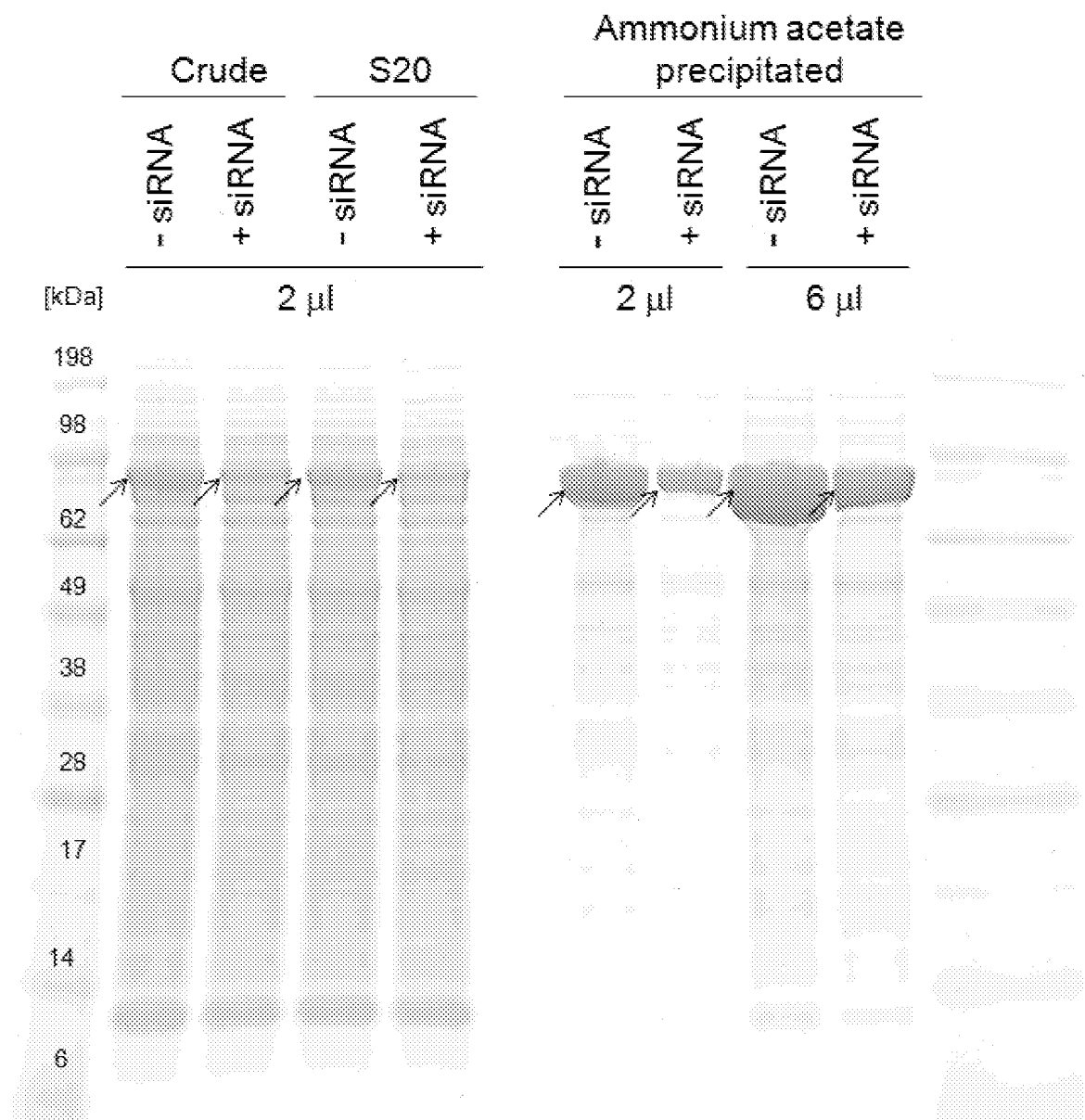
FIG. 9 is a Coomassie staining of an SDS-PAGE of crude translation product, S20 and ammonium acetate precipitated S20 samples.

Crude translation reaction, S20, and ammonium acetate precipitated S20 samples were analyzed by SDS-PAGE and Coomassie staining (FIG. 9). The arrows in FIG. 9 indicate the MVP protein (96 KDa). The results show that vault nanoparticles were successfully made in the presence and the absence of the packaging labeled molecule, although more efficient production was achieved in the absence of labeled siRNA. The reduced efficiency observed in the presence of siRNA was due to the chloride ions present in its storage buffer known to be inhibitory to translation. Thus, in some embodiments, chloride ions can be removed from the storage buffer or a storage buffer lacking chloride ions can be used in order to improve translation.

Figure 10:
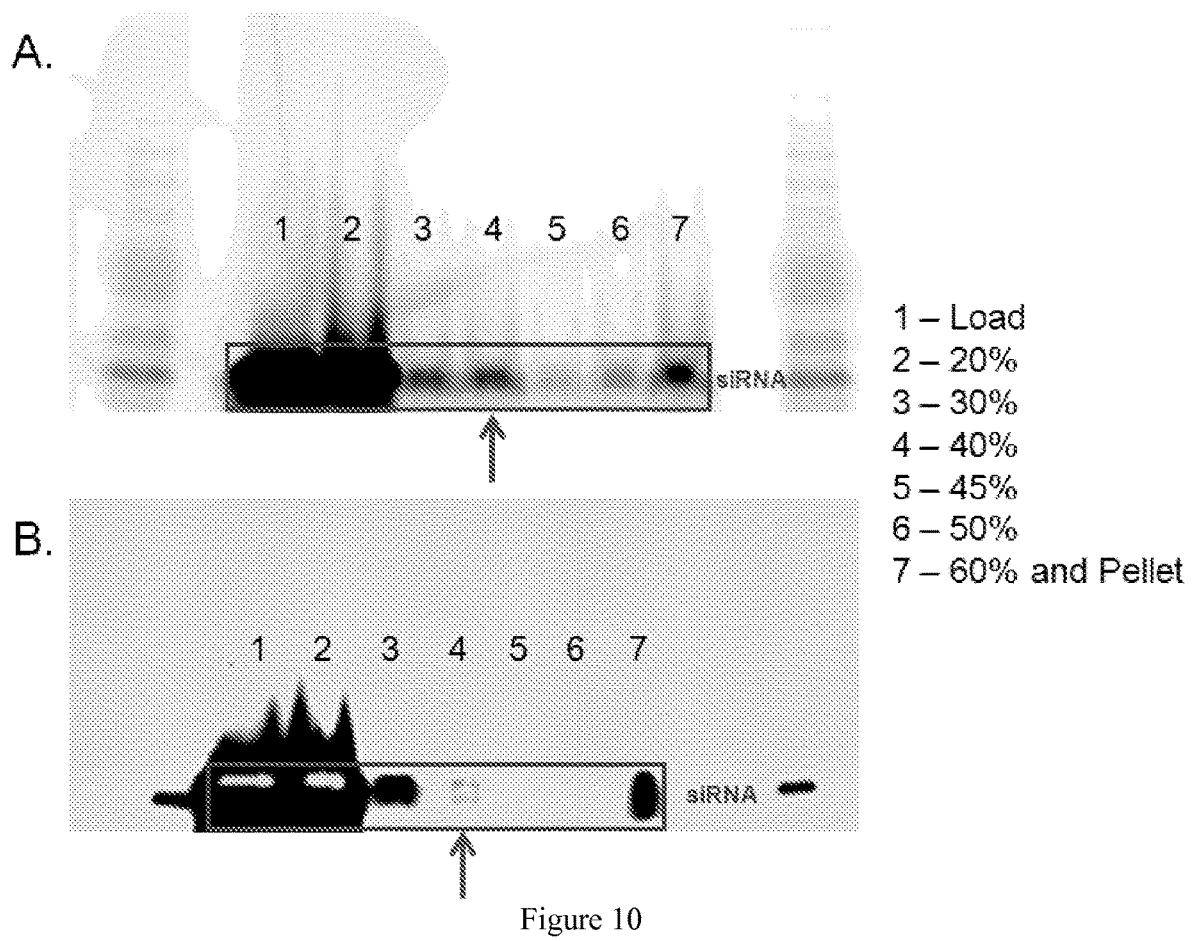
FIG. 10, Panels A and B, is fluorescent imaging of the sucrose fractions of siRNA with and without vault nanoparticles. Panel A shows Typhoon imaging of sucrose fractions from the RNase A treated siRNA vault translation product. Panel B shows LI-COR imaging of sucrose fractions from the siRNA control.

To determine whether siRNA was associated with the vault nanoparticle, RNase A treated siRNA vaults were overlaid onto sucrose step gradients (20%, 30%, 40%, 45%, 50%, and 60%) and centrifuged at 25K in SW41 Beckman Coulter rotor for 16 hours at 4° C. All the sucrose fractions were collected, analyzed by SDS-PAGE and the presence of siRNA was measured quantitatively with the Typhoon laser scanner (GE Healthsciences Life Sciences, Pittsburgh, Pa.) (FIG. 10). Fractions from RNase A treated vaults (FIG. 10A) show fluorescently labeled siRNA that were not encapsulated during vault assembly migrated only to the 20% (FIG. 10A, lane 2), with common minor spillover into the 30% fraction (FIG. 10A, lane 3), while those that were encapsulated co-migrated with the vault and appeared in the 40% sucrose fraction (FIG. 10A, lane 4, red arrow). To further illustrate the specificity of the siRNA association with the vault complex, siRNA alone was overlaid onto sucrose step gradients and analyzed as described above except fluorescence was measured with a LI-COR Imaging System (Lincoln, Nebr.). siRNA is observed in load, 20% and 30% (FIG. 10B, lanes 1, 2, and 3), but is essentially absent from the 40% fraction (FIG. 10B, lane 4, red arrow).

In similar experiments, ovalbumin was packaged in the vaults using cell-free techniques. Briefly, fluorescently labeled ovalbumin (OVA) protein was added to the in vitro cell-free vault synthesis reaction. At completion, the reaction mixture was overlaid onto sucrose step gradients (20%, 30%, 40%, 45%, 50%, and 60%) and centrifuged at 25K in SW41 Beckman Coulter rotor for 16 hours at 4° C. The 40% and 45% fractions were collected, pooled, and vaults were isolated by centrifugation (40K in Ti70.1 Beckman Coulter rotor at 4° C. for 2 hours). The resulting vault pellet was resuspended in buffer and overlaid on a second sucrose step gradient as previously described. All the sucrose fractions were collected and analyzed by SDS-PAGE. Fluorescently labeled OVA molecules that are not encapsulated during vault assembly will migrate only to the 20% while those that were encapsulated will co-migrate with vault and appear in 40% and 45% sucrose fractions. The fluorescent signal was measured quantitatively with the Typhoon laser scanner (GE Healthsciences Life Sciences, Pittsburgh, Pa.).

Figure 11A:
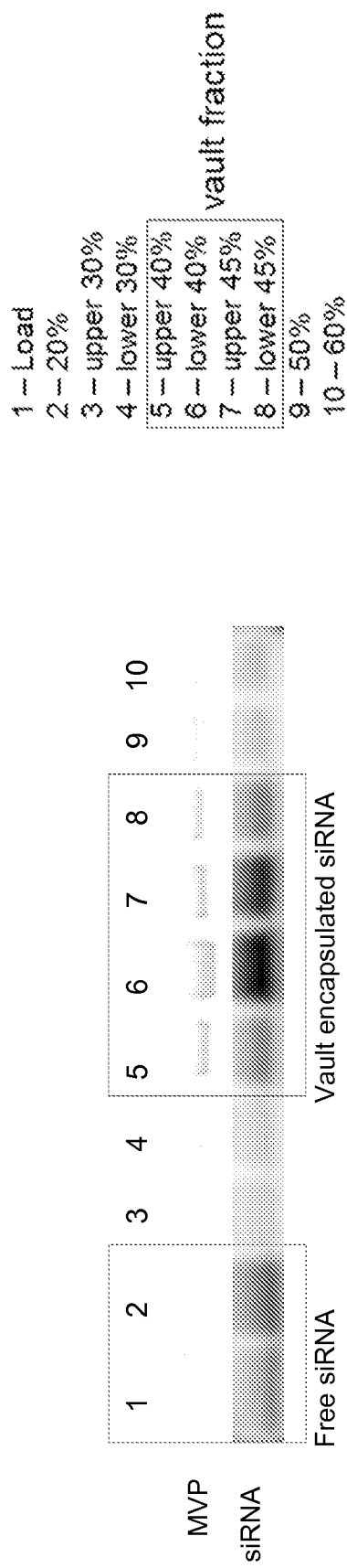
FIG. 11A shows the SDS-PAGE sucrose gradient profile of the siRNA packaging.
Figure 11B:
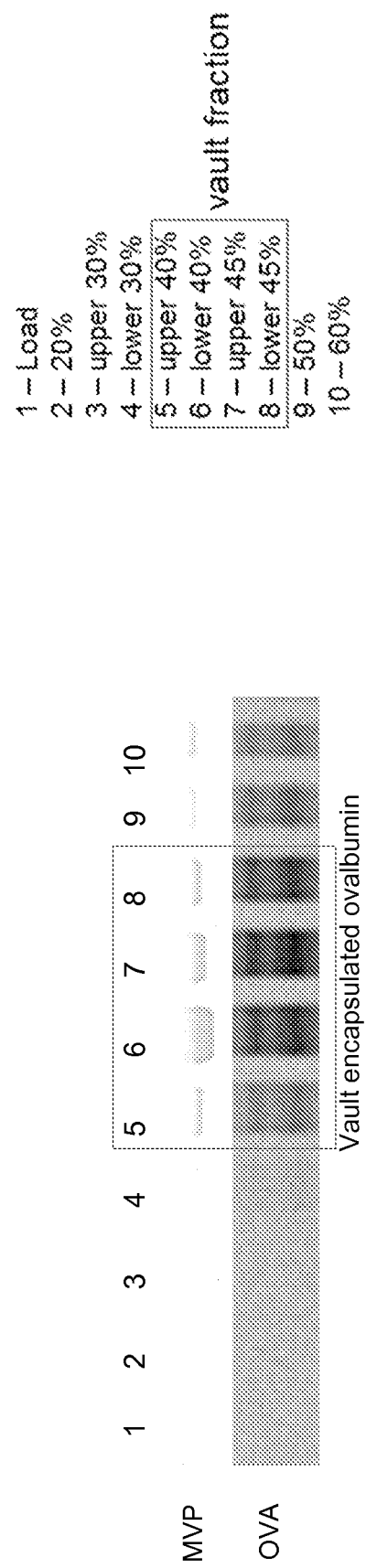
FIG. 11B shows the SDS-PAGE sucrose gradient profile of the ovalbumin packaging.

The SDS-PAGE of the second sucrose gradient profiles of the siRNA packaging and the ovalbumin packaging are provided in FIG. 11A and FIG. 11B, respectively. These experiments show that making vaults using cell-free techniques with passenger molecules present in the translation reaction mixtures result in the packaging of the passenger molecules in the internal cavities of the formed vaults. Additionally, it was found that, when packaged, the siRNA and ovalbumin molecules co-migrate with the vault particle into denser (40% and 45%) sucrose fractions as compared migration of the unpackaged molecules to the 20% sucrose fraction.

Therefore, in some embodiments, the present invention provides methods of packaging one or more passenger molecules in the internal cavity of a vault particle, which comprises providing the one or more passenger molecules in the translation reaction mixture during in vitro translation of the MVP proteins and formation of the vault particles. In some embodiments, at least two different passenger molecules are packaged in the internal cavity of a vault particle. In some embodiments, one of the two passenger molecules is a passenger molecule that is recombinantly fused to the mINT sequence (passenger-mINT fusion protein) and the other passenger molecule is "free", i.e., not recombinantly fused to the mINT sequence. In some embodiments, the passenger molecule of the passenger-mINT fusion protein is a protein. In some embodiments, a free passenger molecule is packaged in an internal cavity of a vault particle by providing it in the translation reaction mixture during in vitro translation of the MVP proteins and formation of the vault particles, and a passenger-mINT fusion protein is packaged in the internal cavity with the free passenger molecule by mixing the vault particle after formation with the passenger-mINT fusion protein.

Analysis of Vaults Made Using Cell-Free Techniques

Purified samples of vaults were obtained by clarifying crude translation product by centrifugation at 20,000×g at 4° C. for 20 minutes. The resulting supernatant (S20) was treated with RNase A at room temperature for 30 minutes followed by centrifugation at 16,000×g at room temperature for 10 minutes. The resulting supernatant was overlaid onto sucrose step gradients (20%, 30%, 40%, 45%, 50%, and 60%) and centrifuged at 25K in SW41 Beckman Coulter rotor at 4° C. for 16 hours. The 40% and 45% sucrose fractions were pooled together, diluted with buffer A (50 mM Tris-Cl buffer pH 7.4, 75 mM NaCl, 0.5 mM $MgCl_2$) and centrifuged at 40K in Ti70.1 Beckman Coulter rotor at 4° C. for 2 hours. The pellet of purified vaults was resuspended in buffer A and quantified by BCA Protein Assay (ThermoFisher, Waltham, Mass.).

Figure 12A:
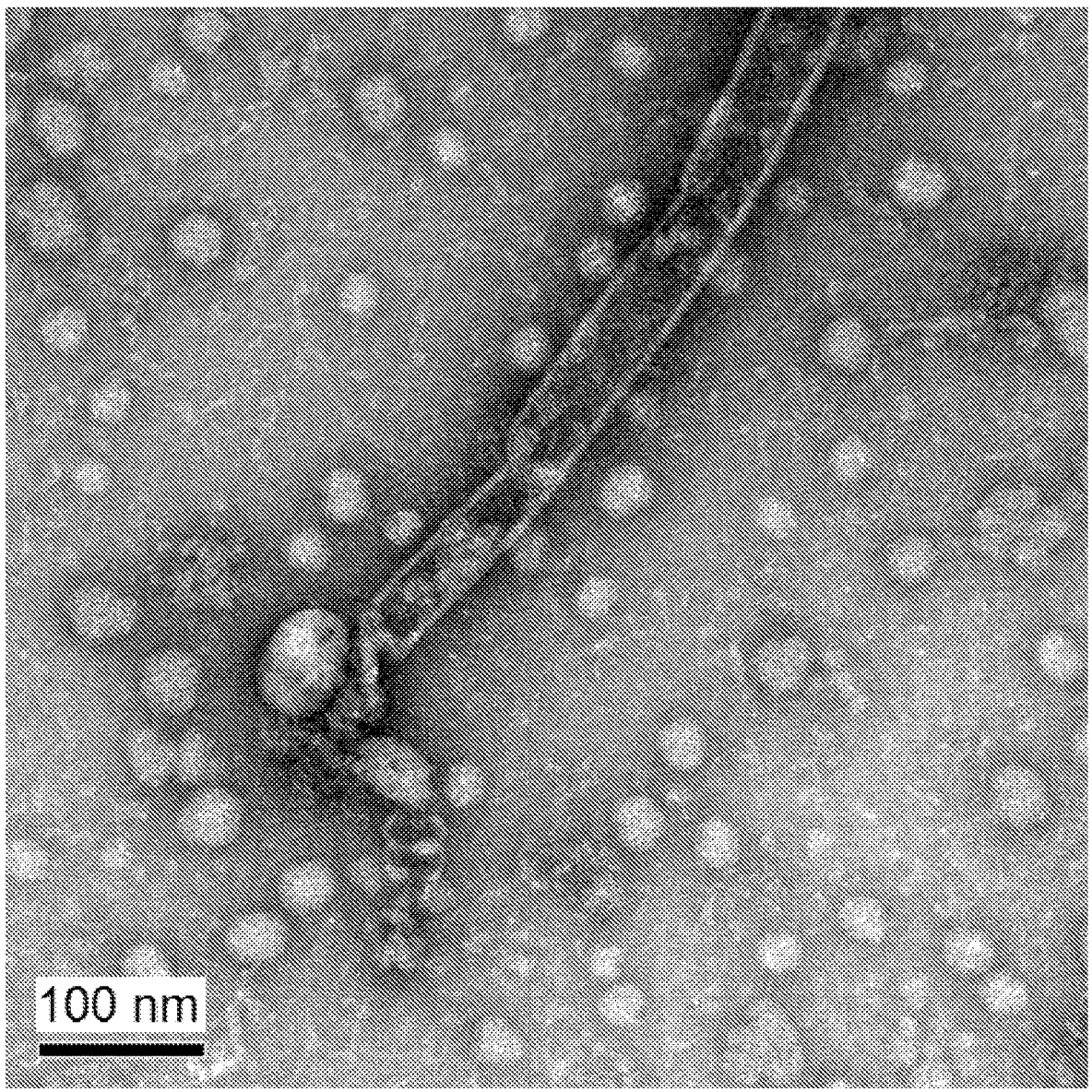
FIG. 12A is an electron micrograph showing a baculovirus tube in a purified sample of vaults made using a baculovirus cell-based expression system.
Figure 12B:
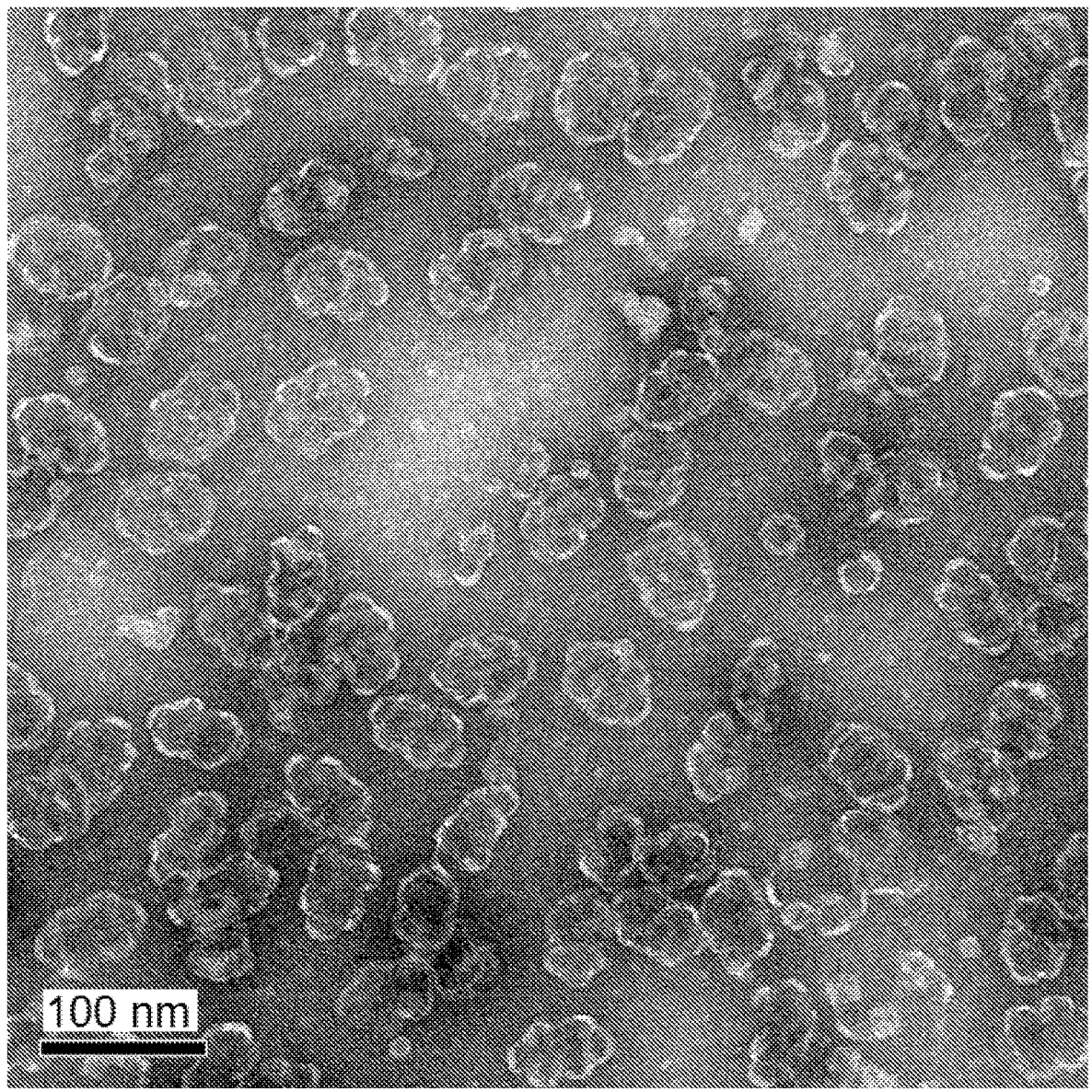
FIG. 12B is an electron micrograph showing the absence of baculovirus tubes in a sample of vaults made using cell-free techniques. Vaults comprising rMVP were synthesized in a cell-free wheat germ expression system. The sample was stained with 1% uranyl acetate solution.

FIG. 12A is an electron micrograph of a purified sample of vaults made using the baculovirus expression system, which is a cell-based technique. As can be seen in FIG. 12A, baculoviral tubes, are present. Baculovirus tubes are ubiquitous contaminants present in samples of vaults made using baculovirus expression systems. Conversely, as shown in FIG. 12B, such contaminants are not found in samples of vaults made by cell-free techniques.

The concentration of purified vaults made using cell-free techniques as described herein was determined by BCA Protein Assay to be about 500 μg per ml. Thus, the methods according to the present invention can be used to produce up to about 250 μg of vaults that are free of cellular debris such as baculovirus tubes from about 0.5 ml translation reaction in about 40 hours.

As shown herein, vaults made using cell-based expression systems comprise cellular debris that remain after lysing the host cells and purifying the vaults. Also, as shown herein, molecules that are present in the translation reaction mixtures during polyribosome templating can be entrapped in the internal cavities of vault particles. Thus, various molecules within the cytoplasm of a host cell can be entrapped in the internal cavities of vault particles when such are made using cell-based expression systems. However, since vaults made using cell-free techniques are formed in vitro in translation reaction mixtures, the vaults are free of cellular debris that results from cell-based expression systems. Therefore, in some embodiments, the present invention provides engineered vaults, vault rolls, and vault halves that are free of cellular debris. In other words, the engineered vaults, vault rolls, and vault halves according to the present invention do not contain any cellular debris that results from making vaults using cell-based systems.

In some embodiments, the present invention provides compositions comprising one or more engineered vaults, one or more vault rolls, and/or one or more vault halves, wherein said compositions are free of cellular debris. In some embodiments, the compositions comprise two or more different types of engineered vaults, two or more different types of vault rolls, and/or two or more different types of vault halves. As used herein, a vault, vault roll, or vault half that is of a "different type" as compared to another is one that has an MVP protein sequence that is different from the MVP protein sequence of the other particle and/or contains one or more passenger molecules that are different from that of the other particle.

In some embodiments, the compositions may comprise (a) a first portion of engineered vaults that have, in the internal cavities, a first passenger molecule packaged therein during polyribosome templating and (b) a second portion of engineered vaults, which are also made by polyribosome templating, that have a second passenger molecule packaged in the internal cavities as passenger-mINT fusion proteins by mixing formed engineered vaults with the passenger mINT fusion proteins. In some embodiments, the passenger molecule of the passenger-mINT fusion protein is a protein. In some embodiments, the MVP protein sequences of the first portion of engineered vaults and the second portion of the engineered vaults are the same. In some embodiments, the MVP protein sequences of the first portion of engineered vaults and the second portion of the engineered vaults are different. In some embodiments, the first and second passenger molecules (excluding the mINT sequence and any linkers) are the same. In some embodiments, the first and second passenger molecules (excluding the mINT sequence and any linkers) are different.

In some embodiments, the compositions may comprise (a) a first portion of engineered vaults that have, in the internal cavities, a first passenger molecule packaged therein during polyribosome templating, and (b) a second portion of engineered vaults, which are made using cell-based expression systems, that have a second passenger molecule packaged in the internal cavities as passenger-mINT fusion proteins by mixing formed vaults with the passenger-mINT fusion proteins. In some embodiments, the passenger molecule of the passenger-mINT fusion protein is a protein. In some embodiments, the MVP protein sequences of the first portion of engineered vaults and the second portion of the engineered vaults are the same. In some embodiments, the MVP protein sequences of the first portion of engineered vaults and the second portion of the engineered vaults are different. In some embodiments, the first and second passenger molecules (excluding the mINT sequence and any linkers) are the same. In some embodiments, the first and second passenger molecules (excluding the mINT sequence and any linkers) are different.

In some embodiments, the compositions comprise engineered vaults having at least two different passenger molecules packaged in the internal cavities. In some embodiments, one of the two passenger molecules is a passenger molecule that is recombinantly fused to the mINT sequence (passenger-mINT fusion protein) and the other passenger molecule is "free", i.e., not recombinantly fused to the mINT sequence. In some embodiments, the passenger molecule of the passenger-mINT fusion protein is a protein. In some embodiments, a free passenger molecule is packaged in an internal cavity of a vault particle by providing it in the translation reaction mixture during in vitro translation of the MVP proteins and formation of the vault particles, and a passenger-mINT fusion protein is packaged in the internal cavity with the free passenger molecule by mixing the vault particle after formation with the passenger-mINT fusion protein.

Packaging to Obtain Desired Concentrations

Based on theoretical calculations, one may obtain a desired concentration of passenger molecules in the internal cavities of vaults. Specifically, assuming that the internal cavity of a vault has a volume of about $3.58 \times 10^7$ Å$^3$ and 1 μl=$1 \times 10^{21}$ Å$^3$, 1 μl is equivalent to a maximum of $2.79 \times 10^{13}$ ($1 \times 10^{21}/3.58 \times 10^7$) vault interiors. Thus, 1 L is equivalent to $2.79 \times 10^{19}$ vault interiors, which is a maximum of $0.463 \times 10^{-4}$ ($2.79 \times 10^{19}/6.0221413 \times 10^{23}$) mol of vault interiors or 46.3 μmol of vault interiors, which gives a maximum concentration of 46.3 μM of vault interiors.

Thus, the concentration of a passenger molecule to be packaged in the interior cavity of a vault particle during cell-free synthesis should be 46.3 μM in order to achieve theoretical packaging of 1 molecule per vault. Similarly, a passenger molecule concentration of 92.6 μM in the synthesis mixture would increase the probability to having two passenger molecules being packaged within an interior cavity of a vault. Table 1 sets forth the theoretical concentrations for packaging a target number of passenger molecules in the internal cavity of a vault.

TABLE 1

| Passenger molecule concentration [μM] in cell free protein synthesis reaction | Target number of passenger molecule(s) to be packaged in the interior cavity of a vault |
|---|---|
| 11.6 | 0.25 |
| 23.2 | 0.5 |
| 46.3 | 1 |
| 92.6 | 2 |
| 138.9 | 3 |
| 185.2 | 4 |
| 231.5 | 5 |
| 277.8 | 6 |
| 324.1 | 7 |
| 370.4 | 8 |

TABLE 1-continued

| Passenger molecule concentration [μM] in cell free protein synthesis reaction | Target number of passenger molecule(s) to be packaged in the interior cavity of a vault |
|---|---|
| 416.7 | 9 |
| 463.0 | 10 |

Given a protein passenger such as albumin, the space occupied by it would be approximately $5.23 \times 10^5$ Å$^3$, thus at a concentration of 46.3 μM, albumin would displace a volume of $5.23 \times 10^5$ Å$^3$ from the vault interior volume as it is packaged (i.e. 1/68 of the vault interior volume capacity).

Therefore, in some embodiments, the present invention provides a method of packaging a target number of given passenger molecules in the internal cavities of engineered vaults made by polyribosome templating, which comprises calculating the concentration of passenger molecules that is theoretically required to package the number of desired passenger molecules in an internal cavity of a vault, providing the passenger molecule in a synthesis mixture at the calculated concentration, and performing in vitro translation using the synthesis mixture to form an engineered vault. For example, passenger molecules to be packaged during vault assembly are dissolved in buffer compatible with in vitro translation, the passenger molecule is added to the synthesis mixture in a concentration consistent with Table 1 to achieve a desired packaging ratio (e.g., siRNA passenger molecules are added to a synthesis mixture at a final concentration of 92.6 μM in order to package 2 siRNA molecules per vault particle). Note: When employing dialysis mode in vitro translation, if the passenger molecule is small enough to diffuse across the membrane separating the reaction compartment from the feeding solution compartment, it is preferred that the passenger molecule is added to both compartments in equal concentrations.

Additional MVP Experiments

Human MVP (SEQ ID NO: 12) was cloned within the NcoI and KpnI site of the pIVEX 1.3 wheat germ expression vector and vaults were in vitro translated and passenger molecules were packaged during in vitro translation as described above for rat MVP. The hMVP-pIVEX 1.3 sequence is provided as SEQ ID NO: 13. Additionally, human MVP and rat MVP were each cloned within the NcoI and XbaI site of the multiple cloning site (MCS) of the pT7-IRES expression vector provided with the Human Cell-Free Protein Expression System (Cat. #3281) from Takara Bio Inc. (sold by Clontech Laboratories, Inc. Mountain View, Calif.) and vaults were produced and packaged by performing in vitro transcription and translation using the system according to the manufacturer's instructions. Expected results are similar to those as set forth above. The sequence for hMVP cloned in pT7-IRES is provided as SEQ ID NO: 14 and the sequence for rMVP cloned into pT7-IRES is provided as SEQ ID NO: 15. It is expected that vaults comprising human MVP will be produced by in vitro translation and passenger molecules can be packaged by providing the passenger molecules in the synthesis mixture during in vitro translation.

Exemplary Protocol for Cell-Free Techniques and Packaging

The following is an exemplary general protocol for cell-free in vitro production of vault particles.

1) Clone MVP gene into a vector harboring a promoter, e.g., T7 promoter (alternatively, PCR amplify MVP gene with primers containing T7 promoter sequence at the 5' end).
2) Prepare continuous in vitro reaction in 1.5 ml microfuge tube by mixing the following:
   a. A synthesis mixture comprising ribosomes, aminoacyl-tRNA synthetases, along with all of the other requisite macromolecular components and factors for transcription and translation, including amino acids, energy sources, energy regeneration systems, and various cofactors. Commercially available synthesis mixtures, preferably originating from eukaryotic cells that naturally do not contain vaults, e.g., plant cells, insect cells, may be used.
   b. Solution of desired molecule(s) to be packaged or incorporated (if using modified amino acids) into the vault-like particle. (Note: Larger biopolymers like plasmid DNA can be pre-condensed with protamine in order to fit inside the vault).
   c. T7 promoter containing MVP DNA (from step 1), 1-4 μg/50 μl reaction volume.
3) Pipette mixture into a bioreactor with semipermeable membrane that allows for diffusion of the feed mixture, a solution containing desired molecule(s) to be packaged or incorporated along with supplementary amino acids and sources of energy. Reaction is scalable by increasing the size of the bioreactor and volume of feed mixture.
4) Incubate reaction at 24-27° C., shaking at 900 rpm for 24 hours.
5) Efficiency of in vitro production can be analyzed by EM for vault integrity and packaging efficiency. Mass spectrometry, fluorescence microscopy, sedimentation experiments, and electrophoretic methods can be used to determine the packaging efficiency as well.

In some embodiments, the bioreactor is a vessel with two chambers, a feeding chamber, and a reaction chamber, that are separated from each other by a semi-permeable membrane and the reaction chamber is where the vault particles are formed. Where the pores of the semi-permeable membrane are about 15 kDa or smaller, the produced vaults are therefore contained within the reaction chamber. In some embodiments, a feeding solution containing amino acids, a source of energy and other supporting molecules for continuous in vitro translation may be added to the feeding chamber. If the molecule to be carried by or packaged inside (enclosed in) the vault particle is smaller than the pore of the semi-permeable membrane, it is preferably added to both chambers in equal concentration to avoid diffusion across the membrane. However, if the molecule to be packaged is larger than the membrane pore, then the molecule may be added to only the reaction chamber.

The in vitro formed vault particles can be easily separated from the components of the translation machinery by multiple purification techniques known in the art, such as chromatography, precipitation, or sedimentation.

Because the method of the present invention employs a cell-free system, there is no cellular debris resulting from the nucleus, cytoskeleton, cell membrane lipids, etc. that arise from cell-based systems. Thus, such cellular debris does not result and the vault particles produced according to the present invention are free of such cellular debris.

The methods described herein may be readily adapted to package one or more passenger molecules, which can be chemicals and biomolecules, including peptides, hydrophobic drugs (e.g., doxorubicin), and the like. In some embodiments, engineered vaults according to the present invention can be targeted to specific cell surface receptors as described by, for example, Kickhoefer, et al. (2009) ACS Nano 3(1): 27-36.

Advantages of Making Vaults Using Cell-Free Techniques

The present invention provides several advantages over prior art methods of making and packaging vault particles. Specifically, the present invention allows the packaging of a variety of passenger molecules, including proteins, DNA, RNA, small ligands, and chemicals into vaults as they are being made. This can be done using in vitro translation of vaults with cell-free techniques. The passenger molecules can be added to the synthesis mixtures used to make the engineered vaults. Alternatively, if the passenger molecules are proteins, the proteins can be made by in vitro translation at the same time and in the same translation mixture used to make the engineered vaults. Passenger molecules, such as inorganic small molecules, can be packaged in vaults at a desired concentration by adding the passenger molecules to the synthesis mixture in a concentration that will result in the desired concentration when packaged in the vaults.

Thus, the advantages of the present invention include:
The ability to package a variety of one or more passenger molecules, e.g., lipophilic proteins that cannot be added in solution, RNA/DNA, small molecule (inorganic) drugs that cannot be tagged for packaging, and the like, that cannot be packaged using prior art methods, including the INT-fusion method.
The ability to produce vault particles in a cell-free system, thereby avoiding contaminants resulting from cell-based methods, including pathogens, pyrogens, antigens, and the like, that are found in cells.
The ability to obtain compositions comprising highly pure and concentrated amounts of vault particles without the need for separating the vault particles from cellular debris resulting from cell-based methods, thereby providing compositions of engineered vaults that are free from reagents used to purify vaults and free from cellular debris and related contaminants.

Additionally, the cell-free methods of making the engineered vaults according to the present invention are significantly more efficient. Specifically, prior art methods of making vault particles usually take about a minimum of 30 days to produce vault particles in insect cells and purify the particles (including cloning, generating recombinant Bacmid DNA, producing the baculovirus, and amplifying the baculovirus). Conversely, the time required to conduct the method according to the present invention is about 1 day and includes the time for PCR amplification of the MVP sequence, in vitro transcription and translation, and removal of ribosomes using either RNase A or Streptomycin Sulfate with subsequent table top centrifugation.

Table 2 itemizes some of the advantages of using a cell-free expression system over cell-based expression systems such as the baculoviral insect cell system for making vaults.

TABLE 2

|  | Wheat germ | Baculovirus |
| --- | --- | --- |
| Coverage of proteins expressed | Excellent | Good |
| Folding and activity | Good | Good |
| Through-put | Excellent | Poor |
| Processing time | 1-2 days | 1-2 months |
| Amino acid labeling | Excellent | Poor |
| Undesired glycosylation | No | Insect type |
| Codon optimization | Not required | Necessary for those proteins encoded by AT-rich cDNAs |
| Temperature range | Broad (15-26° C.) | Narrow (26-28° C.) |
| Yield (per ml of reaction) | 10 mg | 0.5-1 mg |
| Ease of use | Minimal technical training and skill required | High levels of technical training and skill required |
| Scalability | Excellent | Good |
| Purity | Excellent | Poor |

Materials and Methods

Production of Vaults Using Cell-Based Expression System

To produce recombinant vaults made by a cell-based expression system, a baculovirus system (Invitrogen, Waltham, Mass.) was used to infect insect Sf9 cells as previously described. See Stephen, et al. (2001) J Biol Chem 276: 23217-23220. Infected Sf9 cells were then lysed in Buffer A (50 mM Tris-Cl, pH 7.4, 75 mM NaCl, 0.5 mM $MgCl_2$) supplemented with 1% Triton X-100 plus RNAse A (0.1-0.2 µg/ml final concentration), incubated on ice for 30 minutes followed by centrifugation at 20,000×g at 4° C. for 20 minutes. The clarified supernatant (S20) was collected and recombinant vaults were visualized by electron microscopy.

Preparation of Polyribosomes

Sf9 cells infected with either 6-His-MVP or wild type MVP baculoviruses were harvested 24 hours and 48 hours post infection. Cells were lysed on ice for 5 minutes in buffer containing 15 mM HEPES-KOH pH 7.5, 5 mM $MgCl_2$, 100 mM KCl, 0.1 mM EDTA and 1% Triton-X-100. Cell lysates were clarified by centrifugation at 10,000×g for 5 minutes at 4° C. Clarified cell lysates were overlaid onto sucrose step gradients (20%, 30%, 40%, 45%, 50%, and 60%) and centrifuged at 25K for 2.5 hours at 4° C. (Beckman SW41 rotor). The 45% sucrose fraction was collected and designated the polyribosome fraction.

Electron Microscopy (EM)

Samples were assessed by EM using negative staining with 1% aqueous uranyl acetate as previously described. See Poderycki, et al. (2006) Biochemistry 45:12184-12193. Grids were examined on a JEM1200EX (JEOL) electron microscope and micrographs were captured with a BioScan 600W digital camera (Gatan, Pleasanton, Calif.).

Cryo-Electron Tomography (Cryo-ET) and Image Processing

Cryo samples were prepared by placing a small drop (about 4 µl) of sample solution onto a glow discharged holey carbon mesh (Quantifoil 200 mesh grid with 3.5 µm holes spaced 1 µm apart). The grids were blotted and plunged immediately into liquid nitrogen cooled liquid ethane to rapidly freeze the samples in vitrified ice. The cryo samples were visualized with an FEI Titan Krios transmission electron microscope with an accelerating voltage of 300 kV. The samples were imaged at 50,000× to 100,000× with an underfocus value of 3 µm at zero degrees tilt, utilizing an energy filter. Tomography tilt series were taken using the FEI Batch Tomography software to set up and automatically acquire sample images with a tilt range from −70° to +70°. The tilt series were recorded on an Ultrascan 4 megapixel CCD camera (Gatan, Pleasanton, Calif.). Alignment of the tilt series was performed using the etomo tomography processing software from the Imod package. The steps included X-ray removal, rough alignment by cross-correlation, and fine alignment by fiducial gold tracking. The aligned tilt series were then used to make a 3D reconstruction using GPU-based SIRT (Simultaneous Iterative Reconstruction Technique) reconstruction implemented in Inspect3D. The 3D reconstructions were saved as a stack of X-Y plane images that are single pixel slices along the Z-plane. Slices from the reconstructions were displayed using slicer within 3dmod from the Imod package.

Production of Vaults Using Cell-Free Techniques

Vaults were produced using a cell-free system for in vitro translation of MVP mRNA. In particular, for the polyribosome templating experiments, the insect-based cell-free system EasyXpress Insect Kit II (Qiagen, Valencia, Calif.) was used in accordance with the protocol described by the manufacturer. In vitro synthesized recombinant vaults were further treated with RNase A and purified over 20% sucrose cushion (centrifuged at 100,000×g for 2 hours at 4° C. in Beckman coulter Ti 70.1 rotor). Pellets were then dissolved in buffer A and visualized by EM. For the packaging experiments, the RTS 100 Wheat Germ CECF Kit (Biotechrabbit, Hennigsdorf, Germany) was used as described above.

Differential Centrifugation and Western Blot Analysis

Infected Sf9 cells were lysed as described above and centrifuged at 20,000 g for 20 minutes at 4° C. The supernatant, referred to as S20, was diluted in 7.5 ml of buffer A and subsequently centrifuged at 100,000 g for 1 hour at 4° C. after reserving 5 µl for future electrophoretic analysis. The obtained pellet and supernatant, referred to as P100 and S100 respectively, were then diluted in 7.5 ml buffer A each and 5 µl of each fraction were subjected to electrophoresis.

Sodium dodecyl sulfate—polyacrylamide gel electrophoretic (SDS-PAGE) analysis was carried out on minigels (4-12% acrylamide, Bio-Rad, Hercules, Calif.). Separated proteins were transferred to Hybond-C nitrocellulose membrane (GE-Healthcare, Pittsburgh, Pa.) for 1 hour, by means of a Mini-PROTEAN® II Cell apparatus (Bio-Rad, Hercules, Calif.), and incubated in TTBS (50 mM Tris-HCl, 0.1% Tween-20, 150 mM NaCl, pH 7.5), containing 5% nonfat dry milk for 1 hour. Samples were then incubated overnight in TTBS/3% nonfat dry milk, containing the primary antibody (MVP polyclonal rabbit, 1:2,000). After several washes in TTBS, the membrane was incubated in TTBS/5% nonfat dry milk containing goat anti-rabbit Ab coupled to horseradish peroxidase (1:2,000; Bio-Rad, Hercules, Calif.) for 2 hours. After several washes in TTBS, immunoreactive bands were visualized by using an enhanced chemiluminescence (ECL) Western blotting detection kit (GE-Healthcare, Pittsburgh, Pa.) according to manufacturer's instructions. The membrane was then immediately exposed to Fuji medical x-ray film Rx-U in a film cassette at room temperature.

REFERENCES

The following references are herein incorporated by reference in their entirety:

1. Warner J R, Knopf P M, Rich A. A multiple ribosomal structure in protein synthesis. Proc Natl Acad Sci USA. 1963; 49: 122-129.
2. Warner J R, Rich A, Hall C E. Electron Microscope Studies of Ribosomal Clusters Synthesizing Hemoglobin. Science. 1962; 138: 1399-1403.
3. Martin K A, Miller O L, Jr. Polysome structure in sea urchin eggs and embryos: an electron microscopic analysis. Dev Biol. 1983; 98: 338-348.
4. Christensen A K, Bourne C M. Shape of large bound polysomes in cultured fibroblasts and thyroid epithelial cells. Anat Rec. 1999; 255: 116-129.
5. Kopeina G S, Afonina Z A, Gromova K V, Shirokov V A, Vasiliev V D, Spirin A S. Step-wise formation of eukaryotic double-row polyribosomes and circular translation of polysomal mRNA. Nucleic Acids Res. 2008; 36: 2476-2488.
6. Brandt F, Etchells S A, Ortiz J O, Elcock A H, Hartl F U, Baumeister W. The native 3D organization of bacterial polysomes. Cell. 2009; 136: 261-271.
7. Brandt F, Carlson L A, Hartl F U, Baumeister W, Grunewald K. The three-dimensional organization of polyribosomes in intact human cells. Mol Cell. 2010; 39: 560-569.
8. Kedersha N L, Rome L H. Isolation and characterization of a novel ribonucleoprotein particle: large structures contain a single species of small RNA. J. Cell Biol. 1986; 103: 699-709.
9. Berger W, Steiner E, Grusch M, Elbling L, Micksche M. Vaults and the major vault protein: novel roles in signal pathway regulation and immunity. Cell Mol Life Sci. 2009; 66: 43-61.
10. Tanaka H, Kato K, Yamashita E, et al. The structure of rat liver vault at 3.5 angstrom resolution. Science. 2009; 323: 384-388.
11. Mikyas Y, Makabi M, Raval-Fernandes S, et al. Cryo-electron microscopy imaging of recombinant and tissue derived vaults: localization of the MVP N termini and VPARP. J Mol Biol. 2004; 344: 91-105.
12. Anderson D H, Kickhoefer V A, Sievers S A, Rome L H, Eisenberg D. Draft crystal structure of the vault shell at 9-A resolution. PLoS Biol. 2007; 5: e318.
13. Rome L H, Kickhoefer V A. Development of the vault particle as a platform technology. ACS Nano. 2013; 7: 889-902.
14. Pettersen E F, Goddard T D, Huang C C, et al. UCSF Chimera—a visualization system for exploratory research and analysis. J Comput Chem. 2004; 25: 1605-1612.
15. Chandramouli P, Topf M, Menetret J F, et al. Structure of the mammalian 80S ribosome at 8.7 A resolution. Structure. 2008; 16: 535-548.
16. Pfeffer S, Brandt F, Hrabe T, et al. Structure and 3D arrangement of endoplasmic reticulum membrane-associated ribosomes. Structure. 2012; 20: 1508-1518.
17. Nicholls C D, McLure K G, Shields M A, Lee P W. Biogenesis of p53 involves cotranslational dimerization of monomers and posttranslational dimerization of dimers. Implications on the dominant negative effect. J Biol Chem. 2002; 277: 12937-12945.
18. Lin L, DeMartino G N, Greene W C. Cotranslational dimerization of the Rel homology domain of NF-kappaB1 generates p50-p105 heterodimers and is required for effective p50 production. Embo J. 2000; 19: 4712-4722.
19. Fulton A B, L'Ecuyer T. Cotranslational assembly of some cytoskeletal proteins: implications and prospects. J Cell Sci. 1993; 105 (Pt 4): 867-871.
20. Duncan C D, Mata J. Widespread cotranslational formation of protein complexes. PLoS Genet. 2011; 7: e1002398.
21. Stephen A G, Raval-Fernandes S, Huynh T, Tones M, Kickhoefer V A, Rome L H. Assembly of vault-like particles in insect cells expressing only the major vault protein. J Biol Chem. 2001; 276: 23217-23220.
22. Poderycki M J, Kickhoefer V A, Kaddis C S, et al. The vault exterior shell is a dynamic structure that allows incorporation of vault-associated proteins into its interior. Biochemistry. 2006; 45: 12184-12193.

Section headings are used for organizational purposes only and are not to be construed as defining or limiting the subject matter described. Unless explicitly provided otherwise, singular word forms include the plural forms. As used herein, the singular forms "a", "an", and "the" include plural referents unless the context clearly dictates otherwise. As used herein, "and/or" means "and" or "or". For example, "A and/or B" means "A, B, or both A and B" and "A, B, and/or C" means "A, B, C, or a combination thereof" and said "combination thereof" means "A and B, A and C, or B and C". As used herein, "or" can mean "and/or" unless stated otherwise or the context clearly dictates otherwise.

To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

What is claimed is:

1. A cell-free method of making a vault structure by polyribosome templating, which comprises
   incubating a synthesis mixture comprising a polyribosome having an mRNA encoding a major vault protein to produce multiple copies of the major vault protein that are templated into the vault structure.

2. The method of claim 1, wherein the vault structure is an engineered vault, a vault roll, or a vault half.

3. The method of claim 1, wherein the vault structure is an engineered vault.

4. The method of claim 1, wherein the synthesis mixture is free of cells.

5. The method of claim 1, whereby the mRNA is added to the synthesis mixture or the mRNA is provided by adding to the synthesis mixture a vector containing a nucleotide sequence that encodes the major vault protein.

6. The method of claim 1, which further comprises providing one or more passenger molecules in the synthesis mixture during the incubating step.

7. The method of claim 1, which further comprises adding one or more passenger molecules to the synthesis mixture before, during, and/or after the vault structure is formed.

8. The method of claim 7, wherein the one or more passenger molecules are selected from the group consisting of nucleic acid molecules, proteins, amino acids, modified amino acids, lipids, glycolipids, polysaccharides, glycolipids, sterols, vitamins, hormones, small molecules, and combinations thereof.

9. The method of claim 7, wherein at least one of the one or more passenger molecules cannot be packaged into vault particles by mINT fusion packaging.

10. The method of claim 7, wherein at least one of the one or more passenger molecules is recombinantly fused to an mINT sequence.

11. The method of claim 7, wherein at least one of the one or more passenger molecules is fused to an mINT sequence and is added after the vault structure is formed, and at least one of the one or more passenger molecules is not fused to an mINT sequence and is added before and/or during formation of the vault structure.

12. The method of claim 3, which comprises packaging at least two different passenger molecules into the internal cavity of the engineered vault.

13. The method of claim 12, wherein the at least two different passenger molecules comprise a passenger molecule fused to an mINT sequence and a passenger molecule that is not fused to the mINT sequence.

14. A cell-free method of making a vault structure by polyribosome templating, which comprises
   adding a nucleic acid molecule that encodes a major vault protein to a synthesis mixture comprising ribosomes, and
   incubating the synthesis mixture comprising the nucleic acid molecule for 24 hours or more whereby a polyribosome forms and templates copies of the major vault protein into the vault structure.

15. The method of claim 14, which comprises incubating about 0.5 ml of the synthesis mixture comprising the nucleic acid molecule for about 40 hours to produce up to about 250 µg of vault structures.

16. The method of claim 14, wherein the nucleic acid molecule is a vector containing a nucleotide sequence that encodes the major vault protein or an mRNA that encodes the major vault protein.

* * * * *

```
                        SEQUENCE LISTING

<160> NUMBER OF SEQ ID NOS: 15

<210> SEQ ID NO 1
<211> LENGTH: 20
<212> TYPE: PRT
<213> ORGANISM: Rattus norvegicus

<400> SEQUENCE: 1

Met Ala Thr Glu Glu Ala Ile Ile Arg Ile Pro Pro Tyr His Tyr Ile
1               5                   10                  15

His Val Leu Asp
            20

<210> SEQ ID NO 2
<211> LENGTH: 20
<212> TYPE: PRT
<213> ORGANISM: Artificial Sequence
<220> FEATURE:
<223> OTHER INFORMATION: Modified N-terminus of Major Vault Protein of
      Rattus norvegicus

<400> SEQUENCE: 2

Met Ala His Glu Glu Ala Ile Ile Arg Ile Pro Pro Tyr His Tyr Ile
1               5                   10                  15

His Val Leu Asp
            20

<210> SEQ ID NO 3
<211> LENGTH: 20
<212> TYPE: PRT
<213> ORGANISM: Artificial Sequence
<220> FEATURE:
<223> OTHER INFORMATION: Modified N-terminus of Major Vault Protein of
      Rattus norvegicus

<400> SEQUENCE: 3

Met Ala His His Glu Ala Ile Ile Arg Ile Pro Pro Tyr His Tyr Ile
1               5                   10                  15

His Val Leu Asp
            20

<210> SEQ ID NO 4
<211> LENGTH: 20
<212> TYPE: PRT
<213> ORGANISM: Artificial Sequence
<220> FEATURE:
<223> OTHER INFORMATION: Modified N-terminus of Major Vault Protein of
      Rattus norvegicus

<400> SEQUENCE: 4

Met Ala His His His Ala Ile Ile Arg Ile Pro Pro Tyr His Tyr Ile
1               5                   10                  15

His Val Leu Asp
```

<210> SEQ ID NO 5
<211> LENGTH: 20
<212> TYPE: PRT
<213> ORGANISM: Artificial Sequence
<220> FEATURE:
<223> OTHER INFORMATION: Modified N-terminus of Major Vault Protein of
      Rattus norvegicus

<400> SEQUENCE: 5

Met Ala His His His His Ile Ile Arg Ile Pro Pro Tyr His Tyr Ile
1               5                   10                  15

His Val Leu Asp
            20

<210> SEQ ID NO 6
<211> LENGTH: 20
<212> TYPE: PRT
<213> ORGANISM: Artificial Sequence
<220> FEATURE:
<223> OTHER INFORMATION: Modified N-terminus of Major Vault Protein of
      Rattus norvegicus

<400> SEQUENCE: 6

Met Ala His His His His His Ile Arg Ile Pro Pro Tyr His Tyr Ile
1               5                   10                  15

His Val Leu Asp
            20

<210> SEQ ID NO 7
<211> LENGTH: 20
<212> TYPE: PRT
<213> ORGANISM: Artificial Sequence
<220> FEATURE:
<223> OTHER INFORMATION: Modified N-terminus of Major Vault Protein of
      Rattus norvegicus

<400> SEQUENCE: 7

Met Ala His His His His His His Arg Ile Pro Pro Tyr His Tyr Ile
1               5                   10                  15

His Val Leu Asp
            20

<210> SEQ ID NO 8
<211> LENGTH: 3236
<212> TYPE: DNA
<213> ORGANISM: Artificial Sequence
<220> FEATURE:
<223> OTHER INFORMATION: pIVEX 1.3 Wheat Germ Expression Vector sequence

<400> SEQUENCE: 8
ataaggcgca gcggtcgggc tgaacggggg gttcgtgcac acagcccagc ttggagcgaa      60
cgacctacac cgaactgaga tacctacagc gtgagctatg agaaagcgcc acgcttcccg     120
aagggagaaa ggcggacagg tatccggtaa gcggcagggt cggaacagga gagcgcacga    180
gggagcttcc agggggaaac gcctggtatc tttatagtcc tgtcgggttt cgccacctct    240
gacttgagcg tcgatttttg tgatgctcgt caggggggcg gagcctatgg aaaaacgcca    300
gcaacgcggc cttttttacgg ttcctggcct tttgctggcc ttttgctcac atgttctttc    360
ctgcgttatc ccctgattct gtggataacc gtattaccgc ctttgagtga gctgataccg    420
ctcgccgcag ccgaacgacc gagcgcagcg agtcagtgag cgaggaagcg gaagagcgcc    480

-continued

```
caatacgcaa accgcctctc cccgcgcgtt ggccgattca ttaatgcagc tggcacgaca      540
ggtttcccga ctggaaagcg ggcagtgagc gcaacgcaat taatgtgagt tagctcactc      600
attaggcacc ccaggcttta cactttatgc ttccggctcg tatgttgtgt ggaattgtga      660
gcggataaca atttcacaca ggaaacagct atgaccatga ttacgccaag ctcattaata      720
cgactcacta taggcctaag cttacaaata ctcccccaca acagcttaca atactccccc      780
acacagctta caaatactcc cccacaacag cttgtcgaac catggcacat atgagcggcc      840
gcgtcgactc gagcgagctc ccggggggggg ttctcatcat catcatcatc attaataagg      900
tacccagctc ttctggtttg gtttggacct ctggtcctgc aacttgaggt agtcaagatg      960
cataataaat aacggattgt gtccgtaatc acacgtggtg cgtacgataa cgcatagtgt     1020
ttttccctcc acttaaatcg aagggttgtg tcttggatcg cgcgggtcaa atgtatatgg     1080
ttcatataca tccgcaggca cgtaataaag cgaggggttc gaatcccccc gttaccccg      1140 gtagggccc atatatgcgg aattcactgg ccgtcgtttt acaacgtcgt gactgggaaa      1200
accctggcgt tacccaactt aatcgccttg cagcacatcc ccctttcgcc agctggcgta     1260
atagcgaaga ggcccgcacc gatcgccctt cccaacagtt gcgcagcctg aatggcgaat     1320
ggaaattgta agcgttaata ttttgttaaa attcgcgtta aattttttgtt aaatcagctc     1380 attttttaac caataggccg aaatcggcaa atcccttat aaatcaaaag aatagaccga      1440
gatagggttg agtgttgttc cagtttggaa caagagtcca ctattaaaga acgtggactc     1500
caacgtcaaa gggcgaaaaa ccgtctatca gggcgatggc ccactacgtg aaccatcacc     1560
ctaatcaagt ttttggggt cgaggtgccg taaagcacta atcggaacc ctaaagggag       1620 cccccgattt agagcttgac ggggaaagcc ggcgaacgtg gcgagaaagg aagggaagaa     1680
agcgaaagga gcgggcgcta gggcgctggc aagtgtagcg gtcacgctgc gcgtaaccac     1740
cacacccgcc gcgcttaatg cgccgctaca gggcgcgtca ggtggcactt tcggggaaa      1800 tgtgcgcgga acccctattt gtttattttt ctaaatacat tcaaatatgt atccgctcat     1860
gagacaataa ccctgataaa tgcttcaata atattgaaaa aggaagagta tgagtattca     1920
acatttccgt gtcgccctta ttcccttttt tgcggcattt tgccttcctg ttttgctca      1980 cccagaaacg ctggtgaaag taaaagatgc tgaagatcag ttgggtgcac gagtgggtta     2040
catcgaactg gatctcaaca gcggtaagat ccttgagagt tttcgccccg aagaacgttt     2100
tccaatgatg agcacttta aagttctgct atgtggcgcg gtattatccc gtattgacgc      2160
cgggcaagag caactcggtc gccgcataca ctattctcag aatgacttgg ttgagtactc     2220
accagtcaca gaaaagcatc ttacggatgg catgacagta agagaattat gcagtgctgc     2280
cataaccatg agtgataaca ctgcggccaa cttacttctg acaacgatcg gaggaccgaa     2340
ggagctaacc gcttttttgc acaacatggg ggatcatgta actcgccttg atcgttggga     2400
accggagctg aatgaagcca taccaaacga cgagcgtgac accacgatgc ctgtagcaat     2460
ggcaacaacg ttgcgcaaac tattaactgg cgaactactt actctagctt cccggcaaca     2520
attaatagac tggatggagg cggataaagt tgcaggacca cttctgcgct cggcccttcc     2580
ggctggctgg tttattgctg ataaatctgg agccggtgag cgtgggtctc gcggtatcat     2640
tgcagcactg gggccagatg gtaagccctc ccgtatcgta gttatctaca cgacggggag     2700
tcaggcaact atggatgaac gaaatagaca gatcgctgag ataggtgcct cactgattaa     2760
gcattggtaa ctgtcagacc aagtttactc atatatactt tagattgatt taaaacttca     2820 ttttttaattt aaaaggatct aggtgaagat cctttttgat aatctcatga ccaaaatccc     2880
```

```
ttaacgtgag ttttcgttcc actgagcgtc agaccccgta gaaaagatca aggatcttc    2940 ttgagatcct ttttttctgc gcgtaatctg ctgcttgcaa acaaaaaaac caccgctacc   3000
agcggtggtt tgtttgccgg atcaagagct accaactctt tttccgaagg taactggctt   3060
cagcagagcg cagataccaa atactgtcct tctagtgtag ccgtagttag gccaccactt   3120
caagaactct gtagcaccgc ctacatacct cgctctgcta atcctgttac cagtggctgc   3180
tgccagtggc gataagtcgt gtcttaccgg gttggactca agacgatagt taccgg       3236
```

<210> SEQ ID NO 9
<211> LENGTH: 5748
<212> TYPE: DNA
<213> ORGANISM: Artificial Sequence
<220> FEATURE:
<223> OTHER INFORMATION: rMVP-pIVEX 1.3 sequence (based on Rattus
      norvegicus and Wheat Germ sequences)

<400> SEQUENCE: 9

```
ataaggcgca gcggtcgggc tgaacggggg gttcgtgcac acagcccagc ttggagcgaa     60
cgacctacac cgaactgaga tacctacagc gtgagctatg agaaagcgcc acgcttcccg    120
aagggagaaa ggcggacagg tatccggtaa gcggcagggt cggaacagga gagcgcacga    180
gggagcttcc aggggggaaac gcctggtatc tttatagtcc tgtcgggttt cgccacctct   240
gacttgagcg tcgatttttg tgatgctcgt caggggggcg gagcctatgg aaaaacgcca    300
gcaacgcggc cttttacgg ttcctggcct tttgctggcc ttttgctcac atgttctttc    360
ctgcgttatc ccctgattct gtggataacc gtattaccgc ctttgagtga gctgataccg    420
ctcgccgcag ccgaacgacc gagcgcagcg agtcagtgag cgaggaagcg gaagagcgcc   480
caatacgcaa accgcctctc cccgcgcgtt ggccgattca ttaatgcagc tggcacgaca    540
ggtttcccga ctggaaagcg ggcagtgagc gcaacgcaat taatgtgagt tagctcactc    600
attaggcacc ccaggcttta cactttatgc ttccggctcg tatgttgtgt ggaattgtga    660
gcggataaca atttcacaca ggaaacagct atgaccatga ttacgccaag ctcattaata   720
cgactcacta taggcctaag cttacaaata ctcccccaca acagcttaca atactcccc    780 acacagctta caaatactcc cccacaacag cttgtcgaac catggcaact gaagaggcca    840
tcatccgcat ccccccatac cactacatcc atgtgctgga ccagaacagt aatgtgtccc    900
gtgtggaggt tggaccaaag acctacatcc ggcaggacaa tgagagggta ctgtttgccc    960
cagttcgcat ggtgaccgtc cccccacgcc actactgcat agtggccaac cctgtgtccc   1020
gggacaccca gagttctgtg ttatttgaca tcacaggaca agtccgactc cggcacgctg   1080
accaggagat ccgactagcc caggacccct tcccctgta tccaggggag gtgctggaaa    1140
aggacatcac cccactgcag gtggttctgc caacacagc actgcatctt aaggcgttgc   1200
tggactttga ggataagaat ggagacaagg tcatggcagg agacgagtgg ctatttgagg   1260
gacctggcac ctacatccca cagaaggaag tggaagtcgt ggagatcatt caggccacag   1320
tcatcaaaca gaaccaagca ctgcggctaa gggcccgaaa ggagtgcttt gaccgggagg   1380
gcaaggggcg cgtgacaggt gaggagtggc tggtccgatc cgtggggggct acctcccag    1440 ctgtctttga gaggtgctgg atctggtgg atgctgtgat ccttacagaa aagactgccc   1500
tgcacctccg ggctctgcag aacttcaggg accttcgggg agtgctccac cgcaccgggg   1560
aggaatggtt agtgacagtg caggacacag aagcccatgt tccagatgtc tatgaggagg   1620
tgcttggggt agtacccatc accaccctgg gacctcgaca ctactgtgtc attcttgacc   1680
```

```
caatgggacc agacggcaag aaccagctgg acaaaagcg tgttgtcaag ggagagaagt    1740
ccttttcct  ccagccagga gagaggctgg agcgaggcat ccaggatgtg tatgtgctgt    1800
cagagcagca ggggctgcta ctgaaggcac tgcagcccct ggaggaggga gagagcgagg    1860
agaaggtctc ccatcaggcc ggagactgct ggctcatccg tgggccctg  gagtatgtgc    1920
catctgcaaa agtggaggtg gtggaggagc gtcaggctat ccctctggac caaaatgagg    1980
gcatctatgt gcaggatgtc aagacgggga aggtgcgggc tgtgattgga agcacctaca    2040
tgctgactca ggatgaagtc ctgtgggaaa aggagctgcc ttctggggtg gaggagctgc    2100
tgaacttggg gcatgaccct ctggcagaca ggggtcagaa gggcacagcc aagccccttc    2160
agccctcagc tccaaggaac aagacccgag tggtcagcta ccgtgtcccg cacaatgcag    2220
cggtgcaggt ctatgactac agagccaaga gagcccgtgt ggtctttggg cccgagctag    2280
tgacactgga tcctgaggag cagttcacag tattgtccct ttctgccggg cgacccaagc    2340
gtcctcatgc ccgccgtgca ctctgcctac tgctgggacc tgatttcttt actgatgtca    2400
tcaccatcga aactgcagat catgccaggt tgcagctgca gcttgcctac aactggcact    2460
ttgaactgaa gaaccggaat gaccctgcag aggcagccaa gcttttctcc gtgcctgact    2520
tcgtgggtga cgcctgcaag gccattgcat cccgagtccg gggggctgta gcctctgtca    2580
cctttgatga cttccataaa aactcagccc ggatcattcg aatggctgtt tttggctttg    2640
agatgtctga agacacaggt cctgatggca cactcctgcc caaggctcga gaccaggcag    2700
tcttcccca  aaacgggctg gtagtcagca gtgtggatgt gcagtcagtg gagcccgtgg    2760
accagaggac ccgggatgcc cttcagcgca gcgttcagct ggccatcgaa attaccacca    2820
actcccagga ggcagcagcc aagcacgagg ctcagagact ggaacaggaa gcccgtggtc    2880
ggcttgagag gcagaagatc ttggaccagt cagaagctga aaaagcccgc aaggaactct    2940
tggagcttga ggctatgagc atggctgtgg agagcacggg taatgccaaa gcagaggctg    3000
agtcccgtgc agaggcagcg aggatcgaag agaaggctc  tgtgctgcag ccaagctca    3060
aggcacaggc gctagccatt gagacggagg ctgagttgga gcgagtaaag aaagtacgag    3120
agatggaact gatctatgcc cgggcccagt ggagctggag ggtgagcaag gcgcagcagc    3180
ttgccaatgt ggaggcaaag aagttcaagg agatgacaga ggcactgggc cccggcacca    3240
tcagggacct ggctgtggcc gggccagaga tgcaggtgaa acttctccag tccctgggcc    3300
tgaaatccac tctcatcacc gatggctcgt ctcccatcaa cctcttcagc acagccttcg    3360
ggttgctggg gctggggtct gatggtcagc cgccagcaca gaagtaataa ggtacccagc    3420
tcttctggtt tggtttggac ctctggtcct gcaacttgag gtagtcaaga tgcataataa    3480
ataacggatt gtgtccgtaa tcacacgtgg tgcgtacgat aacgcatagt gttttttccct   3540
ccacttaaat cgaagggttg tgtcttggat cgcgcgggtc aaatgtatat ggttcatata    3600
catccgcagg cacgtaataa agcgaggggt tcgaatcccc ccgttacccc cggtaggggc    3660
ccatatatgc ggaattcact ggccgtcgtt ttacaacgtc gtgactggga aaccctggc     3720
gttacccaac ttaatcgcct tgcagcacat ccccctttcg ccagctggcg taatagcgaa    3780
gaggcccgca ccgatcgccc ttcccaacag ttgcgcagcc tgaatggcga atggaaattg    3840
taagcgttaa tattttgtta aaattcgcgt taaattttg  ttaaatcagc tcatttttta    3900
accaataggc cgaaatcggc aaaatcccct ataaatcaaa agaatagacc gagataggt    3960
tgagtgttgt tccagtttgg aacaagagtc cactattaaa gaacgtggac tccaacgtca    4020
```

```
aagggcgaaa aaccgtctat cagggcgatg gcccactacg tgaaccatca ccctaatcaa      4080
gttttttggg gtcgaggtgc cgtaaagcac taaatcggaa ccctaaaggg agccccgat       4140 ttagagcttg acggggaaag ccggcgaacg tggcgagaaa ggaagggaag aaagcgaaag      4200
gagcgggcgc tagggcgctg gcaagtgtag cggtcacgct gcgcgtaacc accacacccg      4260
ccgcgcttaa tgcgccgcta cagggcgcgt caggtggcac ttttcgggga aatgtgcgcg      4320
gaacccctat ttgtttattt ttctaaatac attcaaatat gtatccgctc atgagacaat      4380
aaccctgata aatgcttcaa taatattgaa aaggaagag tatgagtatt caacatttcc       4440
gtgtcgccct tattcccttt tttgcggcat tttgccttcc tgtttttgct cacccagaaa      4500
cgctggtgaa agtaaaagat gctgaagatc agttgggtgc acgagtgggt tacatcgaac      4560
tggatctcaa cagcggtaag atccttgaga gttttcgccc cgaagaacgt tttccaatga      4620
tgagcacttt taaagttctg ctatgtggcg cggtattatc ccgtattgac gccgggcaag      4680
agcaactcgg tcgccgcata cactattctc agaatgactt ggttgagtac tcaccagtca      4740
cagaaaagca tcttacggat ggcatgacag taagagaatt atgcagtgct gccataacca      4800
tgagtgataa cactgcggcc aacttacttc tgacaacgat cggaggaccg aaggagctaa      4860 ccgcttttt gcacaacatg ggggatcatg taactcgcct tgatcgttgg gaaccggagc       4920
tgaatgaagc cataccaaac gacgagcgtg acaccacgat gcctgtagca atggcaacaa      4980
cgttgcgcaa actattaact ggcgaactac ttactctagc ttcccggcaa caattaatag      5040
actggatgga ggcggataaa gttgcaggac cacttctgcg ctcggccctt ccggctggct      5100
ggtttattgc tgataaatct ggagccggtg agcgtgggtc tcgcggtatc attgcagcac      5160
tggggccaga tggtaagccc tcccgtatcg tagttatcta cacgacgggg agtcaggcaa      5220
ctatggatga acgaaataga cagatcgctg agataggtgc ctcactgatt aagcattggt      5280
aactgtcaga ccaagtttac tcatatatac tttagattga tttaaaactt catttttaat      5340
ttaaaaggat ctaggtgaag atcctttttg ataatctcat gaccaaaatc ccttaacgtg      5400
agttttcgtt ccactgagcg tcagaccccg tagaaaagat caaaggatct tcttgagatc      5460 cttttttct gcgcgtaatc tgctgcttgc aaacaaaaaa accaccgcta ccagcggtgg       5520
tttgtttgcc ggatcaagag ctaccaactc tttttccgaa ggtaactggc ttcagcagag      5580
cgcagatacc aaatactgtc cttctagtgt agccgtagtt aggccaccac ttcaagaact      5640
ctgtagcacc gcctacatac ctcgctctgc taatcctgtt accagtggct gctgccagtg      5700
gcgataagtc gtgtcttacc gggttggact caagacgata gttaccgg                  5748
```

<210> SEQ ID NO 10
<211> LENGTH: 3008
<212> TYPE: DNA
<213> ORGANISM: Artificial Sequence
<220> FEATURE:
<223> OTHER INFORMATION: Linear Template for rMVP expression in wheat germ expression system (based on Rattus norvegicus sequence)

<400> SEQUENCE: 10

```
ggataacaat ttcacacagg aaacagctat gaccatgatt acgccaagct cattaatacg       60
actcactata ggcctaagct tacaaatact cccccacaac agcttacaat actccccac       120 acagcttaca aatactcccc cacaacagct tgtcgaacca tggcaactga agaggccatc      180
atccgcatcc cccataccac ctacatccat gtgctggacc agaacagtaa tgtgtcccgt      240
gtggaggttg gaccaaagac ctacatccgg caggacaatg agagggtact gtttgcccca     300
```

```
gttcgcatgg tgaccgtccc cccacgccac tactgcatag tggccaaccc tgtgtcccgg      360
gacacccaga gttctgtgtt atttgacatc acaggacaag tccgactccg gcacgctgac      420
caggagatcc gactagccca ggaccccttc cccctgtatc caggggaggt gctggaaaag      480
gacatcaccc cactgcaggt ggttctgccc aacacagcac tgcatcttaa ggcgttgctg      540
gactttgagg ataagaatgg agacaaggtc atggcaggag acgagtggct atttgaggga      600
cctggcacct catcccaca gaaggaagtg gaagtcgtgg agatcattca ggccacagtc       660
atcaaacaga accaagcact gcggctaagg gcccgaaagg agtgctttga ccgggagggc      720
aaggggcgcg tgacaggtga ggagtggctg gtccgatccg tggggcttaa cctcccagct      780
gtctttgaag aggtgctgga tctggtggat gctgtgatcc ttacagaaaa gactgccctg      840
cacctccggg ctctgcagaa cttcaggac cttcggggag tgctccaccg caccggggag       900
gaatggttag tgacagtgca ggacacagaa gcccatgttc cagatgtcta tgaggaggtg      960
cttggggtag tacccatcac caccctggga cctcgacact actgtgtcat tcttgaccca     1020
atgggaccag acggcaagaa ccagctggga caaaagcgtg ttgtcaaggg agagaagtcc     1080
tttttcctcc agccaggaga gaggctggag cgaggcatcc aggatgtgta tgtgctgtca     1140
gagcagcagg ggctgctact gaaggcactg cagcccctgg aggagggaga gagcgaggag     1200
aaggtctccc atcaggccgg agactgctgg ctcatccgtg ggcccctgga gtatgtgcca     1260
tctgcaaaag tggaggtggt ggaggagcgt caggctatcc ctctggacca aaatgagggc     1320
atctatgtgc aggatgtcaa gacggggaag gtgcgggctg tgattggaag cacctacatg     1380
ctgactcagg atgaagtcct gtgggaaaag gagctgcctt ctggggtgga ggagctgctg     1440
aacttggggc atgaccctct ggcagacagg ggtcagaagg gcacagccaa gccccttcag     1500
ccctcagctc caaggaacaa gacccgagtg gtcagctacc gtgtcccgca caatgcagcg     1560
gtgcaggtct atgactacag agccaagaga gcccgtgtgg tctttgggcc cgagctagtg     1620
acactggatc ctgaggagca gttcacagta ttgtcccttt ctgccgggcg acccaagcgt     1680
cctcatgccc gccgtgcact ctgcctactg ctgggacctg atttctttac tgatgtcatc     1740
accatcgaaa ctgcagatca tgccaggttg cagctgcagc ttgcctacaa ctggcacttt     1800
gaactgaaga accggaatga ccctgcagag gcagccaagc ttttctccgt gcctgacttc     1860
gtgggtgacg cctgcaaggc cattgcatcc cgagtccggg gggctgtagc ctctgtcacc     1920
tttgatgact ccataaaaa ctcagcccgg atcattcgaa tggctgtttt tggctttgag     1980
atgtctgaag acacaggtcc tgatggcaca ctcctgccca aggctcgaga ccaggcagtc     2040
tttccccaaa acgggctggt agtcagcagt gtggatgtgc agtcagtgga gcccgtggac     2100
cagaggaccc gggatgccct tcagcgcagc gttcagctgg ccatcgaaat taccaccaac     2160
tcccaggagg cagcagccaa gcacgaggct cagagactgg aacaggaagc ccgtggtcgg     2220
cttgagaggc agaagatctt ggaccagtca gaagctgaaa aagcccgcaa ggaactcttg     2280
gagcttgagg ctatgagcat ggctgtggag agcacgggta atgccaaagc agaggctgag     2340
tcccgtgcag aggcagcgag gatcgaagga gaaggctctg tgctgcaggc caagctcaag     2400
gcacaggcgc tagccattga cacggaggct gagttggagc gagtaaagaa agtacgagag     2460
atggaactga tctatgcccg ggcccagttg gagctggagg tgagcaaggc gcagcagctt     2520
gccaatgtgg aggcaaagaa gttcaaggag atgacagagg cactgggccc cggcaccatc     2580
agggacctgc tgtggccgg gccagagatg caggtgaaac ttctccagtc cctgggcctg     2640
aaatccactc tcatcaccga tggctcgtct cccatcaacc tcttcagcac agccttcggg     2700
```

```
ttgctgggc tggggtctga tggtcagccg ccagcacaga agtaataagg tacccagctc    2760
ttctggtttg gtttggacct ctggtcctgc aacttgaggt agtcaagatg cataataaat    2820
aacggattgt gtccgtaatc acacgtggtg cgtacgataa cgcatagtgt ttttccctcc    2880
acttaaatcg aagggttgtg tcttggatcg cgcgggtcaa atgtatatgg ttcatataca    2940
tccgcaggca cgtaataaag cgagggggttc gaatccccccc gttaccccccg gtaggggccc    3000 atatatgc                                                             3008

<210> SEQ ID NO 11
<211> LENGTH: 3021
<212> TYPE: DNA
<213> ORGANISM: Artificial Sequence
<220> FEATURE:
<223> OTHER INFORMATION: Linear Template (3021 bp) for rMVP mRNA
      transcription reaction (based on Rattus norvegicus sequence)

<400> SEQUENCE: 11
ggataacaat ttcacacagg aaacagctat gaccatgatt acgccaagct cattaatacg      60
actcactata ggcctaagct tacaaatact ccccccacaac agcttacaat actcccccac    120
acagcttaca aatactcccc cacaacagct tgtcgaacca tggcaactga agaggccatc    180
atccgcatcc ccccatacca ctacatccat gtgctggacc agaacagtaa tgtgtcccgt    240
gtggaggttg gaccaaagac ctacatccgg caggacaatg agagggtact gtttgccccca    300 gttcgcatgg tgaccgtccc cccacgccac tactgcatag tggccaaccc tgtgtcccgg    360
gacacccaga gttctgtgtt atttgacatc acaggacaag tccgactccg gcacgctgac    420
caggagatcc gactagccca ggacccctcc ccctgtatc caggggaggt gctggaaaag    480
gacatcaccc cactgcaggt ggttctgccc aacacagcac tgcatcttaa ggcgttgctg    540
gactttgagg ataagaatgg agacaaggtc atggcaggag acgagtggct atttgaggga    600
cctggcacct acatcccaca gaaggaagtg gaagtcgtgg agatcattca ggccacagtc    660
atcaaacaga accaagcact gcggctaagg gcccgaaagg agtgctttga ccgggagggc    720
aaggggcgcg tgacaggtga ggagtggctg gtccgatccg tggggctta cctcccagct    780 gtcttttgaag aggtgctgga tctggtggat gctgtgatcc ttacagaaaa gactgccctg    840 caccctccggg ctctgcagaa cttcaggac cttcggggag tgctccaccg caccggggag    900
gaatggttag tgacagtgca ggacacagaa gcccatgttc cagatgtcta tgaggaggtg    960 cttgggggtag tacccatcac cacccctggga cctcgacact actgtgtcat tcttgaccca    1020
atgggaccag acggcaagaa ccagctggga caaaagcgtg ttgtcaaggg agagaagtcc    1080 ttttttcctcc agccaggaga gaggctggag cgaggcatcc aggatgtgta tgtgctgtca    1140
gagcagcagg ggctgctact gaaggcactg cagcccctgg aggagggaga gagcgaggag    1200
aaggtctccc atcaggccgg agactgctgg ctcatccgtg ggcccctgga gtatgtgcca    1260
tctgcaaaag tggaggtggt ggaggagcgt caggctatcc ctctggacca aaatgagggc    1320
atctatgtgc aggatgtcaa gacggggaag gtgcgggctg tgattggaag cacctacatg    1380
ctgactcagg atgaagtcct gtgggaaaag gagctgcctt ctggggtgga ggagctgctg    1440
aacttggggc atgaccctct ggcagacagg ggtcagaagg gcacagccaa gcccttcag    1500 ccctcagctc caaggaacaa gacccgagtg tcagctacc gtgtcccgca caatgcagcg    1560
gtgcaggtct atgactacag agccaagaga gcccgtgtgg tctttgggcc cgagctagtg    1620
acactggatc ctgaggagca gttcacagta ttgtcccttt ctgccggggcg acccaagcgt    1680
```

```
cctcatgccc gccgtgcact ctgcctactg ctgggacctg atttctttac tgatgtcatc    1740
accatcgaaa ctgcagatca tgccaggttg cagctgcagc ttgcctacaa ctggcacttt    1800
gaactgaaga accggaatga ccctgcagag gcagccaagc ttttctccgt gcctgacttc    1860
gtgggtgacg cctgcaaggc cattgcatcc cgagtccggg gggctgtagc ctctgtcacc    1920
tttgatgact ccataaaaa ctcagcccgg atcattcgaa tggctgtttt tggctttgag    1980
atgtctgaag acacaggtcc tgatggcaca ctcctgccca aggctcgaga ccaggcagtc    2040
tttccccaaa acgggctggt agtcagcagt gtggatgtgc agtcagtgga gcccgtggac    2100
cagaggaccc gggatgccct tcagcgcagc gttcagctgg ccatcgaaat taccaccaac    2160
tcccaggagg cagcagccaa gcacgaggct cagagactgg aacaggaagc ccgtggtcgg    2220
cttgagaggc agaagatctt ggaccagtca aagctgaaaa agcccgcaa ggaactcttg    2280 gagcttgagg ctatgagcat ggctgtggag agcacgggta atgccaaagc agaggctgag    2340
tcccgtgcag aggcagcgag gatcgaagga gaaggctctg tgctgcaggc caagctcaag    2400
gcacaggcgc tagccattga cggaggct gagttggagc gagtaaagaa agtacgagag    2460
atggaactga tctatgcccg ggcccagttg gagctggagg tgagcaaggc gcagcagctt    2520
gccaatgtgg aggcaaagaa gttcaaggag atgacagagg cactgggccc cggcaccatc    2580
agggacctgg ctgtggccgg gccagagatg caggtgaaac ttctccagtc cctgggcctg    2640
aaatccactc tcatcaccga tggctcgtct cccatcaacc tcttcagcac agccttcggg    2700 ttgctgggc tggggtctga tggtcagccg ccagcacaga agtaataagg tacccagctc    2760
ttctggtttg gtttggacct ctggtcctgc aacttgaggt agtcaagatg cataataaat    2820
aacggattgt gtccgtaatc acacgtggtg cgtacgataa cgcatagtgt ttttccctcc    2880
acttaaatcg aagggttgtg tcttggatcg cgcgggtcaa atgtatatgg ttcatataca    2940
tccgcaggca cgtaataaag cgaggggttc gaatccccccc gttaccccccg gtaggggccc    3000 atatatgcgg aattcactgg c                                              3021

<210> SEQ ID NO 12
<211> LENGTH: 2679
<212> TYPE: DNA
<213> ORGANISM: Homo sapiens

<400> SEQUENCE: 12
atggcaactg aagagttcat catccgcatc ccccatacc actatatcca tgtgctggac     60
cagaacagca acgtgtcccg tgtggaggtc gggccaaaga cctacatccg gcaggacaat    120
gagagggtac tgtttgcccc catgcgcatg gtgaccgtcc ccccacgtca ctactgcaca    180
gtggccaacc ctgtgtctcg ggatgccag ggcttgtgc tgtttgatgt cacagggcaa    240
gttcggcttc gccacgctga cctcgagatc cggctggccc aggaccccctt ccccctgtac    300 ccaggggagg tgctggaaaa ggacatcaca ccccctgcagg tggttctgcc caacactgcc    360
ctccatctaa aggcgctgct tgattttgag gataaagatg gagacaaggt ggtggcagga    420
gatgagtggc ttttcgaggg acctggcacg tacatccccc ggaaggaagt ggaggtcgtg    480
gagatcattc aggccaccat catcaggcag aaccaggctc tgcggctcag gccccgcaag    540
gagtgctggg accgggacgg caaggagagg gtgacagggg aagaatggct ggtcaccaca    600
gtaggggcgt acctcccagc ggtgtttgag gaggttctgg attggtgga cgccgtcatc    660 cttacggaaa agacagccct gcacctccgg gctcggcgga acttccggga cttcagggga    720
```

```
gtgtcccgcc gcactgggga ggagtggctg gtaacagtgc aggacacaga ggcccacgtg    780
ccagatgtcc acgaggaggt gctgggggtt gtgcccatca ccaccctggg ccccacaac     840 tactgcgtga ttctcgaccc tgtcggaccg gatggcaaga atcagctggg gcagaagcgc    900
gtggtcaagg gagagaagtc ttttttcctc cagccaggag agcagctgga acaaggcatc    960
caggatgtgt atgtgctgtc ggagcagcag gggctgctgc tgagggccct gcagcccctg   1020 gaggagggg  aggatgagga gaaggtctca caccaggctg ggaccactg  gctcatccgc   1080 ggaccctgg  agtatgtgcc atctgccaaa gtggaggtgg tggaggagcg ccaggccatc   1140
cctctagacg agaacgaggg catctatgtg caggatgtca agaccggaaa ggtgcgcgct   1200
gtgattggaa gcacctacat gctgacccag gacgaagtcc tgtgggagaa agagctgcct   1260
cccggggtgg aggagctgct gaacaagggg caggaccctc tggcagacag gggtgagaag   1320
gacacagcta agagcctcca gcccttggcg ccccggaaca agaccgtgt  ggtcagctac   1380 cgcgtgcccc acaacgctgc ggtgcaggtg tacgactacc gagagaagcg agcccgcgtg   1440
gtcttcgggc tgagctggt  gtcgctgggt cctgaggagc agttcacagt gttgtccctc   1500
tcagctgggc ggcccaagcg tccccatgcc cgccgtgcgc tctgcctgct gctggggcct   1560
gacttcttca cagacgtcat caccatcgaa acggcggatc atgccaggct gcaactgcag   1620
ctggcctaca actggcactt tgaggtgaat gaccggaagg accccaaga  gacggccaag   1680 ctcttttcag tgccagactt tgtaggtgat gcctgcaaag ccatcgcatc ccgggtgcgg   1740
ggggccgtgg cctctgtcac tttcgatgac ttccataaga actcagcccg catcattcgc   1800
actgctgtct ttggctttga gacctcggaa gcgaagggcc ccgatggcat ggcccctgccc  1860 aggccccggg accaggctgt cttcccccaa aacgggctgg tggtcagcag tgtggacgtg   1920
cagtcagtga agcctgtgga tcagaggacc cgggacgccc tgcaacgcag cgtccagctg   1980
gccatcgaga tcaccaccaa ctcccaggaa gcggcggcca agcatgaggc tcagagactg   2040
gagcaggaag cccgcggccg gcttgagcgg cagaagatcc tggaccagtc agaagccgag   2100
aaagctcgca aggaactttt ggagctggag gctctgagca tggccgtgga gagcaccggg   2160
actgccaagg cggaggccga gtcccgtgcg gaggcagccc ggattgaggg agaagggtcc   2220
gtgctgcagg ccaagctaaa agcacaggcc ttggccattg aaacggaggc tgagctccag   2280
agggtccaga aggtccgaga gctggaactg gtctatgccc gggcccagct ggagctggag   2340
gtgagcaagg ctcagcagct ggctgaggtg gaggtgaaga agttcaagca gatgacagag   2400
gccataggcc ccagcaccat cagggacctt gctgtggctg gcctgagat  gcaggtaaaa   2460 ctgctccagt ccctgggcct gaaatcaacc ctcatcaccg atggctccac tcccatcaac   2520
ctcttcaaca cagcctttgg gctgctgggg atggggcccg agggtcagcc cctgggcaga   2580
agggtggcca gtgggcccag ccctggggag gggatatccc cccagtctgc tcaggcccct   2640
caagctcctg gagacaacca cgtggtgcct gtactgcgc                           2679
```

<210> SEQ ID NO 13
<211> LENGTH: 5844
<212> TYPE: DNA
<213> ORGANISM: Artificial Sequence
<220> FEATURE:
<223> OTHER INFORMATION: Sequence of Human Major Vault Protein cloned
      into the pIVEX 1.3 expression vector.

<400> SEQUENCE: 13

```
ataaggcgca gcggtcgggc tgaacggggg gttcgtgcac acagcccagc ttggagcgaa     60
```

```
cgacctacac cgaactgaga tacctacagc gtgagctatg agaaagcgcc acgcttcccg    120
aagggagaaa ggcggacagg tatccggtaa gcggcagggt cggaacagga gagcgcacga    180
gggagcttcc aggggggaaac gcctggtatc tttatagtcc tgtcgggttt cgccacctct    240
gacttgagcg tcgattttg tgatgctcgt caggggggcg gagcctatgg aaaaacgcca     300
gcaacgcggc cttttacgg ttcctggcct tttgctggcc ttttgctcac atgttctttc     360
ctgcgttatc ccctgattct gtggataacc gtattaccgc ctttgagtga gctgataccg    420
ctcgccgcag ccgaacgacc gagcgcagcg agtcagtgag cgaggaagcg gaagagcgcc    480
caatacgcaa accgcctctc cccgcgcgtt ggccgattca ttaatgcagc tggcacgaca    540
ggtttcccga ctggaaagcg ggcagtgagc gcaacgcaat taatgtgagt tagctcactc    600
attaggcacc ccaggcttta cactttatgc ttccggctcg tatgttgtgt ggaattgtga    660
gcggataaca atttcacaca ggaaacagct atgaccatga ttacgccaag ctcattaata    720
cgactcacta taggcctaag cttacaaata ctcccccaca acagcttaca atactccccc    780
acacagctta caaatactcc cccacaacag cttgtcgaac catggcaact gaagagttca    840
tcatccgcat cccccatac cactatatcc atgtgctgga ccagaacagc aacgtgtccc     900
gtgtggaggt cgggccaaag acctacatcc ggcaggacaa tgagggta ctgtttgccc      960 ccatgcgcat ggtgaccgtc ccccacgtc actactgcac agtggccaac cctgtgtctc    1020
gggatgccca gggcttggtg ctgtttgatg tcacagggca agttcggctt cgccacgctg    1080
acctcgagat ccggctggcc caggaccccct tcccctgta cccaggggag gtgctggaaa    1140
aggacatcac accctgcag gtggttctgc caacactgc cctccatcta aggcgctgc      1200 ttgattttga ggataaagat ggagacaagg tggtggcagg agatgagtgg cttttcgagg    1260
gacctggcac gtacatcccc cggaaggaag tggaggtcgt ggagatcatt caggccacca    1320
tcatcaggca gaaccaggct ctgcggctca gggcccgcaa ggagtgctgg gaccgggacg    1380
gcaaggagag ggtgacaggg gaagaatggc tggtcaccac agtaggggcg tacctcccag    1440
cggtgtttga ggaggttctg gatttggtgg acgccgtcat ccttacggaa aagacagccc    1500
tgcacctccg ggctcggcgg aacttccggg acttcagggg agtgtcccgc cgcactgggg    1560
aggagtggct ggtaacagtg caggacacag aggcccacgt gccagatgtc cacgaggagg    1620
tgctgggggt tgtgcccatc accaccctgg gcccccacaa ctactgcgtg attctcgacc    1680
ctgtcggacc ggatggcaag aatcagctgg ggcagaagcg cgtggtcaag ggagagaagt    1740 ctttttttcct ccagccagga gagcagctgg aacaaggcat ccaggatgtg tatgtgctgt    1800
cggagcagca ggggctgctg ctgagggccc tgcagccccct ggaggagggg gaggatgagg    1860
agaaggtctc acaccaggct ggggaccact ggctcatccg cggaccccctg gagtatgtgc    1920 catctgccaa agtggaggtg gtggaggagc gccaggccat ccctctagac gagaacgagg    1980
gcatctatgt gcaggatgtc aagaccggaa aggtgcgcgc tgtgattgga agcacctaca    2040
tgctgaccca ggacgaagtc ctgtgggaga aagagctgcc tcccgggtg gaggagctgc    2100 tgaacaaggg gcaggaccct ctggcagaca ggggtgagaa ggacacagct aagagcctcc    2160
agcccttggc gccccggaac aagacccgtg tggtcagcta ccgcgtgccc cacaacgctg    2220
cggtgcaggt gtacgactac cgagagaagc gagcccgcgt ggtcttcggg cctgagctgg    2280
tgtcgctggg tcctgaggag cagttcacag tgttgtccct ctcagctggg cggcccaagc    2340
gtccccatgc ccgccgtgcg ctctgcctgc tgctggggcc tgacttcttc acagacgtca    2400
tcaccatcga aacggcggat catgccaggc tgcaactgca gctggcctac aactggcact    2460
```

```
ttgaggtgaa tgaccggaag dacccccaag agacggccaa gctcttttca gtgccagact    2520
ttgtaggtga tgcctgcaaa gccatcgcat cccgggtgcg gggggccgtg gcctctgtca    2580
ctttcgatga cttccataag aactcagccc gcatcattcg cactgctgtc tttggctttg    2640
agacctcgga agcgaagggc cccgatggca tggccctgcc caggcccgg gaccaggctg     2700
tcttccccca aaacgggctg gtggtcagca gtgtggacgt gcagtcagtg gagcctgtgg    2760
atcagaggac ccgggacgcc ctgcaacgca gcgtccagct ggccatcgag atcaccacca    2820
actcccagga agcggcggcc aagcatgagg ctcagagact ggagcaggaa gcccgcggcc    2880
ggcttgagcg gcagaagatc ctggaccagt cagaagccga aaagctcgc aaggaacttt     2940
tggagctgga ggctctgagc atggccgtgg agagcaccgg gactgccaag gcggaggccg    3000
agtcccgtgc ggaggcagcc cggattgagg agaagggtc cgtgctgcag gccaagctaa     3060
aagcacaggc cttggccatt gaaacggagg ctgagctcca gagggtccag aaggtccgag    3120
agctggaact ggtctatgcc cgggcccagc tggagctgga ggtgagcaag gctcagcagc    3180
tggctgaggt ggaggtgaag aagttcaagc agatgacaga ggccataggc cccagcacca    3240
tcagggacct tgctgtggct gggcctgaga tgcaggtaaa actgctccag tccctgggcc    3300
tgaaatcaac cctcatcacc gatggctcca ctcccatcaa cctcttcaac acagcctttg    3360
ggctgctggg gatggggccc gagggtcagc ccctgggcag aagggtggcc agtgggccca    3420
gccctgggga ggggatatcc ccccagtctg tcaggcccc tcaagctcct ggagacaacc     3480
acgtggtgcc tgtactgcgc taataaggta cccagctctt ctggtttggt ttggacctct    3540
ggtcctgcaa cttgaggtag tcaagatgca taataaataa cggattgtgt ccgtaatcac    3600
acgtggtgcg tacgataacg catagtgttt ttccctccac ttaaatcgaa gggttgtgtc    3660
ttggatcgcg cgggtcaaat gtatatggtt catatacatc cgcaggcacg taataaagcg    3720
aggggttcga atccccccgt taccccccggt aggggcccat atatgcggaa ttcactggcc    3780
gtcgttttac aacgtcgtga ctgggaaaac cctggcgtta cccaacttaa tcgccttgca    3840
gcacatcccc ctttcgccag ctggcgtaat agcgaagagg cccgcaccga tcgcccttcc    3900
caacagttgc gcagcctgaa tggcgaatgg aaattgtaag cgttaatatt ttgttaaaat    3960
tcgcgttaaa ttttttgttaa atcagctcat ttttttaacca ataggccgaa atcggcaaaa   4020
tcccttataa atcaaaagaa tagaccgaga tagggttgag tgttgttcca gtttggaaca    4080
agagtccact attaaagaac gtggactcca acgtcaaagg gcgaaaaacc gtctatcagg    4140
gcgatggccc actacgtgaa ccatcaccct aatcaagttt ttttggggtcg aggtgccgta    4200
aagcactaaa tcggaaccct aaagggagcc ccgatttag agcttgacgg ggaaagccgg     4260
cgaacgtggc gagaaaggaa gggaagaaag cgaaaggagc gggcgctagg gcgctggcaa    4320
gtgtagcggt cacgctgcgc gtaaccacca cacccgccgc gcttaatgcg ccgctacagg    4380
gcgcgtcagt tggcactttt cggggaaatg tgcgcggaac ccctatttgt ttatttttct    4440
aaatacattc aaatatgtat ccgctcatga cataaacc ctgataaatg cttcaataat       4500
attgaaaaag gaagagtatg agtattcaac atttccgtgt cgcccttatt cccttttttg    4560
cggcattttg ccttcctgtt tttgctcacc cagaaacgct ggtgaaagta aaagatgctg    4620
aagatcagtt gggtgcacga gtgggttaca tcgaactgga tctcaacagc ggtaagatcc    4680
ttgagagttt tcgccccgaa gaacgttttc caatgatgag cacttttaaa gttctgctat    4740
gtggcgcggt attatcccgt attgacgccg ggcaagagca actcggtcgc cgcatacact    4800
```

-continued

```
attctcagaa tgacttggtt gagtactcac cagtcacaga aaagcatctt acggatggca    4860
tgacagtaag agaattatgc agtgctgcca taaccatgag tgataacact gcggccaact    4920
tacttctgac aacgatcgga ggaccgaagg agctaaccgc ttttttgcac aacatggggg    4980
atcatgtaac tcgccttgat cgttgggaac cggagctgaa tgaagccata ccaaacgacg    5040
agcgtgacac cacgatgcct gtagcaatgg caacaacgtt gcgcaaacta ttaactggcg    5100
aactacttac tctagcttcc cggcaacaat taatagactg gatggaggcg gataaagttg    5160
caggaccact tctgcgctcg gcccttccgg ctggctggtt tattgctgat aaatctggag    5220
ccggtgagcg tgggtctcgc ggtatcattg cagcactggg gccagatggt aagccctccc    5280
gtatcgtagt tatctacacg acggggagtc aggcaactat ggatgaacga atagacaga    5340
tcgctgagat aggtgcctca ctgattaagc attggtaact gtcagaccaa gtttactcat    5400
atatacttta gattgattta aaacttcatt tttaatttaa aaggatctag gtgaagatcc    5460
tttttgataa tctcatgacc aaaatccctt aacgtgagtt ttcgttccac tgagcgtcag    5520
accccgtaga aaagatcaaa ggatcttctt gagatccttt ttttctgcgc gtaatctgct    5580
gcttgcaaac aaaaaaacca ccgctaccag cggtggtttg tttgccggat caagagctac    5640
caactctttt tccgaaggta actggcttca gcagagcgca gataccaaat actgtccttc    5700
tagtgtagcc gtagttaggc caccacttca agaactctgt agcaccgcct acatacctcg    5760
ctctgctaat cctgttacca gtggctgctg ccagtggcga taagtcgtgt cttaccgggt    5820
tggactcaag acgatagtta ccgg                                           5844
```

<210> SEQ ID NO 14
<211> LENGTH: 2730
<212> TYPE: DNA
<213> ORGANISM: Artificial Sequence
<220> FEATURE:
<223> OTHER INFORMATION: Sequence of Human Major Vault Protein cloned
      into pT7-IRES expression vector.

<400> SEQUENCE: 14

```
taatatggcc acaaccatgg caactgaaga gttcatcatc cgcatccccc cataccacta      60
tatccatgtg ctggaccaga acagcaacgt gtcccgtgtg gaggtcgggc aaagaccta     120
catccggcag gacaatgaga gggtactgtt tgccccatg cgcatggtga ccgtcccccc     180
acgtcactac tgcacagtgg ccaaccctgt gtctcgggat gcccagggct tggtgctgtt     240
tgatgtcaca gggcaagttc ggcttcgcca cgctgacctc gagatccggc tggcccagga     300
ccccttcccc ctgtacccag gggaggtgct ggaaaaggac atcacacccc tgcaggtggt     360
tctgcccaac actgccctcc atctaaaggc gctgcttgat tttgaggata agatggaga     420
caaggtggtg gcaggagatg agtggcttt cgagggacct ggcacgtaca tcccccggaa     480
ggaagtggag gtcgtggaga tcattcaggc caccatcatc aggcagaacc aggctctgcg     540
gctcagggcc gcaaggagt gctgggaccg ggacggcaag gagaggtga cagggggaaga     600
atggctggtc accacagtag gggcgtacct cccagcggtg tttgaggagg ttctggattt     660
ggtggacgcc gtcatcctta cggaaaagac agccctgcac ctccgggctc ggcggaactt     720
ccgggacttc aggggagtgt cccgccgcac tgggagggag tggctggtaa cagtgcagga     780
cacagaggcc cacgtgccag atgtccacga ggaggtgctg ggggttgtgc ccatcaccac     840
cctgggcccc cacaactact gcgtgattct cgaccctgtc ggaccggatg caagaatca     900
gctggggcag aagcgcgtgg tcaagggaga gaagtctttt ttcctccagc aggagagca     960
```

```
gctggaacaa ggcatccagg atgtgtatgt gctgtcggag cagcaggggc tgctgctgag    1020
ggccctgcag cccctggagg aggggggagga tgaggagaag gtctcacacc aggctgggga    1080
ccactggctc atccgcggac ccctggagta tgtgccatct gccaaagtgg aggtggtgga    1140
ggagcgccag gccatccctc tagacgagaa cgagggcatc tatgtgcagg atgtcaagac    1200
cggaaaggtg cgcgctgtga ttggaagcac ctacatgctg acccaggacg aagtcctgtg    1260
ggagaaagag ctgcctcccg gggtggagga gctgctgaac aaggggcagg accctctggc    1320
agacaggggt gagaaggaca cagctaagag cctccagccc ttggcgcccc ggaacaagac    1380
ccgtgtggtc agctaccgcg tgccccacaa cgctgcggtg caggtgtacg actaccgaga    1440
gaagcgagcc cgcgtggtct cgggcctga gctggtgtcg ctgggtcctg aggagcagtt    1500
cacagtgttg tccctctcag ctgggcggcc caagcgtccc catgcccgcc gtgcgctctg    1560
cctgctgctg gggcctgact tcttcacaga cgtcatcacc atcgaaacgg cggatcatgc    1620
caggctgcaa ctgcagctgg cctacaactg gcactttgag gtgaatgacc ggaaggaccc    1680
ccaagagacg gccaagctct tttcagtgcc agactttgta ggtgatgcct gcaaagccat    1740
cgcatcccgg gtgcgggggg ccgtggcctc tgtcactttc gatgacttcc ataagaactc    1800
agcccgcatc attcgcactg ctgtctttgg ctttgagacc tcggaagcga agggccccga    1860
tggcatggcc ctgccaggc cccgggacca ggctgtcttc ccccaaaacg ggctggtggt    1920
cagcagtgtg gacgtgcagt cagtggagcc tgtggatcag aggacccggg acgccctgca    1980
acgcagcgtc cagctggcca tcgagatcac caccaactcc caggaagcgg cggccaagca    2040
tgaggctcag agactggagc aggaagcccg cggccggctt gagcggcaga agatcctgga    2100
ccagtcagaa gccgagaaag ctcgcaagga acttttggag ctggaggctc tgagcatggc    2160
cgtggagagc accgggactg ccaaggcgga ggccgagtcc cgtgcggagg cagcccggat    2220
tgagggagaa gggtccgtgc tgcaggccaa gctaaaagca caggccttgg ccattgaaac    2280
ggaggctgag ctccagaggg tccagaaggt ccgagagctg gaactggtct atgcccgggc    2340
ccagctggag ctggaggtga gcaaggctca gcagctggct gaggtggagg tgaagaagtt    2400
caagcagatg acagaggcca taggccccag caccatcagg gaccttgctg tggctgggcc    2460
tgagatgcag gtaaaactgc tccagtccct gggcctgaaa tcaaccctca tcaccgatgg    2520
ctccactccc atcaacctct tcaacacagc ctttgggctg ctggggatgg gcccgagggg    2580
tcagcccctg ggcagaaggg tggccagtgg gcccagccct ggggagggga tatcccccca    2640
gtctgctcag gccccctcaag ctcctggaga caacccacgtg gtgcctgtac tgcgctaact    2700
agactagcat aaccccttgg ggcctctaaa                                       2730
```

<210> SEQ ID NO 15
<211> LENGTH: 2634
<212> TYPE: DNA
<213> ORGANISM: Artificial Sequence
<220> FEATURE:
<223> OTHER INFORMATION: Sequence of Rat Major Vault Protein cloned into
the pT7-IRES expression vector.

<400> SEQUENCE: 15

```
taatatggcc acaaccatgg caactgaaga ggccatcatc cgcatccccc cataccacta    60
```

-continued

```
catccatgtg ctggaccaga acagtaatgt gtcccgtgtg gaggttggac caaagaccta    120
catccggcag gacaatgaga gggtactgtt tgccccagtt cgcatggtga ccgtcccccc    180
acgccactac tgcatagtgg ccaaccctgt gtcccgggac acccagagtt ctgtgttatt    240
tgacatcaca ggacaagtcc gactccggca cgctgaccag gagatccgac tagcccagga    300
ccccttcccc ctgtatccag gggaggtgct ggaaaaggac atcaccccac tgcaggtggt    360
tctgcccaac acagcactgc atcttaaggc gttgctggac tttgaggata gaatggaga    420
caaggtcatg gcaggagacg agtggctatt tgagggacct ggcacctaca tcccacagaa    480
ggaagtggaa gtcgtggaga tcattcaggc cacagtcatc aaacagaacc aagcactgcg    540
gctaagggcc cgaaaggagt gctttgaccg ggagggcaag gggcgcgtga caggtgagga    600
gtggctggtc cgatccgtgg gggcttacct cccagctgtc tttgaagagg tgctggatct    660
ggtggatgct gtgatcctta cagaaaagac tgccctgcac ctccgggctc tgcagaactt    720
cagggacctt cggggagtgc tccaccgcac cggggaggaa tggttagtga cagtgcagga    780
cacagaagcc catgttccag atgtctatga ggaggtgctt ggggtagtac ccatcaccac    840
cctgggacct cgacactact gtgtcattct tgacccaatg ggaccagacg gcaagaacca    900
gctgggacaa aagcgtgttg tcaagggaga gaagtccttt ttcctccagc caggagagag    960
gctggagcga ggcatccagg atgtgtatgt gctgtcagag cagcaggggc tgctactgaa   1020
ggcactgcag cccctggagg agggagagag cgaggagaag gtctcccatc aggccggaga   1080
ctgctggctc atccgtgggc cctggagta tgtgccatct gcaaagtgg aggtggtgga   1140
ggagcgtcag gctatccctc tggaccaaaa tgagggcatc tatgtgcagg atgtcaagac   1200
ggggaaggtg cgggctgtga ttggaagcac ctacatgctg actcaggatg aagtcctgtg   1260
ggaaaaggag ctgccttctg gggtggagga gctgctgaac ttggggcatg accctctggc   1320
agacaggggt cagaagggca cagccaagcc ccttcagccc tcagctccaa ggaacaagac   1380
ccgagtggtc agctaccgtg tcccgcacaa tgcagcggtg caggtctatg actcagagc   1440
caagagagcc cgtgtggtct ttgggcccga gctagtgaca ctggatcctg aggagcagtt   1500
cacagtattg tccctttctg ccgggcgacc caagcgtcct catgcccgcc gtgcactctg   1560
cctactgctg ggacctgatt tctttactga tgtcatcacc atcgaaactg cagatcatgc   1620
caggttgcag ctgcagcttg cctacaactg gcactttgaa ctgaagaacc ggaatgaccc   1680
tgcagaggca gccaagcttt tctccgtgcc tgacttcgtg ggtgacgcct gcaaggccat   1740
tgcatcccga gtccgggggg ctgtagcctc tgtcaccttt gatgacttcc ataaaaactc   1800
agcccggatc attcgaatgg ctgttttgg ctttgagatg tctgaagaca caggtcctga   1860
tgcacactc ctgcccaagg ctcgagacca ggcagtcttt ccccaaaacg ggctggtagt   1920
cagcagtgtg gatgtgcagt cagtggagcc cgtggaccag aggacccggg atgcccttca   1980
gcgcagcgtt cagctggcca tcgaaattac caccaactcc caggaggcag cagccaagca   2040
cgaggctcag agactggaac aggaagcccg tggtcggctt gagaggcaga agatcttgga   2100
ccagtcagaa gctgaaaaag cccgcaagga actcttggag cttgaggcta tgagcatggc   2160
tgtggagagc acgggtaatg ccaaagcaga ggctgagtcc cgtgcagagg cagcgaggat   2220
cgaaggagaa ggctctgtgc tgcaggccaa gctcaaggca caggcgctag ccattgagac   2280
ggaggctgag ttggagcgag taaagaaagt acgagagatg gaactgatct atgcccgggc   2340
ccagttggag ctgaggtga gcaaggcgca gcagcttgcc aatgtggagg caaagaagtt   2400
caaggagatg acagaggcac tgggccccgg caccatcagg gacctggctg tggccgggcc   2460
```

```
agagatgcag gtgaaacttc tccagtccct gggcctgaaa tccactctca tcaccgatgg    2520
ctcgtctccc atcaacctct tcagcacagc cttcgggttg ctggggctgg ggtctgatgg    2580
tcagccgcca gcacagaagt gactagacta gcataacccc ttggggcctc taaa          2634
```